United States Patent
Freed

(10) Patent No.: US 11,785,939 B2
(45) Date of Patent: *Oct. 17, 2023

(54) APPARATUS AND METHOD FOR EX VIVO LUNG VENTILATION WITH A VARYING EXTERIOR PRESSURE

(71) Applicant: TEVOSOL, INC., Edmonton (CA)

(72) Inventor: Darren Freed, Edmonton (CA)

(73) Assignee: TEVOSOL, INC., Edmonton (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/071,179

(22) Filed: Nov. 29, 2022

(65) Prior Publication Data

US 2023/0089628 A1   Mar. 23, 2023

Related U.S. Application Data

(63) Continuation of application No. 16/305,648, filed as application No. PCT/CA2017/050643 on May 26, 2017, now Pat. No. 11,540,509.

(Continued)

(51) Int. Cl.
*A01N 1/02*      (2006.01)
*A61M 16/00*   (2006.01)
*A61M 16/10*   (2006.01)

(52) U.S. Cl.
CPC ............ *A01N 1/0247* (2013.01); *A01N 1/02* (2013.01); *A01N 1/021* (2013.01); *A01N 1/0242* (2013.01);

(Continued)

(58) Field of Classification Search
CPC .. A01N 1/0289; A01N 1/0242; A01N 1/0247; A61M 16/0009; A61M 16/00;

(Continued)

(56) References Cited

U.S. PATENT DOCUMENTS 5,354,268 A * 10/1994 Peterson ................. A61M 1/74
                                                                   604/35
5,759,148 A *   6/1998 Sipin .................... A61M 60/531
                                                                   600/18

(Continued)

FOREIGN PATENT DOCUMENTS

CN          101677526 A        3/2010
CN          104039135 A        9/2014

(Continued)

OTHER PUBLICATIONS

Mehaffey, et al., "Airway pressure release ventilation during ex vivo lung perfusion attenuates injury", Journal of Thoracic Cardiovascular Surgery, 2017, 153, pp. 197-204.

(Continued)

*Primary Examiner* — Justine R Yu
*Assistant Examiner* — Benjamin M. Kusiak

(57) ABSTRACT

In a method of ventilating excised lungs, a ventilation gas is supplied to an airway of a lung and a vacuum is formed around the lung. A quality of the vacuum is varied between a lower level and a higher level to cause the lung to breathe, while the pressure of the ventilation gas supplied to the airway is regulated to maintain a positive airway pressure in the airway of the lung. The vacuum may be cyclically varied between the two vacuum levels. The levels may be maintained substantially constant over a period of time, or one or both of the lower and higher levels may be adjusted during ventilation. The lung may be placed in a sealed chamber, and a vacuum is formed in the chamber around the lung.

9 Claims, 31 Drawing Sheets

Related U.S. Application Data

(60) Provisional application No. 62/343,076, filed on May 30, 2016.

(52) U.S. Cl.
CPC .......... *A01N 1/0289* (2013.01); *A61M 16/00* (2013.01); *A61M 16/0009* (2014.02); *A61M 16/0057* (2013.01); *A61M 16/1005* (2014.02); *A61M 2205/3344* (2013.01)

(58) Field of Classification Search
CPC .......... A61M 16/0003; A61M 16/0057; A61M 16/105–107; A61M 16/20–205; A61M 2202/0007; A61M 2202/0208; A61M 2016/0027; A61M 2016/003; A61M 2205/07; A61M 2205/3331; A61M 2205/3334; A61M 2205/50; A61M 2205/75; A61M 16/0063; A61M 16/0066; A61M 16/021; A61M 16/1005; A61M 2205/3344; A61M 2202/02
USPC ........................................ 128/204.18; 435/1.2
See application file for complete search history.

(56) References Cited

U.S. PATENT DOCUMENTS

| | | | |
|---|---|---|---|
| 5,807,737 A * | 9/1998 | Schill .................. | A01N 1/0247 435/284.1 |
| 6,526,974 B1 | 3/2003 | Brydon et al. | |
| 6,764,462 B2 | 7/2004 | Risk, Jr. et al. | |
| 6,953,655 B1 | 10/2005 | Hassanein et al. | |
| 8,167,869 B2 * | 5/2012 | Wudyka .................. | A61M 1/984 604/35 |
| 10,124,093 B1 * | 11/2018 | Francis .................. | A61M 1/96 |
| 2002/0198504 A1 | 12/2002 | Risk, Jr. et al. | |
| 2003/0168064 A1 * | 9/2003 | Daly .................. | A61M 16/0816 128/204.18 |
| 2005/0147958 A1 | 7/2005 | Hassanein et al. | |
| 2005/0255442 A1 | 11/2005 | Brassil et al. | |
| 2007/0135752 A1 | 6/2007 | Domash et al. | |
| 2007/0135760 A1 * | 6/2007 | Williams ............ | A61F 9/00736 604/65 |
| 2008/0009815 A1 * | 1/2008 | Grabenkort ............ | A61M 1/81 604/74 |
| 2008/0017194 A1 | 1/2008 | Hassanein et al. | |
| 2008/0295839 A1 * | 12/2008 | Habashi ............ | A61M 16/0051 128/204.22 |
| 2009/0182302 A1 * | 7/2009 | Garabet .................. | A61M 31/00 604/500 |
| 2009/0197240 A1 * | 8/2009 | Fishman .............. | A01N 1/0247 128/200.24 |
| 2010/0028850 A1 * | 2/2010 | Brassil .................. | A01N 1/021 435/284.1 |
| 2010/0204663 A1 * | 8/2010 | Wudyka .................. | A61M 1/742 604/313 |
| 2011/0294108 A1 * | 12/2011 | Argoudelis .......... | A01N 1/0247 435/284.1 |
| 2012/0064050 A1 | 3/2012 | Calle et al. | |
| 2012/0330438 A1 * | 12/2012 | Keshavjee .......... | A01N 1/0215 623/23.65 |
| 2013/0102917 A1 * | 4/2013 | Colbaugh ............ | A61M 16/06 600/533 |
| 2013/0144227 A1 * | 6/2013 | Locke .................. | A61M 1/98 604/319 |
| 2013/0220325 A1 | 8/2013 | Davis et al. | |
| 2014/0007961 A1 * | 1/2014 | Steen .................. | A01N 1/0289 137/565.17 |
| 2014/0220550 A1 | 8/2014 | Van Der Plaats et al. | |
| 2014/0283828 A1 * | 9/2014 | Acker .................. | A61M 16/04 128/203.14 |
| 2014/0308654 A1 * | 10/2014 | Kay ...................... | A01N 1/021 435/284.1 |
| 2014/0315175 A1 | 10/2014 | Nguyen | |
| 2015/0093738 A1 | 4/2015 | Potenziano et al. | |
| 2015/0246164 A1 * | 9/2015 | Heaton ................ | A61M 1/882 604/313 |
| 2017/0015963 A1 | 1/2017 | Ott | |

FOREIGN PATENT DOCUMENTS

| | | |
|---|---|---|
| CN | 105494312 A | 4/2016 |
| EP | 1488743 A2 | 12/2004 |
| WO | 2015126853 A1 | 8/2015 |

OTHER PUBLICATIONS

Tane, et al., "Ex Vivo Lung Perfusion: A Key Tool for Translational Science in the Lungs", Chest, 2017, 151(6), pp. 1220-1228.
Charest, et al., "Design and validation of a Clinical-scale Bioreactor Long-term Isolated Lung Culture" Biomaterials, 2015, 52, pp. 79-87.
Popov et al., "Ex Vivo Lung Perfusion—State of the Art in Lung Donor Pool Expansion" Med. Sci. Monit. Basic Res., 2015, 19, pp. 9-14.
Wild et al., "PEEP and CPAP", British Journal of Anaesthesia, 2001, 1(3), pp. 89-92.
"The Secret of the Turtle", The Magazine of EBM-PAPST, 2018, retrieved Jan. 9, 2019 at <https://mag.ebmpapst.com/en/industries/medical/the-secret-of-the-turtle_2433/>.
K. Nelson et al., "Determination of Optimum Ventilation Strategy for Ex-Vivo Lung Perfusion: Comparing Negative and Positive Pressure Ventilation", The Journal of Heart and Lung Transplantation, vol. 34, No. 4, Apr. 1, 2015, p. S270, XP055659298A.
Extended European Search Report dated Jan. 28, 2020 in European patent application No. 17805438.3 (14 pages).
First Office Action dated Nov. 10, 2020 issued in Chinese patent application No. 201780032986.2 (4 pages).
Konstantinos Raymondos et al., "Combined Negative- and Positive-Pressure Ventilation for the Treatment of ARDS", Case Reports in Critical Care, vol. 2015, Article ID 714902, Jul. 31, 2015 (pp. 1-5).
Second Office Action dated Apr. 23, 2021 issued in Chinese patent application No. 201780032986.2 (17 pages).
Decision of Rejection dated Sep. 16, 2021 issued in Chinese patent application No. 201780032986.2 (18 pages).
Wang, Xiaolin et al.; "Mine rescue equipment operation and trauma first aid training demonstration materials", Feb. 2015; Beijing, ISBN 978-7-5020-4748-1 (55 pages).

* cited by examiner

APPARATUS AND METHOD FOR EX VIVO LUNG VENTILATION WITH A VARYING EXTERIOR PRESSURE

CROSS-REFERENCE TO RELATED APPLICATION

This application is a continuation application of U.S. patent application Ser. No. 16/305,648, filed Nov. 29, 2018, which application is a U.S. National Phase Application under 35 U.S.C. § 371 of International Application No. PCT/CA2017/050643, filed May 26, 2017, which claims the benefit of, and priority to U.S. Provisional Patent Application No. 62/343,076, filed May 30, 2016, the entire contents of each of the prior applications are incorporated herein by reference.

FIELD

This disclosure relates generally to devices and methods for lung ventilation, and particularly to devices and methods for ventilation of excised lungs by varying exterior pressures.

BACKGROUND

To use excised donor lungs for transplantation, the excised lungs may need to be perfused and ventilated ex vivo to restore or preserve their functionalities before the transplant procedure can be performed, or to assess or evaluate their quality or suitability for transplantation.

For ex vivo ventilation of excised lungs, the common traditional mechanical ventilation techniques employ a positive pressure applied to the tracheobronchial tree. This creates a pressure gradient between the tracheobronchial tree and the alveoli, such that airflow occurs down the pressure gradient into the alveoli.

It has been recognized that excised lungs can also be ventilated by a negative pressure ex vivo. For example, lungs may be ventilated utilizing a negative pressure (i.e., below atmospheric pressure) around the lungs to allow the lungs to naturally fill with ventilation gas that is at or near atmospheric pressure. Some authors have suggested that different strategies might be combined by supplying positive-pressure (above atmospheric pressure) ventilation gas to the lungs and utilizing a negative pressure around the lungs. However, these authors have not disclosed any specific details of effective strategies for utilizing positive and negative pressures to ventilate lungs ex vivo.

SUMMARY

An aspect of the present disclosure relates to a method of ventilating excised lungs. In this method, a ventilation gas is supplied to an airway of a lung and a vacuum is formed around the lung. A quality of the vacuum is varied between a lower level and a higher level to cause the lung to breathe, while the pressure of the ventilation gas supplied to the airway is regulated to maintain a positive airway pressure in the airway of the lung. The vacuum may be cyclically varied between the two vacuum levels. The levels may be maintained substantially constant over a period of time, or one or both of the lower and higher levels may be adjusted during ventilation. The lung may be placed in a sealed chamber, and a vacuum is formed in the chamber around the lung.

Conveniently, in some embodiments a single pump may be used to apply both the airway pressure and the vacuum around the lung.

In a modified embodiment, ventilation is effected by varying the exterior pressure (the pressure applied to the exterior surface of the lungs) between a higher pressure above the atmospheric pressure and a lower pressure below the atmospheric pressure. In other words, the lungs may be caused to breathe by varying the exterior pressure between a positive pressure and a vacuum pressure.

Another aspect of the present disclosure relates to a method of ventilating a lung, comprising applying a first pressure (P1) to an airway of the lung, and applying a second pressure (P2) to an exterior surface of the lung. The pressure differential, PD=P1−P2, is maintained positive and is varied to cause the lung to breathe.

In an embodiment, the airway pressure P1 is maintained higher than the atmospheric pressure, and the exterior pressure P2 is varied between a higher pressure level and a lower pressure level, where the lower pressure level is below the atmospheric pressure. In a particular embodiment, P1 may be maintained at a constant value, such as at a constant value from about 5 to about 10 cmH$_2$O. The pressure differential PD may be varied from about 7 to about 30 cmH$_2$O. For example, when P1 is constant at 5 cmH$_2$O, P2 may vary from −25 to −2 cmH$_2$O. When P1 is constant at 10 cmH$_2$O, P2 may vary from −20 to 3 cmH$_2$O.

In an embodiment, a regenerative vacuum pump, such as a regenerative turbine, may be used to apply and control both P1 and P2. P1 may be regulated using the exhaust pressure at the exhaust side of the pump, and P2 may be regulated using the vacuum pressure at the vacuum (intake) side of the pump. Conveniently, a single turbine may be sufficient to apply and control both P1 and P2.

A further aspect of the present disclosure relates to a method of ventilating a lung comprising applying an exterior pressure around a lung with a gas in fluid communication with a gas pump, and operating the gas pump to vary the exterior pressure around the lung to ventilate the lung. The gas pump may be a regenerative pump, such as a turbine pump. The gas around the lung may be confined in a constant volume but the amount of gas (e.g., moles of gas) in the constant volume is varied using the pump to change the exterior pressure applied to the lung.

In another aspect, a system for ventilating a lung is disclosed, which comprises a gas pump comprising an exhaust side and an intake side; a sealed chamber for enclosing the lung therein, and configured to apply a first pressure (P1) to an airway of the lung and apply a second pressure (P2) to an exterior surface of the lung enclosed therein; and a plurality of conduits and a plurality of valves, the conduits and valves connecting the gas pump to the sealed chamber for selectively regulating P1 and P2, wherein the proportional valves comprise a first proportional valve connected to the exhaust side of the gas pump, a second proportional valve connected to the intake side of the gas pump, and a third proportional valve connected to the first proportional valve, and wherein the conduits comprise a first conduit extending through the sealed chamber and connected to the third proportional valve, for connecting an airway of the lung to the gas pump through the third proportional valve and the first proportional valve to supply the pressure applied to the airway of the lung, a second conduit connecting the second proportional valve to the sealed chamber for supplying the pressure applied to the exterior surface of the lung, and a third conduit connecting the second conduit to the first proportional valve, such that P1 is regulated by the first proportional valve and the third proportional valve, P2 is regulated by the first proportional valve and the second proportional valve, and P1 and P2 are independently regulatable by controlling the first, second and third proportional valves.

In a further aspect, there is provided a lung ventilator comprising a container comprising a sealable chamber for housing a lung therein; a pump comprising an intake side and an exhaust side; a plurality of conduits connecting the pump to the sealable chamber for applying a first pressure (P1) to an airway of the lung and a second pressure (P2) to an exterior surface of the lung; and a control system comprising a controller, pressure sensors, flow sensors, and flow regulating valves, for controlling operation of the pump and regulating the pressures applied to the airway and the exterior surface of the lung, wherein the flow regulating valves comprise a plurality of proportional valves configured to regulate P1 using an exhaust pressure at the exhaust side of the pump, to regulate P2 using both the exhaust pressure and an intake pressure at the intake side of the pump, such that P1 and P2 are independently controllable by adjusting proportional valves.

Other aspects, features, and embodiments of the present disclosure will become apparent to those of ordinary skill in the art upon review of the following description of specific embodiments in conjunction with the accompanying figures.

BRIEF DESCRIPTION OF DRAWINGS

In the figures, which illustrate, by way of example only, embodiments of the present disclosure.

DETAILED DESCRIPTION

It has been recognized that, when excised lungs are ventilated ex vivo by varying a pressure around the lungs to cause the lungs to breathe, the lungs may still benefit from application of a regulated positive pressure into the airway to prevent alveolar collapse during expiration. For example, application of a positive airway pressure combined with oscillation of a pressure around the exterior of the lungs to drive breathing may allow the transpulmonary pressure gradient (TPG) in the lungs to be conveniently regulated to allow for effective recruitment of lung parenchymal alveolar segments, while reducing, minimizing or even preventing over distension of recruited segments.

Accordingly, an embodiment of the present disclosure relates to a method of ventilating excised lungs. In this method, a ventilation gas is supplied to an airway (e.g., the trachea or a bronchus) of a lung and a vacuum is formed around the lung. A quality of the vacuum is varied (e.g., cycled) between a lower level and a higher level to cause the lung to breathe, while the pressure of the ventilation gas supplied to the airway is regulated to maintain a positive airway pressure in the airway of the lung, where the airway pressure may be constant or continuously positive. Typically, the vacuum may be cyclically varied between the two vacuum levels. The levels may be maintained substantially constant over a period of time, or one or both of the lower and higher levels may be adjusted during ventilation. The ventilation gas may be filtered with a microbe filter and a humidity-moisture-exchanger (HME) filter before being supplied into the lung. The lung may be placed in a sealed chamber, and a vacuum is formed in the chamber around the lung.

Figure 1:
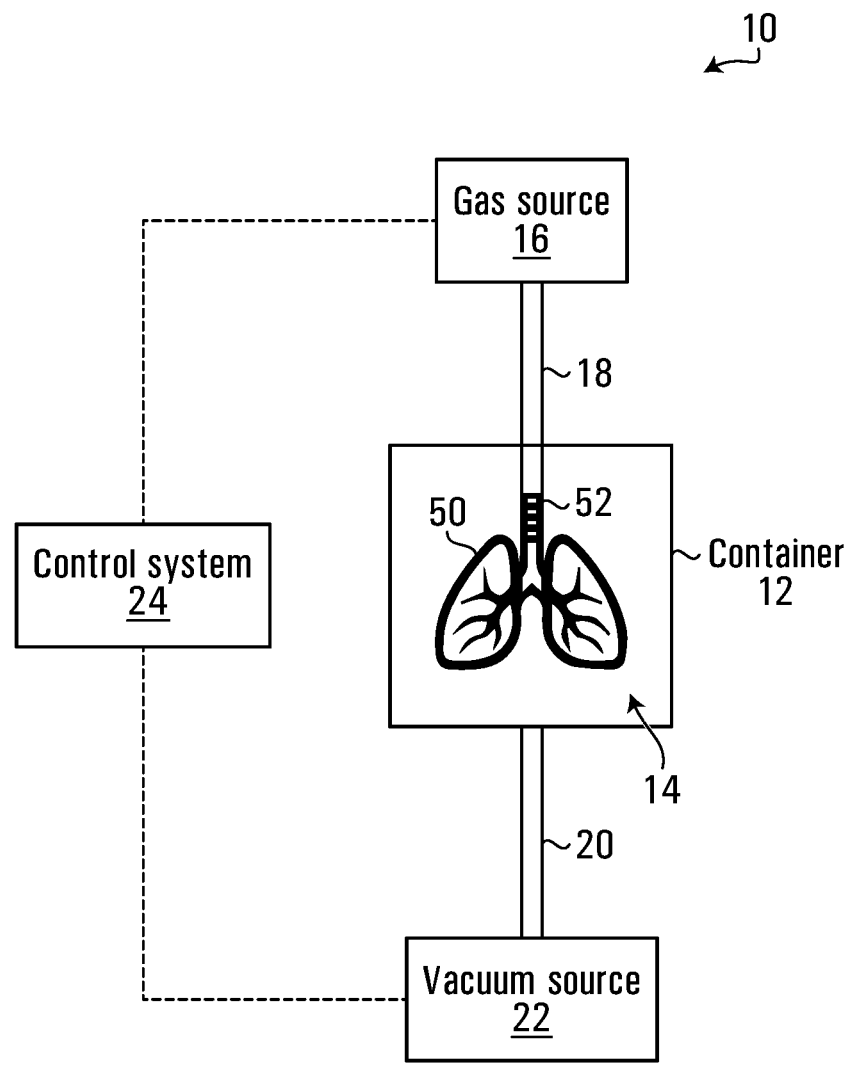
FIG. 1 is a schematic block diagram of an example apparatus for ventilating lungs.

An example apparatus 10 for ventilating excised lungs is schematically illustrated in FIG. 1.

As depicted, the apparatus 10 includes a container 12 having a sealable chamber 14 for housing a lung 50. For clarity, it is noted that the term "a lung" can refer to a single lung, multiple lungs, or a portion of a single lung or lungs. Two lungs attached to the same trachea are sometimes collectively referred to as "a lung" or "the lung" herein.

A ventilation gas source 16 is provided for supplying a ventilation gas at a variable positive pressure.

As used herein, a positive pressure refers to a pressure that is higher than the atmospheric pressure in the immediate environment of lung and the ventilation device, unless otherwise specified expressly.

A first conduit 18 extends through the wall of the container 12 and connects the ventilation gas source 16 to an airway 52 of the lung 50, for supplying the ventilation gas to the airway of the lung. The conduit 18 is sealed from pressure communication with the inner space in the chamber 14. As will be further described below, the ventilation gas may be air or any suitable gas mixture that contains oxygen. The ventilation gas source 16 may include the output port of an air pump or a motor-driven turbine (not shown in FIG. 1, but see FIG. 2) for supplying air to the lung at a positive pressure. The operation speed of the air pump or turbine may be controlled to regulate airway pressure in the lung.

A second conduit 20 connects a vacuum source 22 to the chamber 14 for forming a vacuum in the chamber 14. The same turbine used to supply the ventilation gas may be used to provide the vacuum source 22 (see e.g., FIG. 2).

A control system 24 is coupled to the ventilation gas source 16 and the vacuum source 22. As will be further described in more detail below, the control system 24 may include pressure sensors, flow sensors, flow-regulating valves, and one or more controllers (not shown in FIG. 1, but see FIG. 2), which are configured and adapted to vary a quality of the vacuum in chamber 14 between a lower vacuum level and a higher vacuum level to cause the lung 50 to breathe, and to regulate the pressure of the ventilation gas supplied by the ventilation gas source 16 to maintain a continuously positive airway pressure in the airway 52 of the lung 50.

Figure 2:
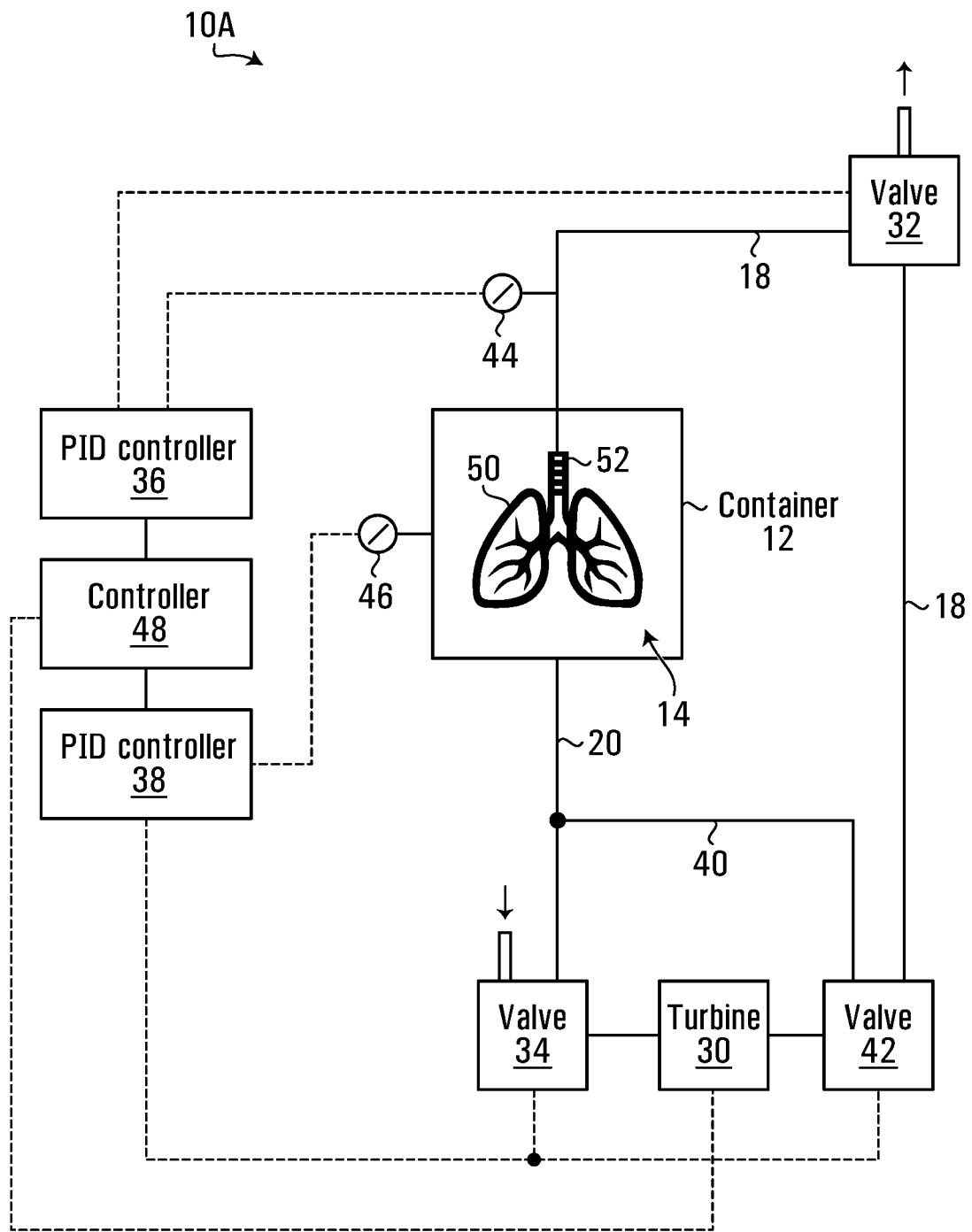
FIG. 2 is a schematic block diagram of an example implementation of the apparatus of FIG. 1.

For example, as illustrated in FIG. 2, which illustrates an example implementation 10A of the apparatus 10, a motor-driven turbine 30 may be used as the ventilation gas source 16 to supply air to the lung 50 from the output port of the turbine 30, and used as the vacuum source 22 to form and vary the vacuum in the chamber 14 by drawing or sucking air from the chamber 14 into the intake port of the turbine 30. In the example implementation 10A, the pressure in chamber 14 can also be positive (i.e., above atmospheric pressure) at selected times.

The control system 24 may include a first proportional valve 32 coupled to the conduit 18 for selectively releasing a portion of the air in the conduit 18 to the atmosphere (as indicated by the arrow above valve 32 in FIG. 2), and a second proportional valve 34 coupled to the conduit 20 for selectively adding air from the atmosphere into the conduit 20 (as indicated by the arrow above valve 34 in FIG. 2). As can be appreciated, in a different embodiment if a different ventilation gas source may be used to replace air in the atmosphere.

The control system 24 may also include a first proportional-integral-derivative (PID) controller 36 for controlling the operation of the first proportional valve 32, and a second PID controller 38 for controlling the operation of the second proportional valve 34.

A third conduit 40 may be provided to interconnect conduits 18 and 20, and a third proportional valve 42 may be connected to the output port of the turbine 30 and coupled to the conduits 18 and 40 for selectively feeding air from the output port of the turbine 30 into the conduits 18 and 40 in different proportions. The second PID controller 38 may also be connected to control the operation of the third proportional valve 42.

The control system 24 may further include a first pressure sensor 44 for sensing a first pressure in the first conduit 18, and a second pressure sensor 46 for sensing a second pressure in the chamber 14. The first pressure sensor 44 is connected to provide an input to the first PID controller 36, and the second pressure sensor 46 is connected to provide an input to the second PID controller 38.

The control system 24 may further include a central processing unit or a controller 48 in electrical communication with the PID controllers 36 and 38 and the turbine 30, for controlling the operation of the PID controllers 36 and 38 and the operation of the turbine 30. The controller 48 may be a microprocessor, and may be provided in the form of a computer (see e.g., FIG. 7).

While not shown in FIGS. 1 and 2, one or more microbe and HME filters (see e.g., FIG. 3) may be coupled to one or more of conduits 18 and 20 for filtering and humidifying the air to be supplied into the chamber 14 and the airway 52 of the lung 50.

Embodiments of the method and apparatus described herein may be conveniently used for negative pressure ventilation in an ex vivo lung perfusion (EVLP) process or system. Application of positive pressure into the airway of the lung, when combined with such negative pressure ventilation, allows a higher TPG to be achieved without applying excessively negative pressure to the exterior of the lung.

Embodiments disclosed herein may also allow for recovery of atelectatic alveoli, thereby facilitating extended EVLP. It is further convenient to use at least some disclosed embodiments to measure and obtain functional attributes of the ventilated lungs ex vivo.

A single suitable turbine can generate a sufficient pressure gradient and airflow to meet the requirements for ventilating lungs with a variety of sizes. A single turbine can provide both a source of vacuum (e.g., for applying a negative pressure to the exterior of a lung) and a source of positive pressure (e.g., for applying a positive pressure to the airway of the same lung, and optionally applying a positive pressure to the exterior of the lung). Thus, in an embodiment disclosed herein a single turbine may be sufficient to drive the air flows in the ventilation system. A benefit of such an embodiment is that it is energy efficient, as the same energy used to generate the vacuum is also used to generate the positive pressure. Another benefit of such an embodiment is its relative simple construction and small footprint.

Figure 3:
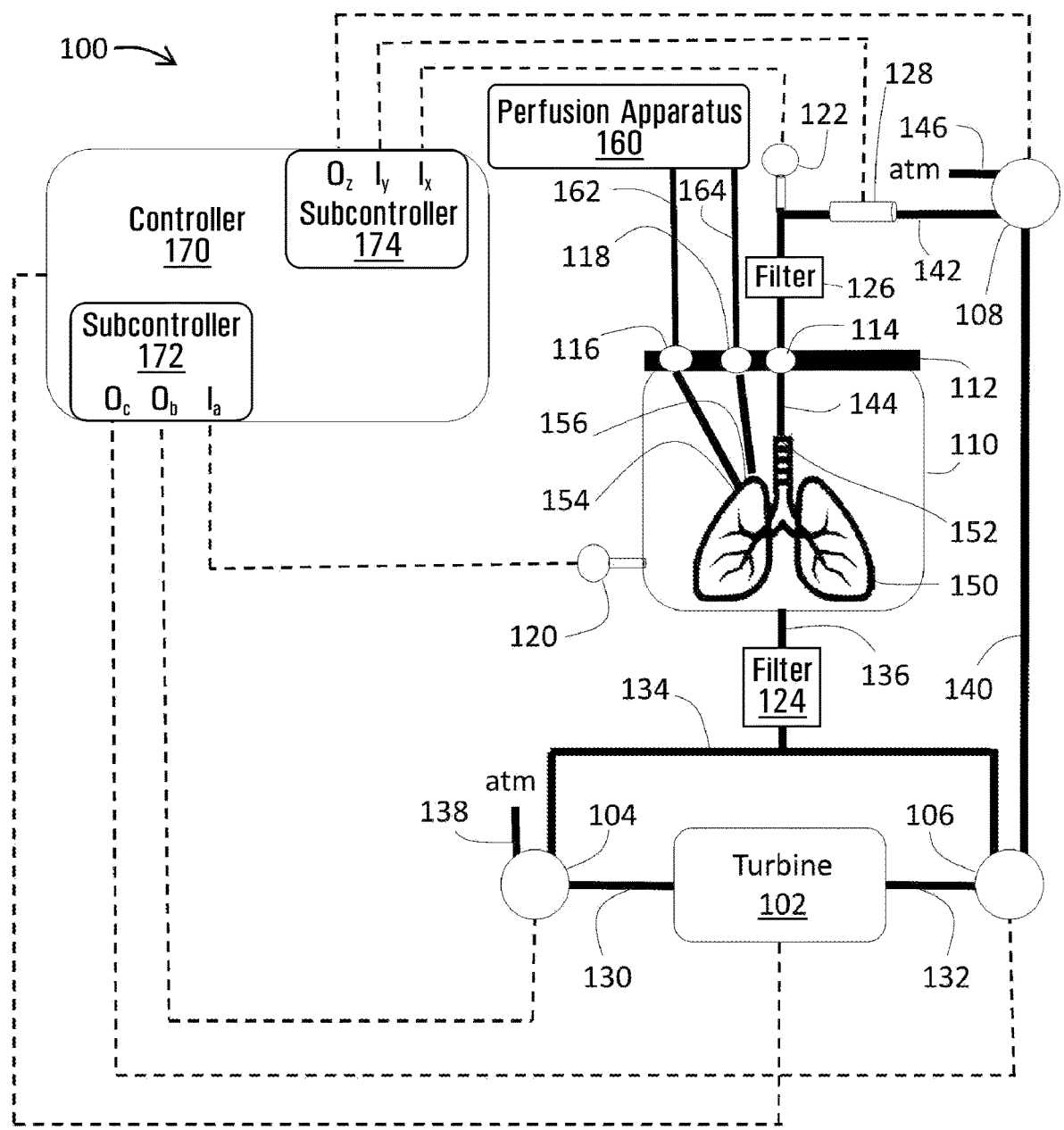
FIG. 3 is a schematic block diagram of another example apparatus for ventilating lungs.

In a further embodiment, a combined ventilation and perfusion apparatus 100 may be constructed as illustrated in FIG. 3.

As depicted, donor lungs 150 are placed inside a rigid or pressure-resistant container 110. Within the container 110, the lung may be supported on a flexible porous surface, such as a silicone or plastic net, or the lung may be rendered buoyant through placement on a fluid surface covered with a soft plastic membrane (not shown). Alternatively, the lung may be supported on a semi-rigid plastic form that resembles the shape of the posterior chest such that the lungs lie in an anatomically familiar position (not shown).

A perfusion apparatus 160 is provided to perfuse the lungs 150. A conduit 162 connected to the perfusion apparatus 160 is also connected, optionally with a cannula, to a pulmonary artery 154 of the lungs 150. A conduit 164 connected to the perfusion apparatus 160 is also connected with a pulmonary vein 156, possibly through attachment to the left atrium and optionally with a cannula, of the lungs 150. Through conduits 162 and 164, the perfusion apparatus 160 can be configured to circulate a perfusate through the vasculature of the lungs 150 in a manner known to those skilled in the art.

The tracheobronchial tree 152 of the lungs 150 is connected to a conduit 142 by an endotracheal tube 144. As will be apparent to a person of skill in the art, when a single lung or a portion of a single lung is mounted in the apparatus, an endotracheal tube or analogous device can be inserted into either the trachea attached to the lung (or lung portion) or inserted directly into a bronchus of the lung (or lung portion). In such instances, a pediatric endotracheal tube may be the appropriate size to connect to a bronchus.

The container 110 is sealed with a lid 112 to isolate the inner space in container 110 from the atmosphere. The conduit 142 (or the endotracheal tube 144) passes through the lid 112 via a port 114. The conduit 162 passes through the lid 112 via a port 116. The conduit 164 passes through the lid 112 via a port 118. When the conduits 162, 164 and 142 (or the endotracheal tube 144) are installed in place, all of the ports 114, 116 and 118 are sealed to the atmosphere. As a result, the inner space in the container 110 is isolated from the atmosphere, and the pressure exerted on the exterior surfaces of the lungs 150 is not dependent on the atmospheric pressure and can be independently controlled and regulated.

A conduit 136 connects the container 110 to a conduit 134. The gas pressure inside the container 110 is dependent on the pressure inside the conduit 136, and the pressure in the conduit 134. The conduit 134 is connected to proportioning valves 104 and 106, which are in turn connected to the intake port and output port of a turbine 102 by conduits 130 and 132 respectively.

The valve 104 has an open inlet 138 that allows atmospheric air to enter the valve 104, and can be operated to allow selected proportions of air from the atmosphere ("atm") and the conduit 134 to enter the conduit 130.

The valve 106 is coupled to the conduits 132, 134 and 140, and is operable to allow selected proportions of air from the conduit 132 to enter either the conduit 134 or the conduit 140.

As can be appreciated, the turbine 102 outputs a positive pressure at the output port connected to the conduit 132, and forms a negative pressure at the intake port connected to the conduit 130.

The atmospheric air may be filtered for microbes and other particles before passage through the valve 104 by a filter (not shown).

Optionally, a source of a gas mixture (e.g., oxygen/air) at-or-around atmospheric pressure may be connected to inlet 138 of the valve 104, to supply a ventilation gas in place of atmospheric air, so as to expose the lungs to a desired or controlled gas mixture.

In the example apparatus in FIG. 3, the rotational speed of the turbine 102 may be varied to control the air pressure applied at the output port of the turbine 102, although it is also possible to operate turbine 102 at a constant speed over a period of time if desired. As can be appreciated, when turbine 102 is in normal operation the air pressure inside the conduit 130 is a negative pressure (i.e., lower than the atmospheric pressure), and the air pressure inside the conduit 132 is a positive pressure (i.e., higher than the atmospheric pressure).

The valves 104 and 106 can be controlled, such as by a controller 170 particularly a subcontroller 172 in the controller 170, to regulate the pressure in the conduits 134 and 136, and consequently the pressure in the inner space of the container 110 to form a vacuum in the container 110 around the lungs 150. The valves 104 and 106 can be controlled to oscillate the pressure inside the container 110 between a lower (vacuum) pressure and a higher (vacuum or positive) pressure, which will cause the lungs to breathe (i.e., taking in and expelling out air through the endotracheal tube 144). It should be understood that the term "vacuum" as used herein refers to partial vacuum, and the quality of the vacuum refers to how closely the vacuum approaches a perfect vacuum. In other words, the quality of the vacuum is related to the vacuum pressure, and how close the vacuum pressure approaches absolute zero. The variation in the air pressure in the container 110 causes the lungs 150 to correspondingly expand or contract. The lungs may contract even when the airway pressure in the endotracheal tube 144 is higher than the instant air pressure in the container 110, as long as the pressure differential is not too high so that the pressure differential can be overcome by the elastic recoil of the lungs. Expansion and contraction of the lungs 150 can be controlled to mimic or simulate the expansion and contraction of in vivo lungs during normal breathing, and to move air into and out of the alveoli through the endotracheal tube 144. With the controllers as described, the apparatus 100 allows precise control and regulation of the pressures and the rates of pressure change in both the container 110 and in the endotracheal tube 144, and the waveforms or profile of the pressure oscillation can be conveniently set and varied by a user, such as using a computer 200.

The turbine 102 can be used to generate a basal level of airflow through the system, which generates a pressure gradient. The pressure gradient between the tracheobronchial tree and the serosal surface of the lungs may be varied by adjusting the proportioning valves 104, 106 and 108 to vary the TPG such that the lungs cyclically inhale and exhale. The turbine speed may be varied only when needed to ensure the pressure gradient is sufficient throughout the each ventilation cycle.

Although not necessary for negative pressure ventilation, as noted above, maintaining a positive airway pressure in the endotracheal tube 144 can provide certain benefits and advantages. In this regard, the conduit 140 is connected to the conduit 142 through a third proportioning valve 108, which has an open outlet 146. The valve 108 is operable to supply a selected portion of air from the conduit 140 into the conduit 142, and the remaining portion of air is released into the atmosphere (atm) through the outlet 146. As can be appreciated, in different embodiments when a ventilation gas other than atmospheric air is used, outlet 146 may be connected to the source of the ventilation gas to recycle or circulate the ventilation gas back to the source.

As one example, positive airway pressure can be achieved during ex vivo ventilation by applying a continuous or constant positive pressure into the airway, such as in a similar manner as the airway pressures applied in a treatment technique known as continuous positive airway pressure ("CPAP") in the treatment of some human disorders (e.g., obstructive sleep apnea). For clarity, the terms "continuous" and "continuously" as used herein are not synonymous with the term "constant".

The valve 108 is controlled by the controller 170, particularly the subcontroller 174 in the controller 170, to regulate the pressure and flow rate in the conduit 142, and consequently the airway pressure in endotracheal tube 144. The valve 108 may also allow air in the conduit 142 be released into the atmosphere when the lungs 150 are caused by the higher pressure in the container 110 to expel air from the lungs 150. The valve 108 may be controlled to maintain the desired airway pressure, where the desired pressure may be set by the user to be in the range of atmospheric pressure up to an upper limit (e.g., 10 cmH$_2$O).

To avoid desiccation of the lungs 150, a HME filter 124 can be coupled to the conduit 136, and a HME filter 126 can be coupled to the conduit 142. Optionally, microbe filters can also be coupled to the conduits 136 and 142 (not shown).

As alluded to earlier, the operation of the valves 104, 106, and 108 is controlled by a controller 170, based on signals received from a pressure sensor 122 coupled to the conduit 142, which detects a pressure signal that is indicative of the airway pressure (P$_{AW}$) in the lungs 150 and a pressure sensor 120 coupled to the container 110 for detecting a signal indicative of the pressure in the container 110 (referred to as the "intrathoracic" pressure or P$_{IT}$ or ITP). One form the controller 170 may take is a computer 200 (not shown in FIG. 3).

The controller 170 may also be connected to a flow sensor 128 that detects a signal indicative of the air flow rate in the endotracheal tube 144. Optionally, the valves 104, 106, and 108 may be operated based in part on the signal received from the flow sensor 128.

The rotational speed of the turbine 102 may be controlled by the controller 170 or the computer 200 based on the detected signals and one or more parameters set by a user.

The user set-points for the controller 170 or the computer 200 may include the end inspiratory pressure (EIP) in the container 110, the end expiratory pressure (EEP) in the container 110, the inspiratory time (T$_i$), the expiratory time (T$_e$), the tidal volume (V$_t$), and the airway pressure (P$_{AW}$). As will be apparent to a person of skill, when ventilation is effected by varying an exterior pressure around the lungs, EIP and EEP refer to the pressure levels of the exterior pressure (e.g., the pressure inside container 14 in FIGS. 1-2 or container 110 in FIGS. 3-5), which pressure is also referred to herein as the "intrathoracic" pressure (abbreviated as P$_{IT}$ or ITP). By contrast, in traditional mechanical ventilation techniques in which a varying positive pressure is applied into the airway to cause ventilation, EIP and EEP are usually measures of the levels of the airway pressure at different points in a ventilation cycle.

The controller 170 or the computer 200 may use intrathoracic air pressure (P$_{IT}$), airway pressure (P$_{AW}$) and endotracheal tube airflow (V) as inputs. The controller 170 or the computer 200 may output control signals for controlling the three proportional valves 104, 106, and 108 and the motor or turbine speed (e.g., in terms of rotations per minute) of the turbine 102.

As can be appreciated, the controller 170 and the computer 200 may receive additional inputs from other components shown or not shown in the figures, and may be used to control additional components of the apparatus 100. For example, a temperature sensor (not shown) and a temperature control device (not shown) may be used and connected to the computer 200 or the controller 170 to control the temperature in container 110. In addition, the computer 200 or the controller 170 may be used to control the flow of perfusate through the pulmonary vasculature.

The dotted or dashed lines in the figures (such as FIGS. 1, 2 and 3) indicate communication connections, which may be electrical or otherwise, and may be wired connections or wireless connections as can be understood by those skilled in the art.

The controller 170 may include one or more proportional-integral-derivative (PID) controllers, although two PID subcontrollers 172 and 174 are depicted in FIG. 3.

In the particular example embodiment depicted in FIG. 3, the PID subcontroller 172 in the controller 170 uses the pressure in the container 110 (detected by the pressure sensor 120) as an input (I$_a$), and outputs a signal (O$_b$, O$_c$) for controlling the proportional valves 104 and 106. The PID subcontroller 174 in the controller 170 uses the airway pressure (I$_x$) detected by the pressure sensor 122 (and optionally the endotracheal air flow rate (I$_y$) measured by the flow sensor 128) as an input, and outputs a signal (O$_z$) for controlling the proportional valve 108.

The turbine 102 is optionally connected to and controlled by the computer 200 or the controller 170.

The controller 170 may be configured by a user with different user-selected parameter settings or different series of parameter settings (e.g., desired container pressures over time), which may be entered by a user into the controller 170 using a user interface such as a graphical user interface (GUI) (not shown), or may be loaded from a configuration file stored in a computer memory. The parameter settings may include set-point values for one or more PIDs in the controller 170.

For example, a positive airway pressure may be maintained in the tracheobronchial tree 152 by properly setting the parameter for the PID subcontroller 174 set-point values to control the endotracheal tube flow and airway pressure. These set-point values may or may not change over time.

Conveniently, an apparatus disclosed herein such as apparatus 100 can also be used to measure and store functional attributes of the lungs 150, such as the flow-volume profile or pressure-volume profile for a pair of ventilated lungs. The volume may be measured or calculated based on airflow as detected by flow sensor 128. Other functional attributes that can be measured with the apparatuses and methods of the disclosure include dynamic compliance, elastance, and airway resistance.

Examples of suitable turbines include a turbine used in the Philips Respironics Duet LX™ CPAP Pro machines, and may include other known turbines that are suitable for use in conventional CPAP treatment of intact lungs (such as those disclosed in EP 1488743 published Dec. 22, 2004 or U.S. Pat. No. 6,526,974 to Brydon et al. published Mar. 4, 2003).

Other example turbines are described at the following URLs:

http://mag.ebmpapst.com/en/industries/medical/the-secret-of-the-turtle_2433/ https://www.bedek.de/en/blowers-and-fans-in-medical-filed.html http://www.micronel.com/products/micronel-inside-medical/

Suitable examples of proportioning valves include those used in Philips™ Respironics BiPAP machines, and may include those with a voicecoil actuator.

Any suitable microbe filters, such as high-efficiency particulate arresting (HEPA) filters, and HME filters known to those skilled in the art may be used in an embodiment herein. There are products on the market that have both HME and HEPA properties.

Figure 4:
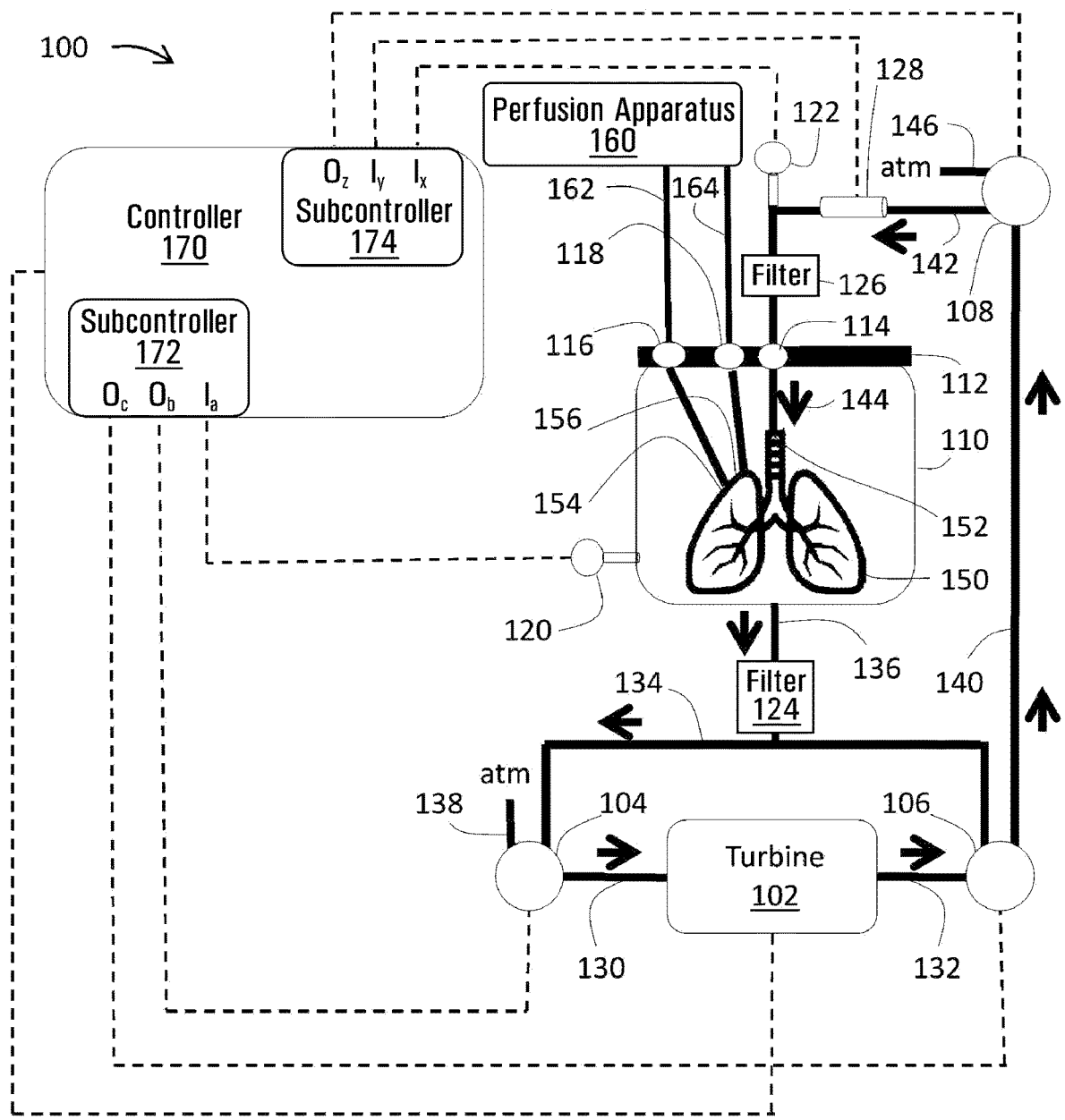
FIG. 4 is a schematic diagram of the apparatus of FIG. 3, showing air flow during inspiration.

FIG. 4 illustrates the air flow in apparatus 100 during inspiration. The arrows alongside conduits indicate the direction of airflow. The valves are configured such that air flows from inside the container 110, into the conduit 136, and then into the conduit 134 before moving through the turbine 102. In this manner, the pressure inside the container 110 is decreased and negative pressure is applied to the exterior of the lungs 150. The air flows from the turbine outlet, into the conduit 132, through the valve 106, into the conduit 140, through the valve 108, and into the conduit 142 and the endotracheal tube 144. In this manner, a positive pressure is applied to the airway 152 of the lungs 150. The combination of negative and positive pressure results in a pressure gradient from the tracheobronchial tree to the alveoli, such that airflow occurs down the pressure gradient into the alveoli.

Figure 5:
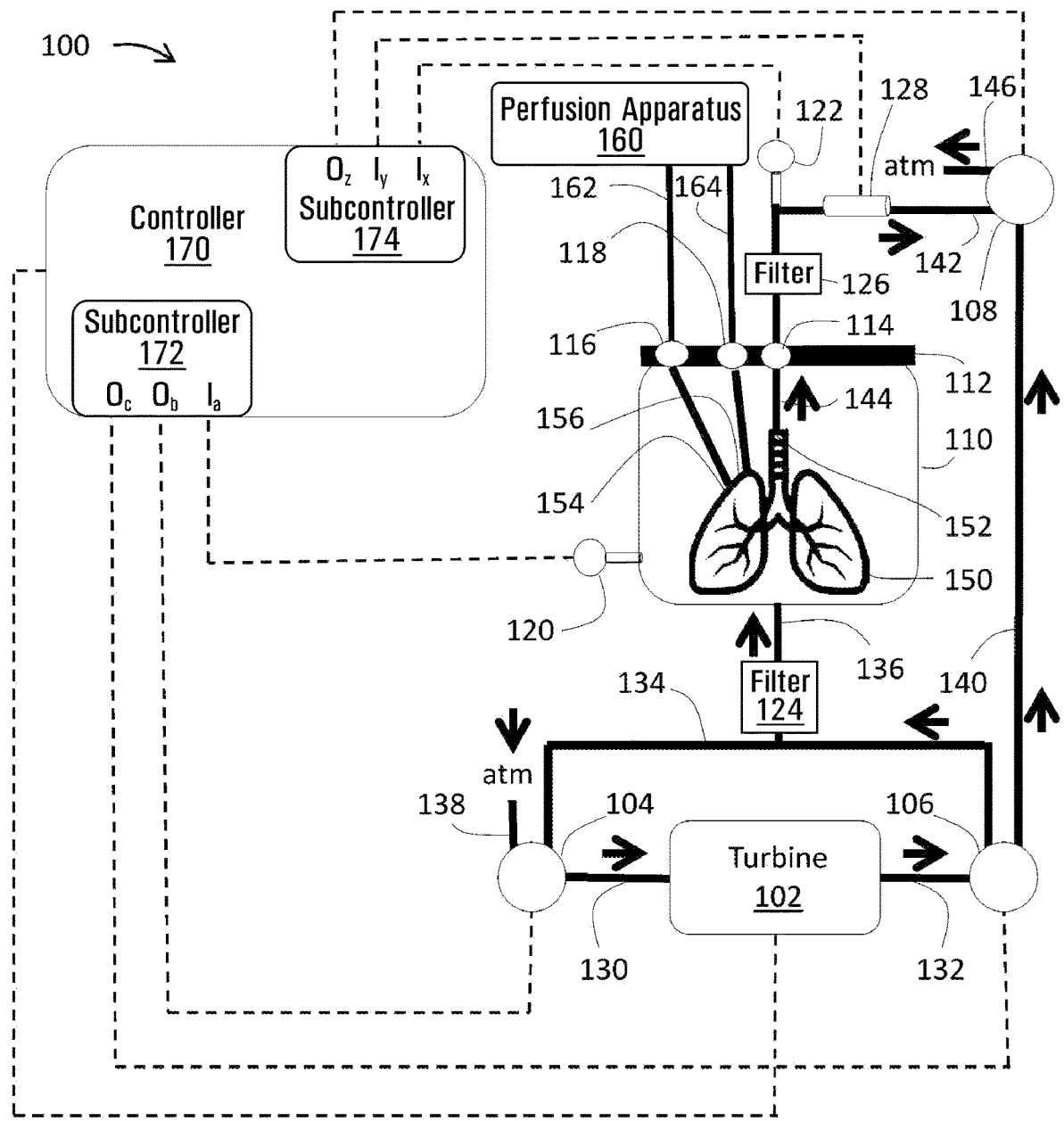
FIG. 5 is a schematic diagram of the apparatus of FIG. 3, showing air flow during expiration.

FIG. 5 illustrates the air flow in the apparatus 100 during expiration. The valves are configured such that air flows from the inlet 138, through the valve 104, into the conduit 130, through the turbine 102, and into the conduit 132. As the valve 106 is open, at an appropriate proportion, to both the conduit 134 and the conduit 140, air flows into the chamber 110 and toward the valve 108. Increasing the pressure inside the chamber 110, when combined with the elastic recoil of the lungs, results in a pressure gradient from the alveoli to the tracheobronchial tree, such that airflow occurs down the pressure gradient into the tracheobronchial tree 152, out of the endotracheal tube 144, into the conduit 142, and then into the proportioning valve 108, from which the expired air exits the apparatus through the outlet 146. The valve 108 appropriately proportions the airflow from the conduit 140 into the conduit 142 and the outlet 146 such that the positive pressure into the endotracheal tube 144 does not impede expiration.

Figure 6:
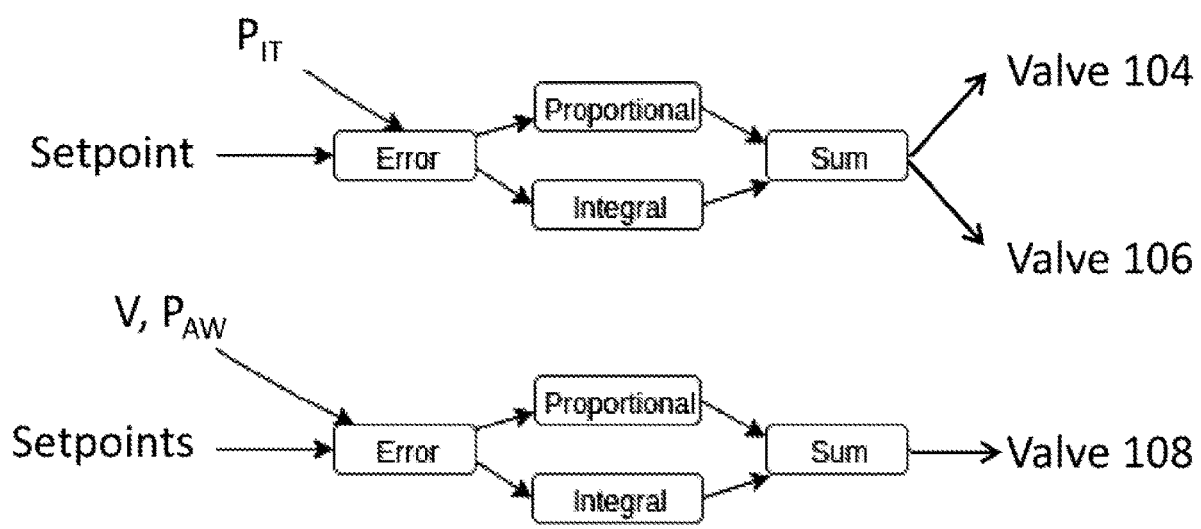
FIG. 6 is a schematic diagram illustrating the control logic used to control the proportional valves in the apparatus of FIG. 3.

FIG. 6 illustrates the control logic for controlling the valves 104, 106, and 108. The control may be implemented using a proportional-integral-derivative (PID) controller, although the PID controller may be used to provide P-I control, P-D control, P control or I control. As can be understood by persons skilled in the art, a PID controller can continuously calculate an error value as the difference between a desired set-point and a measured variable or multiple detected variables. A PID controller can attempt to minimize the error value or a composite of multiple error values over time by adjustment of a controlled variable. The set-points are entered by the user, either manually or by loading set-points from a memory device. The top PI control logic in FIG. 6, which is provided by subcontroller 172 in FIG. 3, is used to control proportional openings of valves 104 and 106. In this logic, the detected pressure inside the container 110 housing the lungs 150 (the "intrathoracic pressure" or $P_{IT}$) is compared to a set-point of the desired $P_{IT}$, and the difference between the actual $P_{IT}$ and the set point is used as feedback for adjusting the valve 104 and the valve 106. The bottom PI control logic, which is provided by subcontroller 174 in FIG. 3, is used to control proportional opening of valve 108. In this logic, the detected pressure inside the airway of the lungs ($P_{AW}$) and the measured or calculated endotracheal tube airflow (V) are compared to their respective set-points, and the respective errors are used for adjusting the proportioning in the valve 108.

Figure 7:
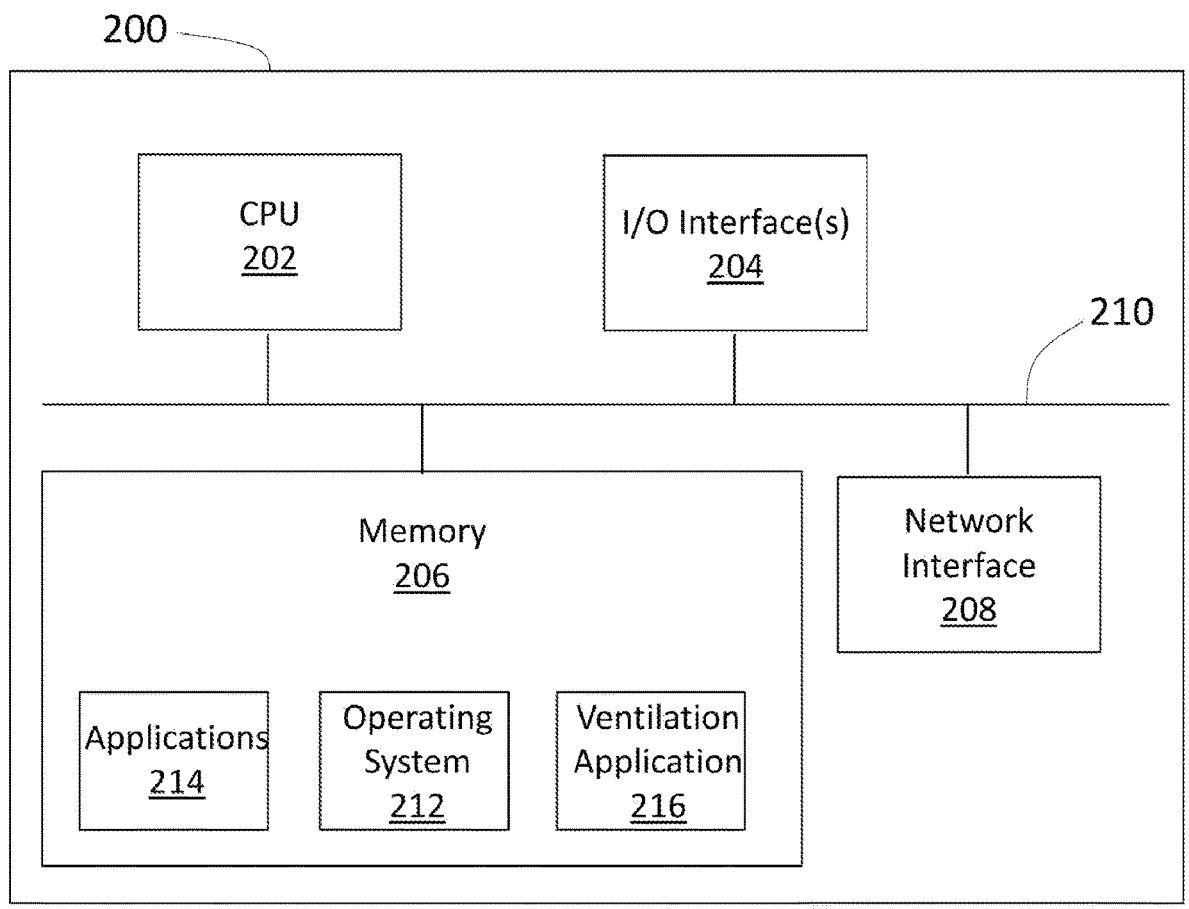
FIG. 7 is a block diagram of a computer for use with the apparatus of FIG. 1 or 3.

FIG. 7 is a high-level block diagram of the computing device 200, which can be used in combination with other controllers or in place of the controller 170. The computing device 200 may include or be part of a portable computing device (e.g., a mobile phone, netbook, laptop, personal data assistant (PDA), or tablet device) or a stationary computer (e.g., a desktop computer, or set-top box). As will become apparent, the computing device 200 includes software that allows a user to control and monitor an ex vivo lung ventilation apparatus, such as the apparatus 100 in FIG. 3. As illustrated, the computing device 200 includes one or more processors 202, a memory 206, a network interface 208 and one or more I/O interfaces 204 in communication over a bus 210. One or more processors 202 may be one or more INTEL™ x86, INTEL™ x64, AMD™ x86-64, POWERPC™, ARM™ processors or the like. The memory 206 may include random-access memory, read-only memory, or persistent storage such as a hard disk, a solid-state drive or the like. Read-only memory or persistent storage is a computer-readable medium. A computer-readable medium may be organized using a file system, controlled and administered by an operating system governing overall operation of the computing device. The network interface 208 serves as a communication device to interconnect the computing device 200 with one or more computer networks such as, for example, a local area network (LAN) or the Internet. The network interface 208 may be configured to enable the computing device 200 to communicate with external devices via one or more networks. The network interface 208 may be a network interface card, such as an Ethernet card, an optical transceiver, a radio frequency transceiver, or any other type of device that can send and receive information. One or more I/O interfaces 204 may serve to interconnect the computing device 200 with peripheral devices, such as, for example, keyboards, mice, video displays, and the like (not shown). Optionally, the network interface 208 may be accessed via one or more I/O interfaces 204. One or more I/O interfaces 204 may serve to collect information from and control components of the apparatus of the disclosure, of which the apparatus 100 in FIG. 3 is an example. For instance, an I/O interface 204 may communicate by wire or wirelessly with valves, pressure sensors, a flow sensor, and a turbine. The I/O interfaces 204 may be configured to receive input from a user. Input from a user may be generated as part of a user running one or more software applications.

Software comprising instructions is executed by one or more processors 202 from a computer-readable medium. For example, software may be loaded into random-access memory from persistent storage of the memory 206 or from one or more devices via I/O interfaces 204 for execution by one or more processors 202. As another example, software may be loaded and executed by one or more processors 202 directly from read-only memory.

The memory 206 stores an operating system 212, applications 214, and a ventilation application 216. The operating system 212 may be configured to facilitate the interaction of applications, such as an application 214 and a ventilation application 216, with processor(s) 202, memory 206, I/O interfaces 204, and the network interface 208 of the computing device 200.

The operating system 212 may be an operating system designed to be installed on laptops and desktops. For example, the operating system 212 may be a Windows operating system, Linux, or Mac OS. In another example, if the computing device 200 is a mobile device, such as a smartphone or a tablet, the operating system 212 may be one of Android, iOS or a Windows mobile operating system.

The applications 214 may be any applications implemented within or executed by the computing device 200 and may be implemented or contained within, operable by, executed by, and/or be operatively/communicatively coupled to components of the computing device 200. The applications 214 may include instructions that may cause the processor(s) 202 of the computing device 200 to perform particular functions. The applications 214 may include algorithms which are expressed in computer programming statements, such as, for loops, while-loops, if-statements, do-loops, etc. Applications may be developed using a programming language. Examples of programming languages include Hypertext Markup Language (HTML), Dynamic HTML, Extensible Markup Language (XML), Extensible Stylesheet Language (XSL), Document Style Semantics and Specification Language (DSSSL), Cascading Style Sheets (CSS), Synchronized Multimedia Integration Language (SMIL), Wireless Markup Language (WML), Java™, Jini™, C, C++, Perl, Python, UNIX Shell, Visual Basic or Visual Basic Script, Virtual Reality Markup Language (VRML), ColdFusion™ and other compilers, assemblers, and interpreters.

The ventilation application 216 is an example of an application configured to ventilate lungs ex vivo according to the techniques described herein. As described above, the controller 170 or the computing device 200 may include GUIs that enable a user to monitor and/or control one or more ventilation parameters (e.g., $P_{IT}$). The ventilation application 216 may be configured to enable a user to monitor and/or control ventilation parameters using one or more GUIs.

It should be noted that although the example computing device 200 is illustrated as having distinct functional blocks, such an illustration is for descriptive purposes and does not limit the computing device 200 to a particular hardware architecture. Functions of the computing device 200 may be realized using any combination of hardware, firmware and/or software implementations.

Figure 8:
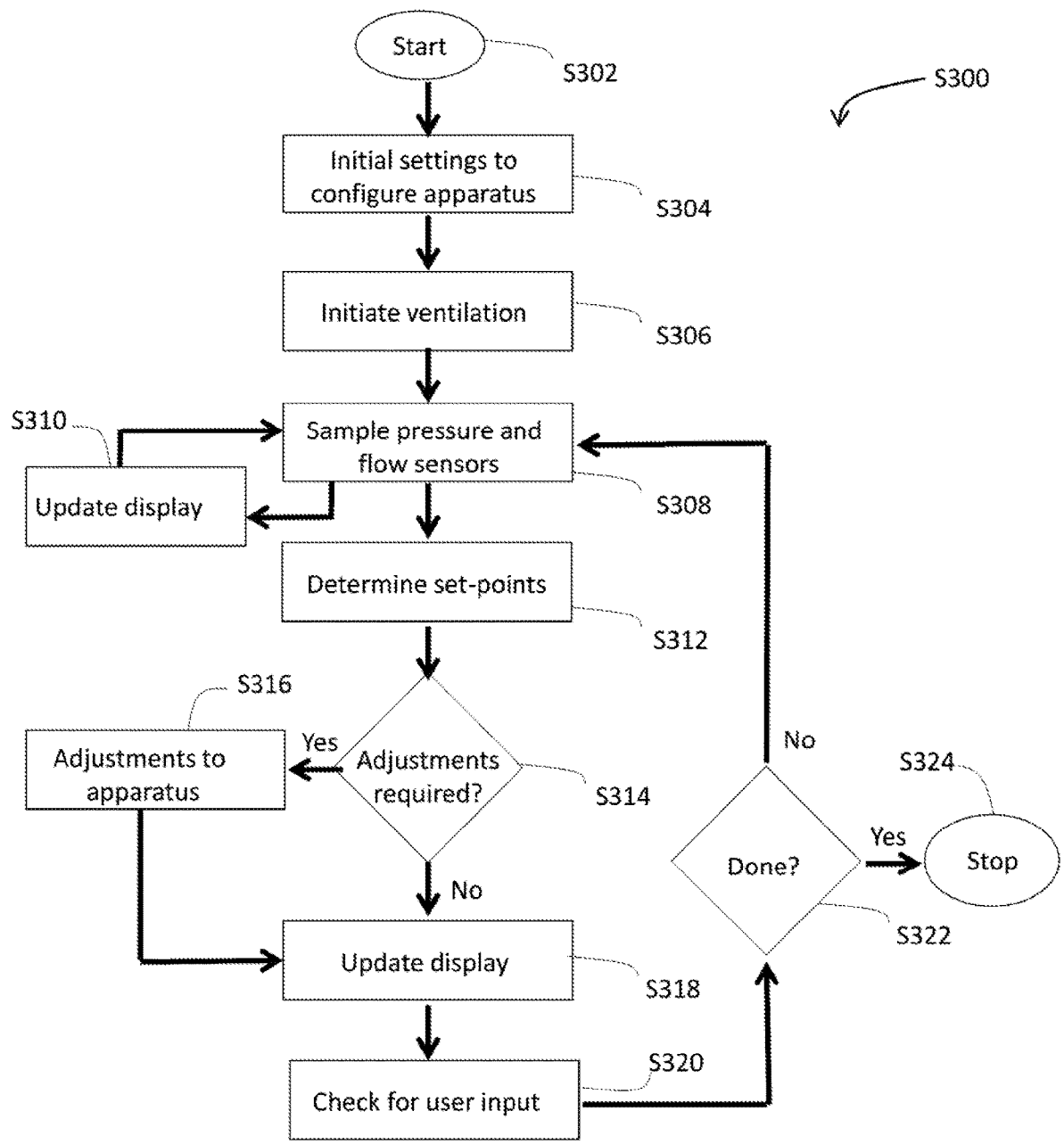
FIG. 8 is a flow chart illustrating an algorithm executed by the computer device of FIG. 7 for controlling operation of the apparatus of FIG. 3.

FIG. 8 is a flow chart of an algorithm S300 that can be executed by one or more processors 202 to monitor and control an apparatus of the disclosure, such as the apparatus 100 in FIG. 3.

The software is initiated by a signal provided by a user or automated process at block S302. At block S304, one or more processors 202 receive initial settings to configure the apparatus 100.

At block S306, one or more processors 202 communicates with one or more I/O interfaces 204 to initiate control of the apparatus 100 once the lungs 150 are attached and the container 110 sealed.

At block S308, one or more processors 202 communicates with one or more I/O interfaces 204 to receive information (e.g., $P_{IT}$, $P_{AW}$, V) from sensors in the apparatus 100. Some or all of this information from the sensors is displayed at block S310, and the display may be continually or periodically updated with information received from the sensors. At block S312, the software determines the desired set-points at that moment in time, as entered by a user, either manually or by being placed into the memory 206 (e.g., by loading a configuration file). The set-points may change with the time in order to cause the pressure oscillations that cause the lung to breathe ex vivo. The software then determines at block S314 whether adjustments are required. If so, at block S316 adjustments are made to components of the apparatus 100 (e.g., to the valves 104 and 106 to alter $P_{IT}$). Block S314 and block S316 may include PID calculations, as discussed with respect to FIGS. 3 and 6.

At block S318, the status of the apparatus 100 is communicated to the user by updating the display, and at block S320 the software checks for user input (e.g., to change set-points). At block S322, it is determined whether ventilation is done, either according to predetermined settings or through live interfacing with a user. If ventilation is not done, the software returns to block S308 to again sample sensors.

If ventilation is done, at block S322, it is determined whether the operation settings should be reconfigured, such as by loading a new configuration file. Reconfiguration may be required when a different mode of operation is desired. If the settings are to be reconfigured, the software returns to block S304 to receive new initial settings (not shown). If the settings are not to be reconfigured, ventilation is stopped at block S324.

Another aspect of software S300 may be the recording of information from sensors in the apparatus and adjustments S316 made by the software. This information may be stored in the memory 206.

An embodiment of the present disclosure can provide improved performance.

For example, it is noted that when a positive pressure is applied to the airway in the lung ex vivo and there is a pressure gradient from the tracheobronchial tree to the alveoli, if there is a large discrepancy between the surface tension of the alveolar group, the high pressure in the tracheobronchial tree preferentially goes to alveoli with lower distending pressure, which may result in over-distension of those alveoli, whereas alveoli with higher distending pressure are not ventilated. This can lead to over-distension of healthy alveoli, with incomplete recovery of atelectatic (collapsed alveoli with high surface tension) lung segments. As alveoli rupture from high pressure that is given in attempts to recover atelectatic alveoli, bullae can form on the surface of the lung and subsequently rupture causing air leak and further injury to the lung.

It is also noted that lungs are naturally ventilated in vivo in the body through an increase in negative pressure to the serosal surface of the lungs. Two layers of serous membrane enclose each lung; the parietal pleura line the wall of the thoracic cavity and the visceral pleura covers the lung. The pleural cavity between the two pleurae contains a small amount of lubricating fluid. During normal breathing, the pressure in the pleural cavity, called intrathoracic pressure, is always subatmospheric. During inspiration, muscle contraction increases the overall size of the thoracic cavity, decreasing intrathoracic pressure. This negative pressure is transmitted throughout the lung parenchyma and alveolar network, which creates a pressure gradient from the tracheobronchial tree to the alveoli. As a consequence, air flows into the alveoli during inspiration. During normal expiration in vivo, the muscles of inspiration relax. Expiration results from elastic recoil of the chest wall and lungs, with much of the inward pull caused by the surface tension in the film of alveolar fluid. This elastic recoil creates a pressure gradient from the alveoli to the tracheobronchial tree, such that air flows out of the alveoli. During forceful expiration in vivo, muscles of expiration contract, actively increasing intrathoracic pressure. During a forceful expiration, such as during a cough, intrathoracic pressure may briefly exceed atmospheric pressure.

Figure 9A:
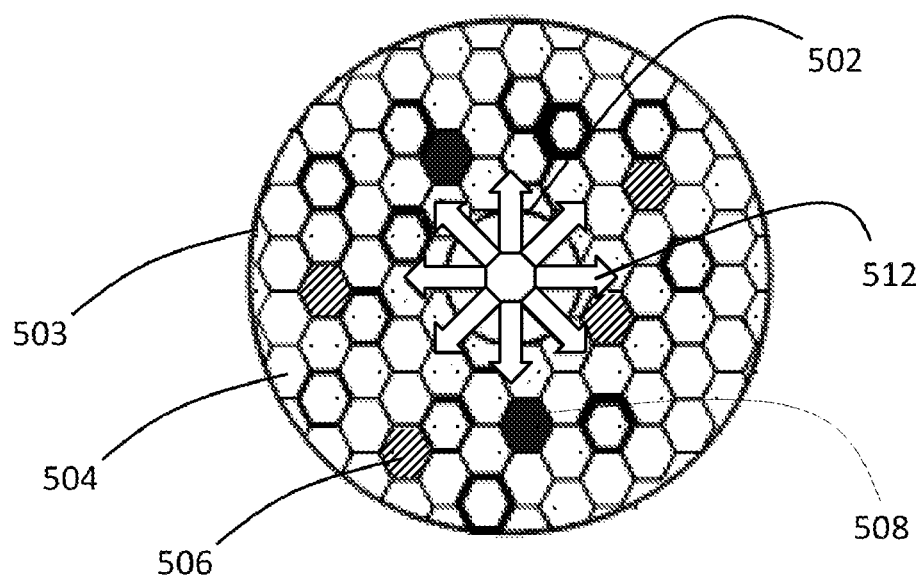
FIGS. 9A and 9B are schematic diagrams of an alveolar network in the lung parenchyma.
Figure 9B:
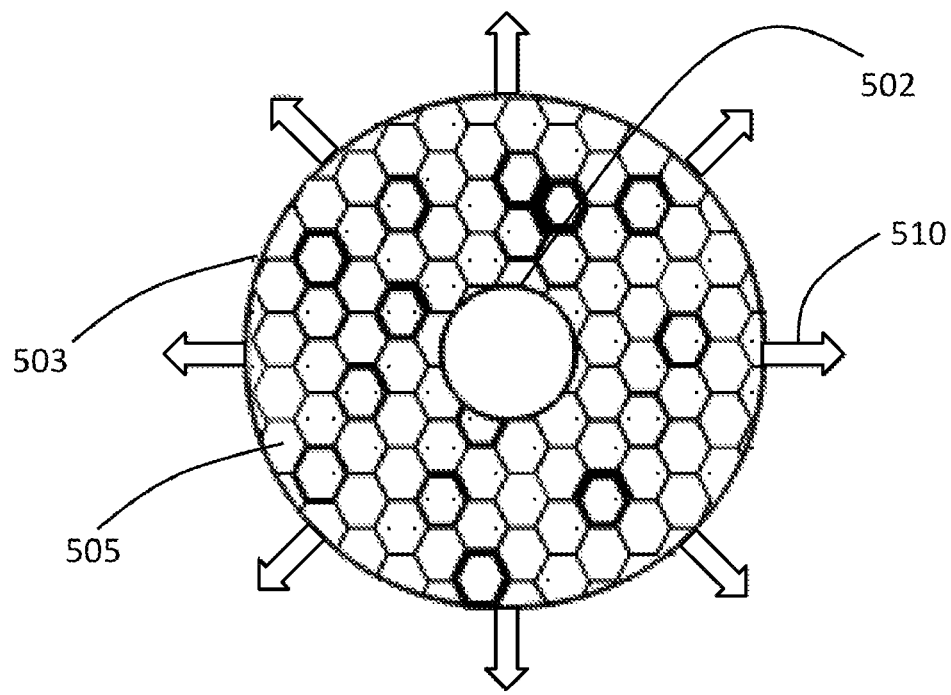

The "pull" effect of negative pressure on the alveoli during inspiration provides for an equal distribution of the expanding force across the entire population of alveoli. FIGS. 9A and 9B illustrate this effect, with a schematic of the alveolar network in the lung parenchyma.

In FIGS. 9A and 9B, the central circle 502 represents a bronchiole around an airway, the outer circle 503 represents the exterior surface of the lung, and each hexagon 504, 506 or 508 represents an alveolus. The degree of openness of each alveolus is indicated by its shading, such that white shading indicates an open alveolus 504, lined shading indicates a partially closed alveolus 506, and black shading indicates a fully closed alveolus 508. Further, the thickness of the lines surrounding each alveolus in FIGS. 9A and 9B indicate alveolar surface tension (i.e. distending pressure), such that thicker lines indicate higher surface tension and thinner lines indicate relatively lower surface tension. FIG. 9A illustrates that positive pressure directed into the airway exerts pushing forces (indicated by the arrows 512) that are unevenly transmitted to the alveoli, such that some alveoli 506 and 508 remain partially or fully closed. FIG. 9B illustrates that a negative pressure applied on the exterior surface of the lung exerts pulling forces (indicated by the arrows 510) that are evenly transmitted to the alveoli.

In other words, the central circle in each of FIGS. 9A and 9B represents the wall 502 of an airway (e.g., a bronchiole), the outer circle indicates the exterior surface of a lung 503, and each hexagon represents an alveolus, where each alveolus may be open (shown as white alveoli, e.g., alveoli 504, 505), partially closed (indicated by hash lines, e.g., alveolus 506), or fully closed (shown as black alveoli, e.g., alveolus 508). The alveoli are interconnected (not shown) from the lung surface 503 to the airway. In the intact organism, negative pressure is exerted on the surface of the lung 503 to pull the alveoli open (FIG. 9B). This pulling force, as indicated by block arrows (e.g., 510), is evenly transmitted throughout the lung parenchyma to the airway, resulting in a population of open alveoli (e.g., 505). In contrast, with conventional positive pressure ventilation, the airway is pressurized to forcibly fill the alveoli with air (FIG. 9A). Transmission of air pressure, as indicated by block arrows (e.g., 512), will follow the path of least resistance leading to overexpansion of compliant alveoli (e.g., 504), leaving less compliant alveoli partially unaerated (e.g., 506) or fully unaerated (e.g., 508).

In addition, movement of an alveolus stimulates surfactant production from Type II pneumocytes, which facilitates reduction in the surface tension inside the alveolus, facilitating its expansion during inspiration. Without surfactant, the surface tension in an alveolus is very high, resulting in a very high distending pressure, which hampers airflow.

Even after a forced expiration in vivo, considerable air remains in healthy lungs because the subatmospheric intrathoracic pressure keeps the alveoli slightly inflated. However, in patients with certain disorders, significant alveolar closure occurs at the end of expiration, which decreases lung compliance during the following inspiration. Opening closed alveoli requires a critical pressure to be achieved before the alveoli can expand. Such patients can benefit from the application of a positive end-expiratory pressure (PEEP) or CPAP which prevent alveolar closure during expiration.

A more extreme problem with alveolar closure occurs during lung transplantation. When the lungs are removed from the host body, exposure of the exterior of the lungs to atmospheric pressure can lead to widespread atelectasis.

However, when the lungs are ventilated according to an embodiment of the present disclosure, effective recruitment of lung parenchymal alveolar segments may be obtained, and over distension of recruited segments may be conveniently reduced or avoided. In particular, a desired pressure gradient in the lungs may be conveniently provided by adjusting the pressure outside the lungs (or pressure in the ventilation container) and the positive pressure in the airways of the lungs.

In an embodiment, a method of ventilating a lung may include applying a first pressure (P1) to an airway of the lung, and applying a second pressure (P2) to an exterior surface of the lung. The pressure differential, PD=P1−P2, is maintained positive and is varied to cause the lung to breathe. PD may be considered to be equivalent to TPG. The airway pressure P1 may be maintained higher than the atmospheric pressure, and the exterior pressure P2 may be varied between a higher level and a lower level to cause the lung to ventilate, where the lower level is below the atmospheric pressure. P1 may be maintained at a constant value, such as at a constant value from about 5 to about 10 cmH$_2$O. PD may be varied from about 7 to about 30 cmH$_2$O. For example, when P1 is constant at 5 cmH$_2$O, P2 may vary from −25 to −2 cmH$_2$O. When P1 is constant at 10 cmH$_2$O, P2 may vary from −20 to 3 cmH$_2$O. A regenerative vacuum pump, such as a regenerative turbine, may be used to apply and control both P1 and P2. P1 may be regulated using the exhaust pressure at the exhaust side of the pump, and P2 may be regulated using the vacuum pressure at the vacuum (intake) side of the pump. Conveniently, a single turbine may be sufficient to apply and control both P1 and P2.

In comparison, positive displacement pumps, such as roller pumps or peristaltic pumps, are not as convenient to use to control the airway and exterior pressures in some embodiments disclosed herein. One of the reasons is that, as will be understood by those skilled in the art, it is more difficult to precisely control the fluid pressures at the inlet (intake) and outlet (output) of a positive displacement pump by adjusting its pumping speed, as compared to a regenerative pump. For example, with a positive displacement pump, the inlet pressure (or the pressure differential across the inlet and the outlet of the pump) can vary at the same given pumping speed, so that changing the pumping speed may not provide a predictable pressure change. With a regenerative pump, the pumping speed is more predictably related to the pressure differential across the inlet (intake) and the outlet (output).

Normal physiology also informs the magnitude of the pressures that may provide for effective ventilation of lungs ex vivo. Normal physiology dictates $P_{AW}$ and the pressure inside alveoli is 0 cmH$_2$O (i.e., at atmospheric pressure) at rest, with an intrathoracic EEP around −7 cmH$_2$O being resisted by an elastic recoil of the lungs of approximately the same magnitude. Deep inspiration can invoke an intrathoracic EIP of −30 cmH$_2$O, whereas a cough or valsalva maneuver can induce an intrathoracic pressure of 100 to 200 cmH$_2$O. Because of the alveolar network that applies traction from the surface of the lungs to the central airway (as illustrated in FIGS. 9A and 9B), application of a negative pressure to the outside of the lungs is expected to be a physiological method for causing air movement into the lung. However to reduce the amount of vacuum applied to lungs being ventilated ex vivo, a small positive air pressure can be applied to the airway to yield a TPG that is maintained within the physiologic range. For example, application of a positive pressure into the airway of between 5 to 10 cmH$_2$O can reduce the required vacuum applied to the exterior surface of the lungs by an equivalent amount. An airway pressure above this amount is considered less physiologic and may be undesirable.

In another embodiment, a method of ventilating a lung includes varying an exterior pressure around a lung to ventilate the lung. The exterior pressure is applied by a gas in fluid communication with a gas pump for varying the exterior pressure. The gas pump may be a regenerative pump, such as a turbine pump. The gas around the lung may be confined within a constant volume (e.g. between fixed walls) but the amount of gas (e.g., moles of the gas) in the constant volume is varied using the pump to change the exterior pressure applied to the lung.

It has been recognized that when a varying pressure is applied to the exterior surface of the lungs using a fixed amount of gas confined around the lungs by compressing or decompressing the fixed amount of gas, such as by varying the volume that the gas occupies, a problem with pressure control could arise. For example, due to air leakage through the lungs, the amount of gas confined around the lungs may increase over time. As a result, to achieve the same pressure the gas volume control has to be re-calibrated, or the gas amount has to be re-adjusted, which can interrupt the normal ventilation cycles, or require manual re-adjustment of the device or the control settings.

In comparison, when the exterior pressure around the lungs is varied by applying a gas pressure using a gas in fluid communication with a gas pump for varying the exterior pressure, the exterior pressure can be conveniently controlled continuously without interruption over a long period of time, by automatically adjusting the pump speed, optionally aided with one or more proportioning valves that are configured to provide more flexibility in the control of pressures and fluid flow as illustrated herein. Air leakage through the lungs will not affect the pressure control settings and thus will not cause interruption of the ventilation process or require re-setting of the control parameters.

The analysis of lung physiology in vivo indicates that during ex vivo NPV, effective recruitment of lung parenchymal alveolar segments requires that the TPG always be above zero, including above around 7 cmH$_2$O. This latter value is analogous to the difference, at the end of expiration in vivo, between the airway pressure inside the lungs (atmospheric) and the intrathoracic pressure (around −7 cmH$_2$O); this TPG resists the elastic recoil of the alveoli and prevents alveolar collapse. In general, herein, TPG during ex vivo NPV is the difference between the pressure inside the airways of the lung and the pressure inside the container housing the lung; it will be a positive value when the airway pressure is higher than the container pressure. A consequence of the TPG always being greater than zero during ex vivo NPV may be a continuous leakage of air into the container holding the lung, if, for instance, the seal between the container and lid is not perfect, the seal between the endotracheal tube and an airway of the lung (e.g., the trachea) is not perfect or if, for instance, the lungs have microscope ruptures, such as bronchopleural fistulae.

EXAMPLES

Example I

The example apparatus and methods described in this disclosure (for example, as shown in FIGS. 3-8) were used for EVLP and combined negative and positive pressure ventilation (NPV/PPV) in a series of experiments on porcine lungs. For each experiment, a pair of lungs was rapidly excised from a 40-50 kg pig following appropriate euthanasia and exsanguination. The lungs were mounted in the sealable container in the apparatus. An endotracheal tube was connected to the trachea of the lungs. The vasculature of the lungs was connected to a perfusion system, and perfusion was initiated. The perfusate comprised either an acellular albumin solution, a mixture of whole blood and albumin solution, or a mixture of concentrated red blood cells (pRBCs) and albumin solution. The composition of the albumin solution is presented in Table 1.

TABLE 1

Composition of albumin solution for lung perfusion

| Component | mmol/L | g/4 L |
|---|---|---|
| Glucose | 10 | 7.20 |
| NaCl | 117 | 27.35 |
| KCl | 5.9 | 1.76 |
| NaHCO$_3$ | 25 | 8.40 |
| NaH$_2$PO$_4$ | 1.2 | 0.66 |
| CaCl$_2$ | 1.12 | 0.66 |
| MgCl$_2$ | 0.512 | 0.42 |
| sodium pyruvate | 1 | 0.44 |
| bovine serum albumin | | 160 |
| | | Adjust pH to 7.4 |

A computer controlled the proportioning valves and turbine in the apparatus using input from pressure sensors for $P_{IT}$ and $P_{AW}$, as described for FIGS. 3-6. The computer recorded data from the airway flow sensor, as located in FIGS. 3-5, but did not use this information to control the apparatus. The computer was instructed to cause cycles of inspiration and expiration by entering into the computer desired set-points for: inspiratory time ($t_i$), expiratory time ($t_e$), end-inspiratory pressure (EIP) inside the sealed container, end-expiratory pressure (EEP) inside the sealed container, and a constant positive airway pressure.

The lungs were perfused and ventilated for 12 hours. Data on lung mechanics as well as vascular function were collected continuously over the 12 hour period. Perfusate samples were collected at regular intervals to measure dissolved gas content and inflammatory marker levels.

FIGS. 10 to 17 present data derived from experiments on porcine lungs using this NPV/PPV apparatus and method. In all of these figures, the pressures are all relative to atmospheric pressure (i.e., atmospheric pressure was 0 cmH$_2$O).

Figure 17:
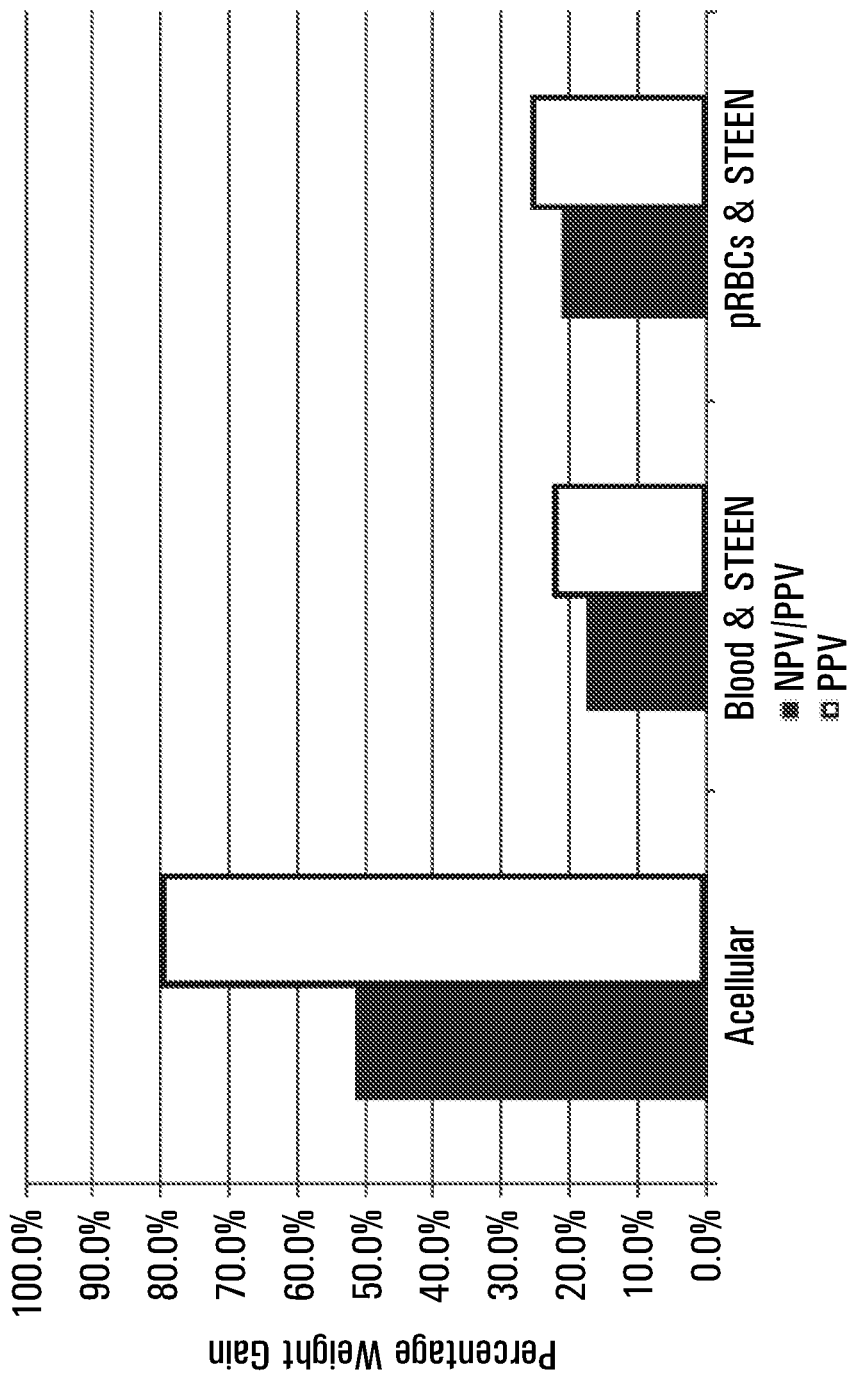
FIG. 17 is a bar graph illustrating edema formation during ex vivo lung perfusion (EVLP) of sample porcine lungs, comparing a combined negative and positive pressure ventilation strategy (NPV/PPV, using example ventilation apparatus and methods as disclosed herein) and a typical positive pressure ventilation strategy (PPV) with respect to three different perfusates: an acellular mixture, a mixture of whole blood and solution, and a mixture of red blood cell concentrate (pRBC) and solution.

In addition, as a comparator, porcine lungs were subjected to the same experimental protocol mutatis mutandis with no NPV and with PPV provided by a standard ICU ventilator. FIG. 17 compares data obtained from the NPV/PPV protocol and this comparator.

The TPG could be accurately varied over time in response to user-inputted set-points to drive breathing ex vivo.

Figure 10:
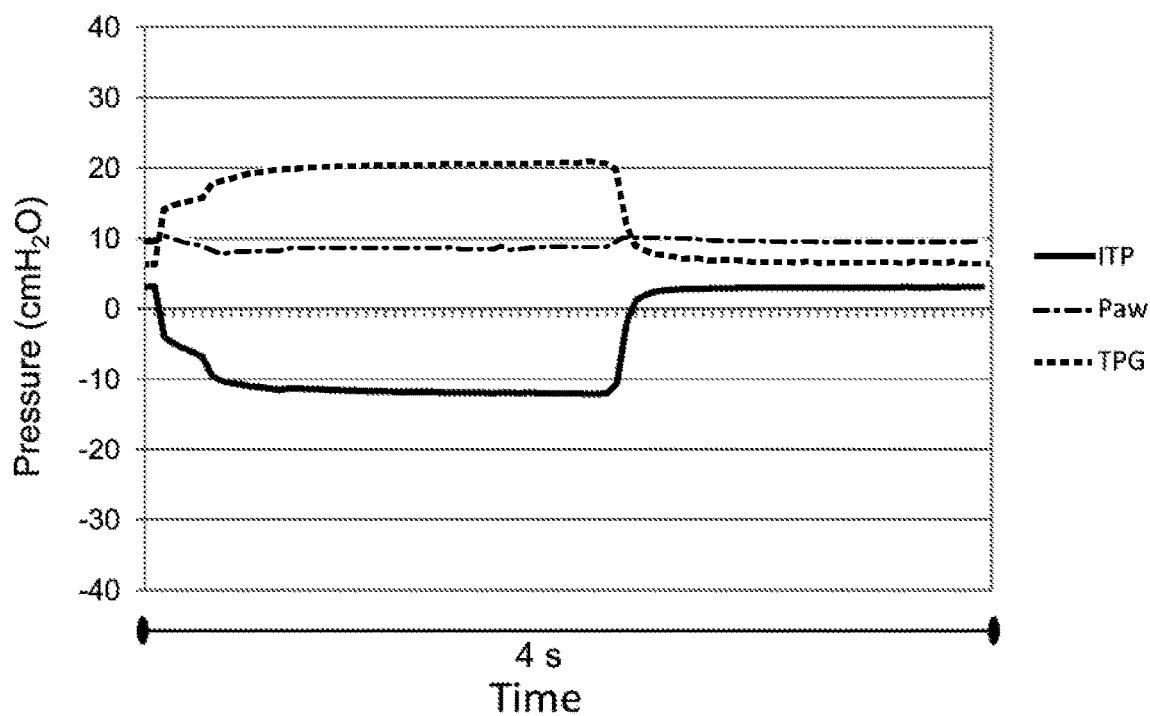
FIG. 10 is a line graph illustrating representative intrathoracic pressure (ITP), airway pressure ($P_{aw}$), and transpulmonary gradient (TPG) profiles over a time period of 4 seconds obtained from sample porcine lungs ventilated according to an embodiment of the present disclosure.

In FIG. 10, the set-point for constant airway positive pressure was 10 cmH$_2$O, the set-point for EIP was −10 cmH$_2$O, and the set-point for EEP was 4 cmH$_2$O. FIG. 10 presents data for the measured container pressure (ITP), airway pressure (P$_{aw}$), and TPG during one inspiration and expiration at these settings. At each time point, the TPG was calculated as (P$_{aw}$-ITP). The TPG minimum was around 6 cmH$_2$O; the TPG maximum was around 20 cmH$_2$O.

Figure 11:
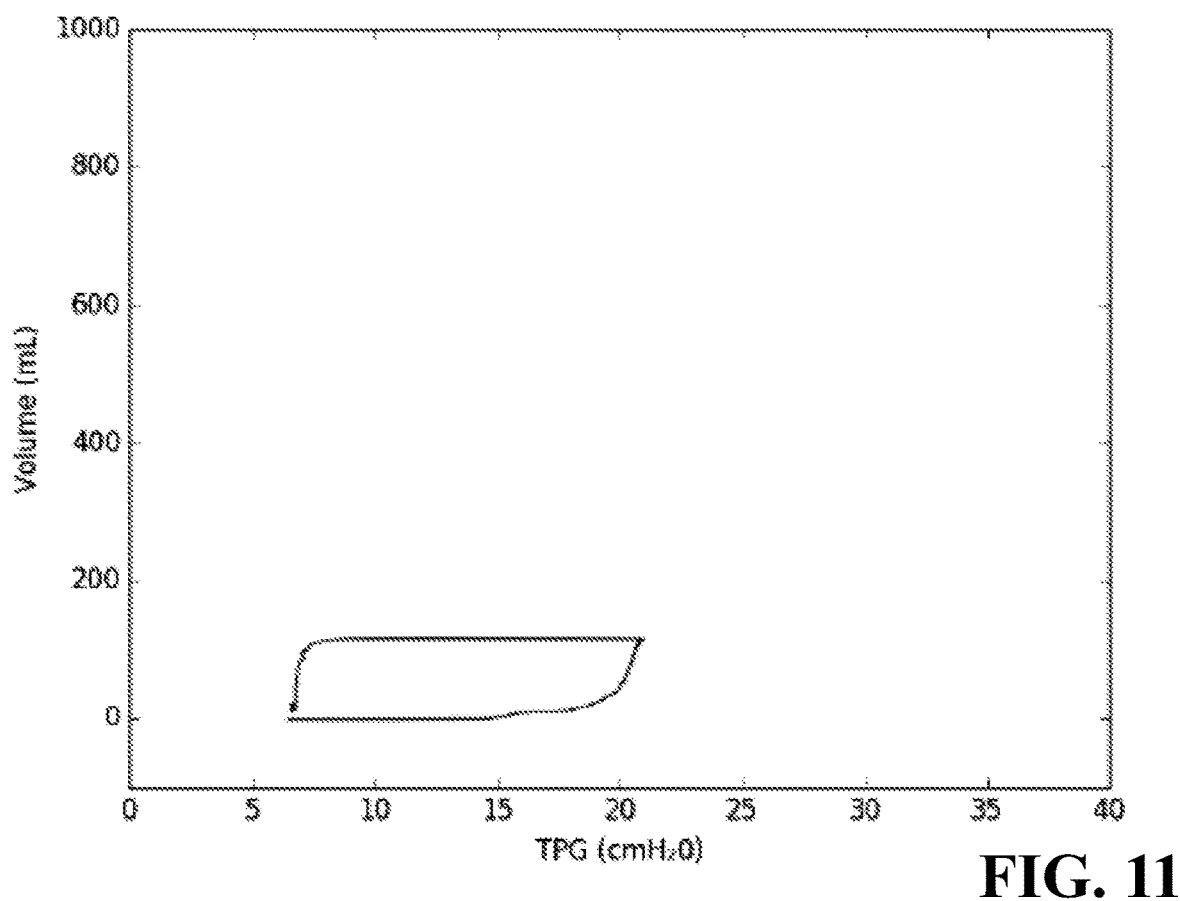
FIG. 11 is a line graph illustrating a pressure-volume profile from the same experiment as FIG. 10.

FIG. 11 presents a pressure-volume loop from the same experiment as FIG. 10.

Figure 12:
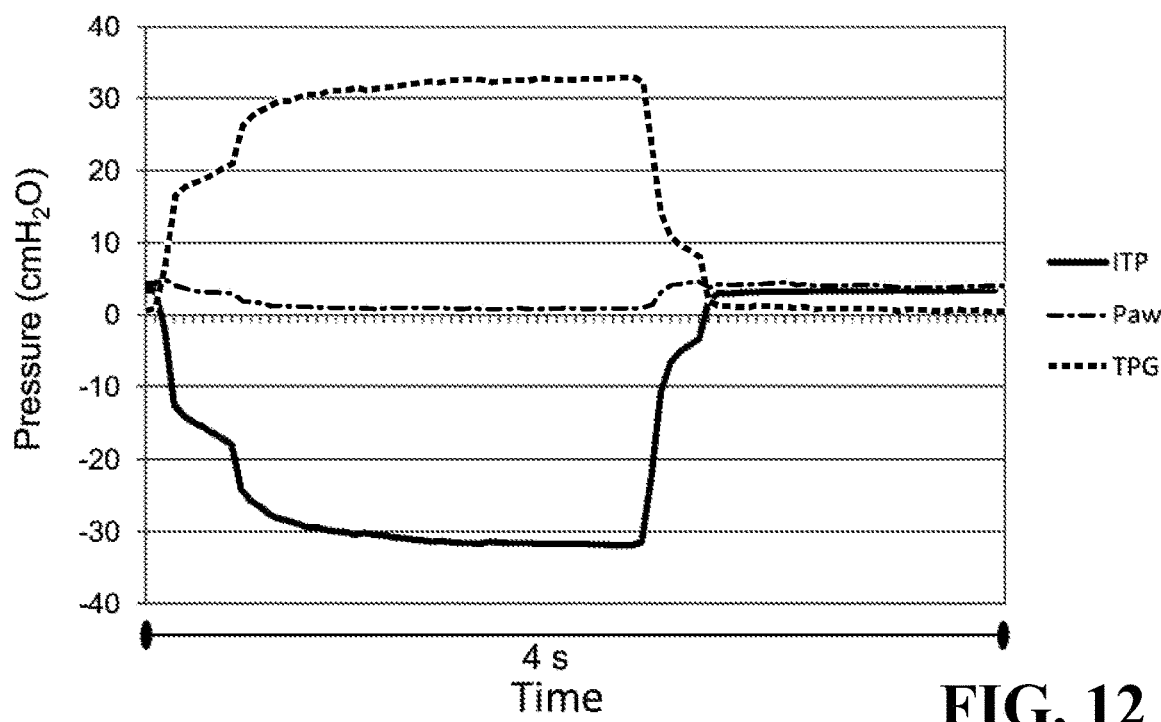
FIG. 12 is a line graph illustrating representative intrathoracic pressure (ITP), airway pressure ($P_{aw}$), and TPG profiles over a time period of 4 seconds obtained from sample porcine lungs ventilated according to an embodiment of the present disclosure.

FIG. 12 provides the same type of data as FIG. 10, but in this experiment the set-point for constant airway positive pressure was 4 cmH$_2$O, the set-point for EIP was −30 cmH$_2$O, and the set-point for EEP was 4 cmH$_2$O. The TPG minimum was around 0 cmH$_2$O; the TPG maximum was around 32 cmH$_2$O.

Figure 13:
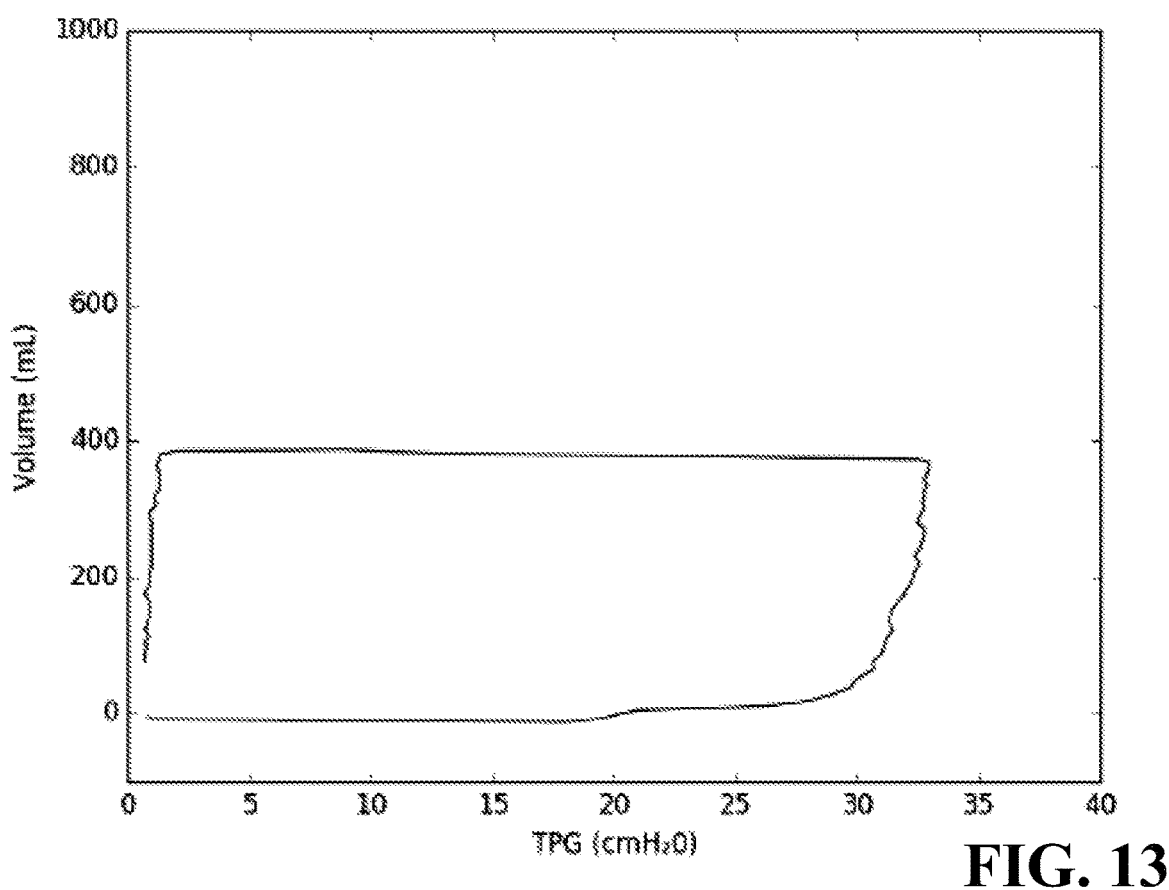
FIG. 13 is a line graph illustrating a pressure-volume profile from the same experiment as FIG. 12.

FIG. 13 presents a pressure-volume loop from the same experiment as FIG. 12.

Figure 14A:
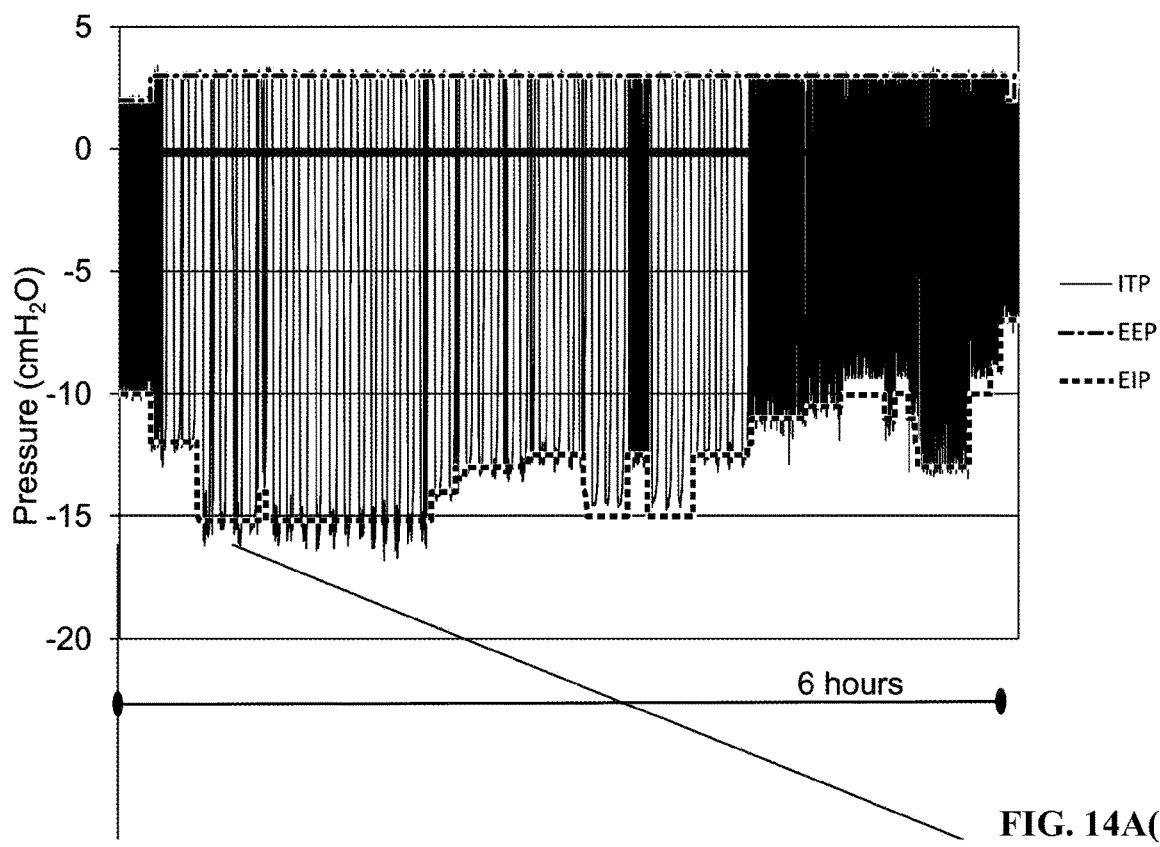
FIG. 14A shows a line graph (top) in FIG. 14A(a) illustrating a representative intrathoracic pressure (ITP) profile over time, with a section of which shown in expanded time scale at the bottom in FIG. 14A(b)
Figure 14A:
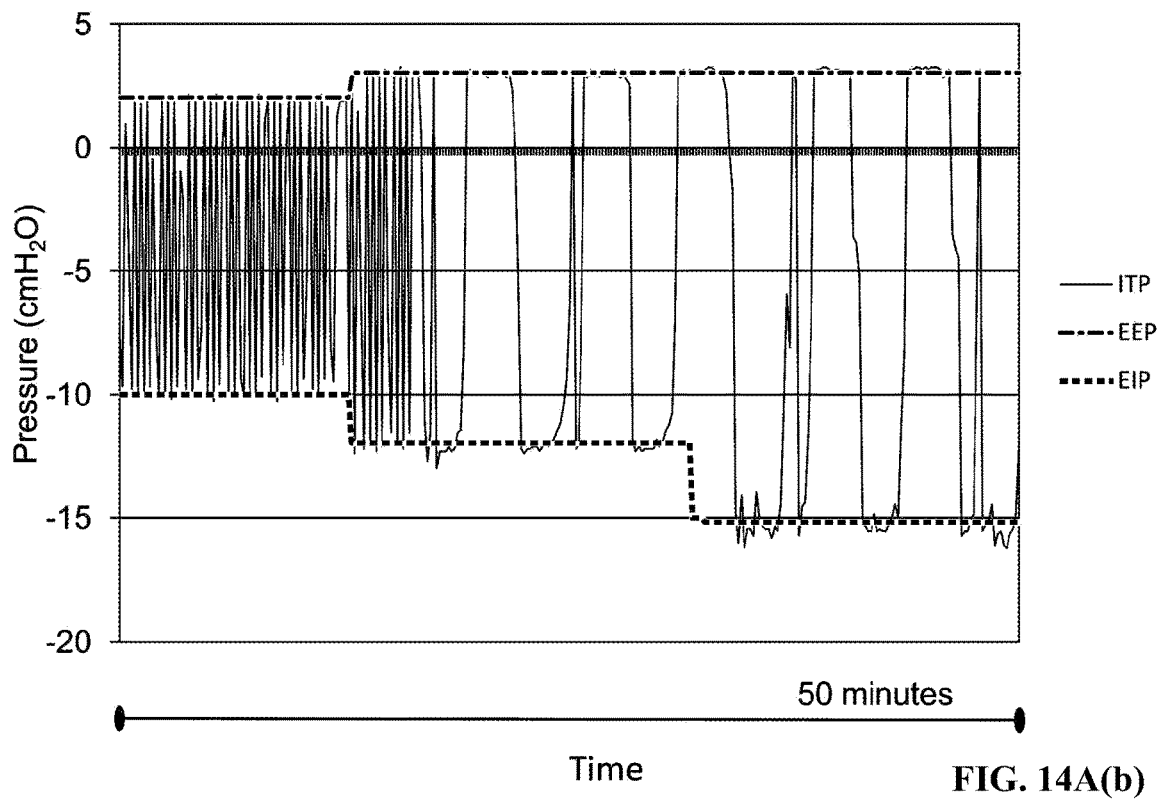
Figure 14B:
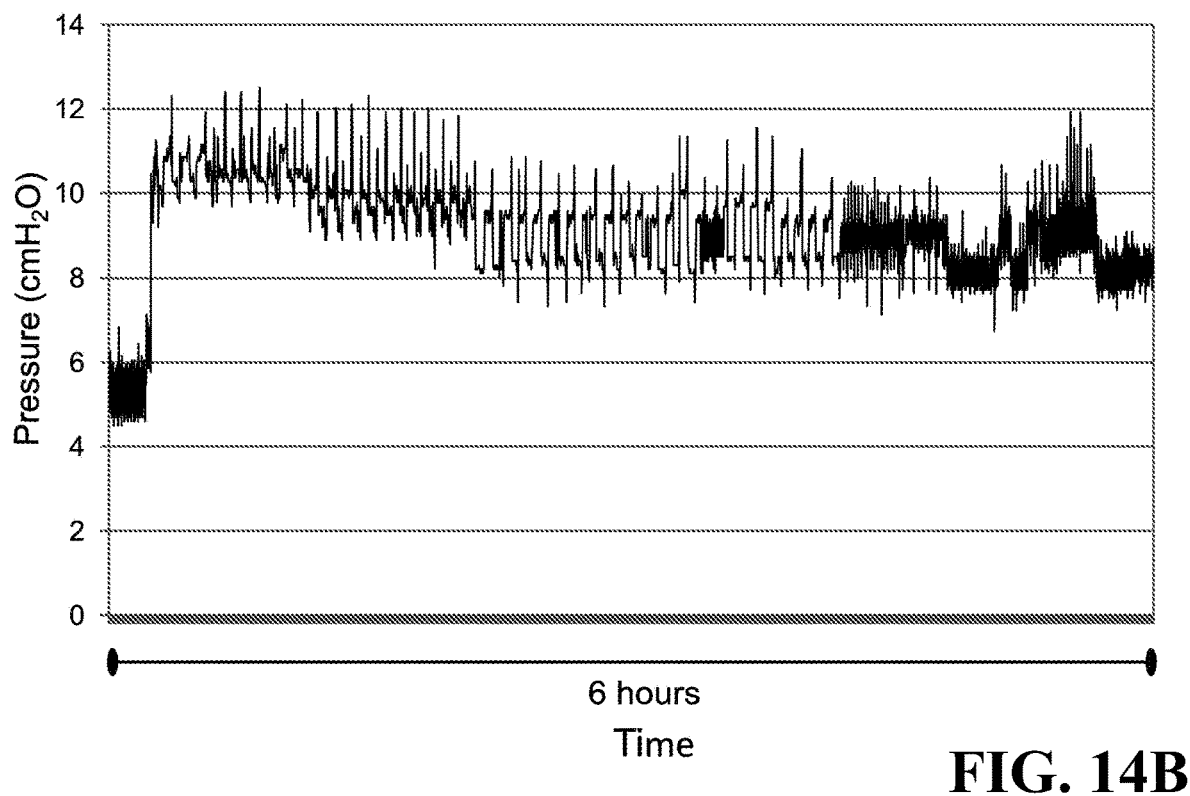
FIG. 14B is a line graph of the measured airway pressure over time during the same experiment as in FIG. 14A.
Figure 14C:
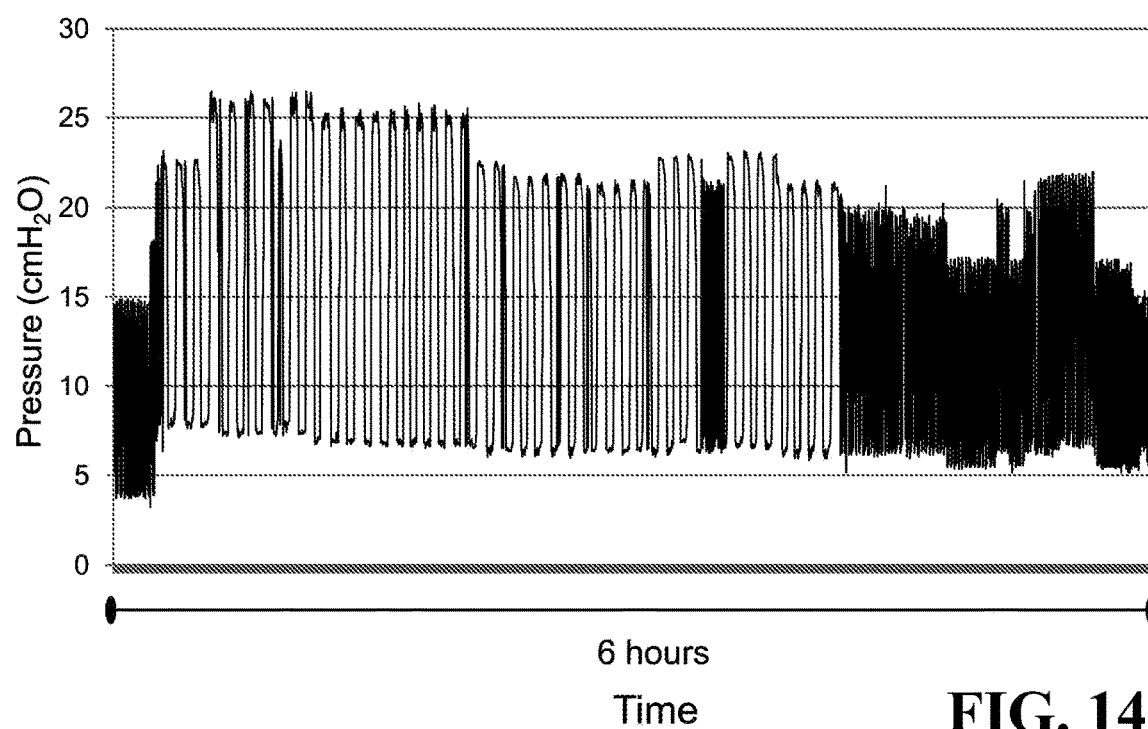
FIG. 14C is a line graph of the transpulmonary gradient over time during the same experiment as in FIG. 14A.

FIGS. 14A to 14C show representative pressure profiles obtained in an experiment, where sample porcine lungs were ventilated according to an embodiment of the present disclosure, in which a constant positive airway pressure was directed into the airway of the lungs and the gas pressure (ITP) in a container surrounding the lungs was oscillated between a higher pressure (slightly positive) and a lower pressure (negative). The set-points for the end expiratory pressure (EEP) and end inspiratory pressure (EIP) are indicated by different lines in FIG. 14A. FIG. 14A(b) is a magnified view of an initial time period in FIG. 14A(a). The time period for FIG. 14A(a) was about 6 hours, and the time period for FIG. 14A(b) was about 50 min. In both FIGS. 14A(a) and 14A(b), the ITP was sampled every 10 seconds, such that although the ITP was oscillating throughout the experiment to cause the lungs to breath, the apparent oscillations of ITP seen in FIG. 14A are not the actual oscillations of ITP. However, oscillation frequency shown in FIG. 14A was inversely correlated with the actual times of expiration and inspiration.

For the experiment from which data is shown in FIGS. 14A to 14C, the EEP and EIP were set by a user at the various points in time, as indicated in FIG. 14A. FIG. 14A shows that the observed pressure inside the sealed container (ITP) changed over time in response to user-defined set-points for EIP, EEP, t$_i$, t$_e$, and constant positive airway pressure. Set-points for EIP, EEP, t$_i$, and t$_e$ were serially altered during the experiment to challenge the apparatus. The CPAP set-point was only changed once: when around 15-20 min after the zero time point, the CPAP set-point was increased by the user to around 9 cmH$_2$O. In both FIGS. 14A(a) and 14A(b), the ITP was sampled every 10 seconds, such that although the actual ITP was oscillating throughout the experiment to cause the lungs to breath, the "observed ITP oscillations" seen in FIG. 14A were not the actual oscillations of ITP. The frequency of the "observed ITP oscillations" shown in FIG. 14A was inversely correlated with the frequency of expiration and inspiration. FIG. 14A(b) is an expanded view of an initial period of time, lasting around 50 min, from FIG. 14A(a). The expanded view in FIG. 14A(b) shows the more tightly-spaced "observed ITP oscillations", which were reflective of the shorter periods of the actual ITP oscillations due to lower t$_i$ and t$_e$ set-points in the initial portion of the profile. In addition, FIGS. 14A(a) and 14(b) show that when the user changed set-points, the system adjusted rapidly. FIG. 14B shows that throughout this experiment the measured airway pressure (P$_{AW}$) remained fairly constant, perhaps showing a gradual decrease over time, save for the initial portion of the profile where airway pressure rapidly increased in response to the aforementioned increase in the CPAP set-point. FIG. 14C shows the measured TPG throughout the experiment, calculated as P$_{AW}$-ITP, which was kept between around 5 cmH$_2$O to around 26 cmH$_2$O for most of the experiment.

Figure 15:
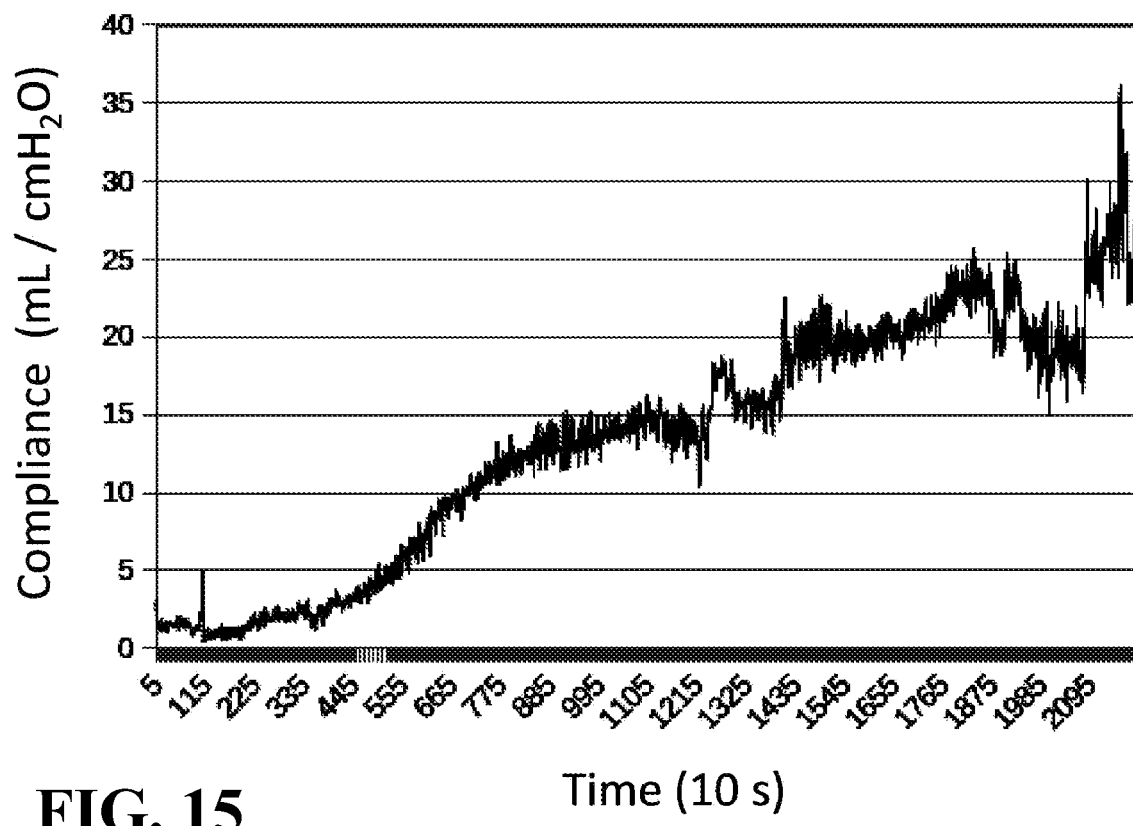
FIG. 15 is a line graph illustrating a representative lung compliance profile over time obtained from sample porcine lungs ventilated according to an embodiment of the present disclosure.

FIG. 15 shows that the compliance (in mL/cmH$_2$O) of a porcine lung increased over time (in 10 s) during perfusion and ventilation. Compliance was calculated as the volume of inspired air divided by the difference between the TPG at the beginning and at the end of the inspiration.

Figure 16:
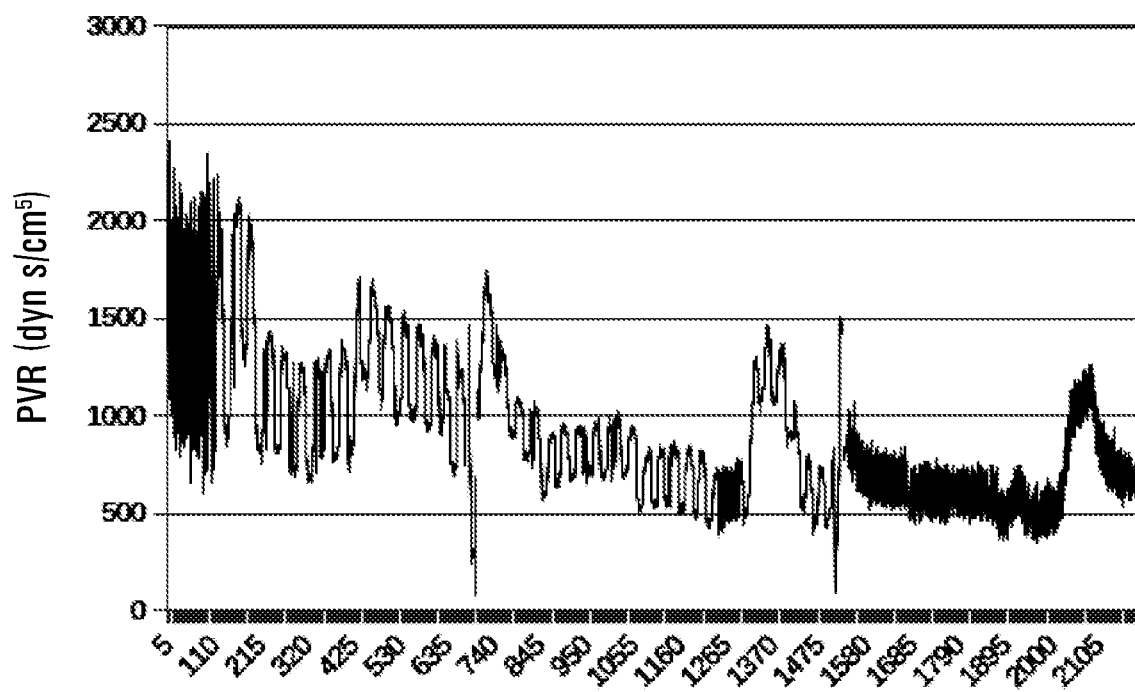
FIG. 16 is a line graph illustrating a representative pulmonary vascular resistance (PVR) profile over time obtained from sample porcine lungs ventilated with example ventilation apparatus and methods as disclosed herein.

FIG. 16 shows that the pulmonary vascular resistance (PVR, in dyn s/cm$^5$) of a porcine lung decreased over time (in 10 s) during perfusion and ventilation. As is known to one skilled in the art, when the concentration of oxygen in the air of the alveoli decreases below normal, the adjacent blood vessels constrict, thereby increasing vascular resistance. Therefore, the PVR can provide an indirect measure of alveolar recruitment and, more generally, provides a measure of the health of an ex vivo lung.

FIG. 17 shows that for the three different perfusates, edema formation during EVLP of porcine lungs was less during ventilation in an NPV/PPV apparatus of the disclosure as compared to a standard PPV apparatus. As is known to one skilled in the art, in normal human lungs in vivo, there is a mean filtration pressure at the pulmonary capillary membrane which causes a continual flow of fluid from the pulmonary capillaries into the interstitial spaces. This fluid is pumped back to the circulation through the pulmonary lymphatic system. The slight negative fluid pressure in the interstitial spaces keeps fluid from leaking into the alveoli. Any factor that causes this interstitial fluid pressure to rise into the positive range can cause filling of the alveoli with free fluid. Therefore, reducing lung edema during ex vivo maintenance of lungs may be helpful.

Example II

Six human donor lungs were obtained by appropriate methods and mounted in the example apparatus shown in FIG. 3 and subjected to EVLP with NPV/PPV (N=6).

Figure 18:
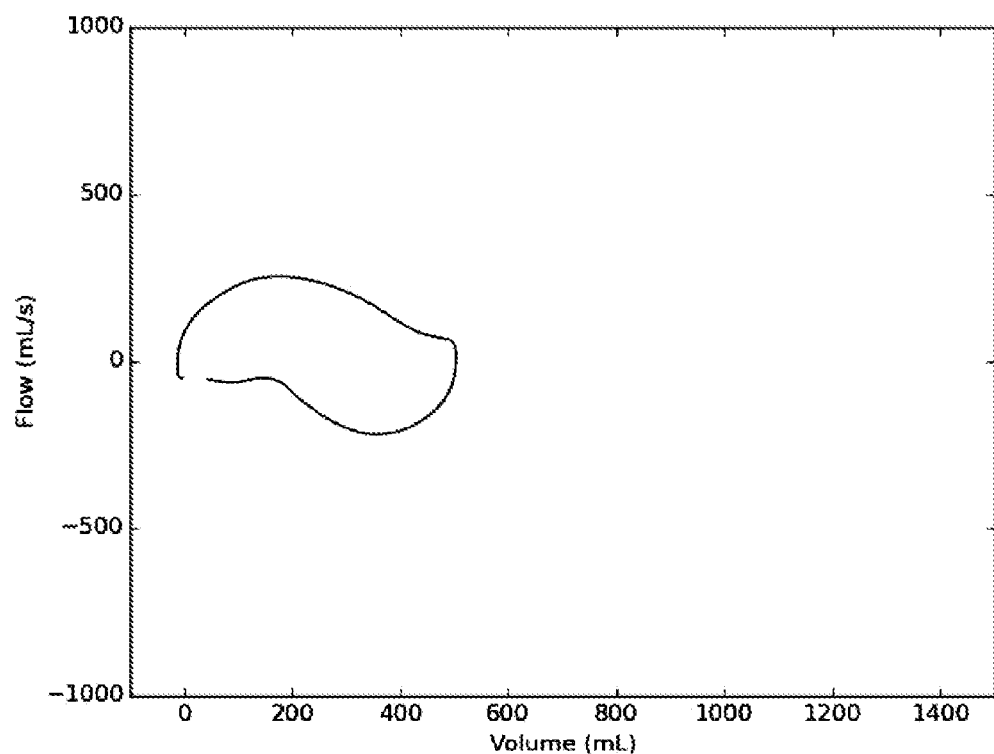
FIGS. 18 and 19 are line graphs illustrating representative flow-volume profiles obtained from sample human lungs ventilated with example ventilation apparatus and methods as disclosed herein.
Figure 19:
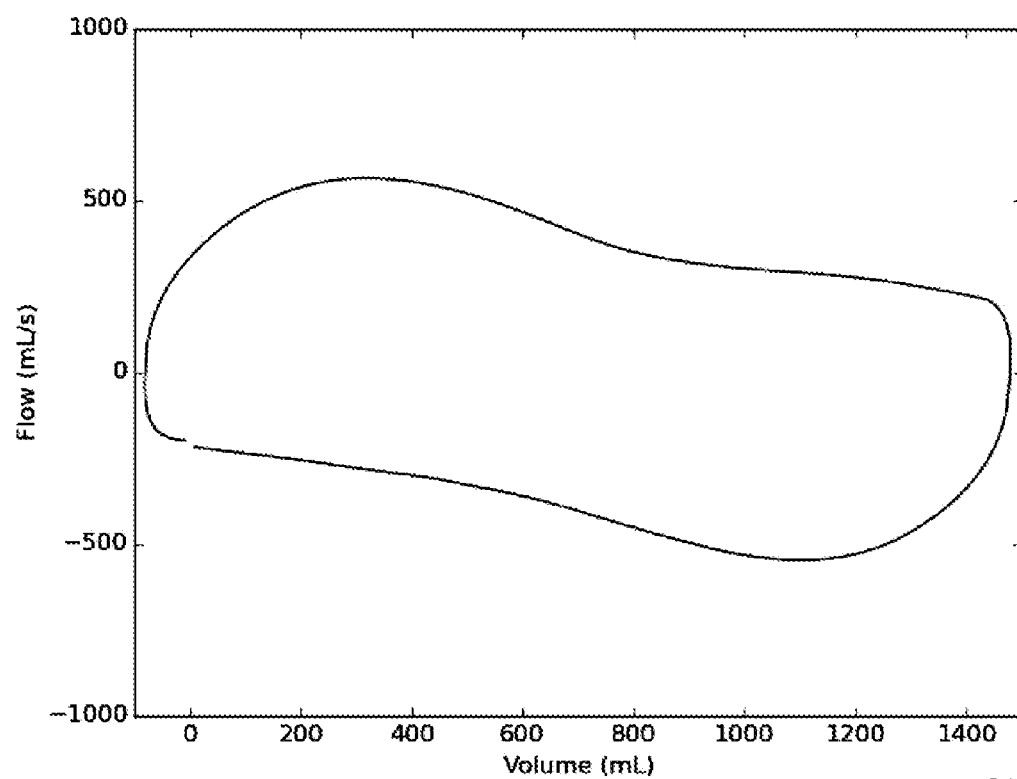

FIGS. 18 and 19 show representative flow-volume profiles for sample human lungs. Flow is presented in mL/s and volume is presented in mL. FIG. 18 shows a profile obtained during an initial ventilation period with an EIP set-point of −15 cmH$_2$O for preservation of the lungs. Ventilation was continued to allow recruitment of atelectatic alveoli. After the recruitment was completed, the lungs were ventilated at an EIP set-point of −18 cmH$_2$O for evaluation, and FIG. 19 shows a profile obtained during this evaluation period.

A flow-volume profile shows the relationship between inspiratory and expiratory flow against the lung volume during maximal forced inspiration and expiration. During expiration, flow was positive. During inspiration, flow was negative. The data points move clockwise with time in the profile.

FIGS. 18 and 19 demonstrate that the recruitment of alveoli during ventilation ex vivo in the NPV/PPV apparatus of the disclosure resulted in increased flow and vital capacity (i.e., the maximum volume expired after a maximum inspiration).

Example III

Figure 20:
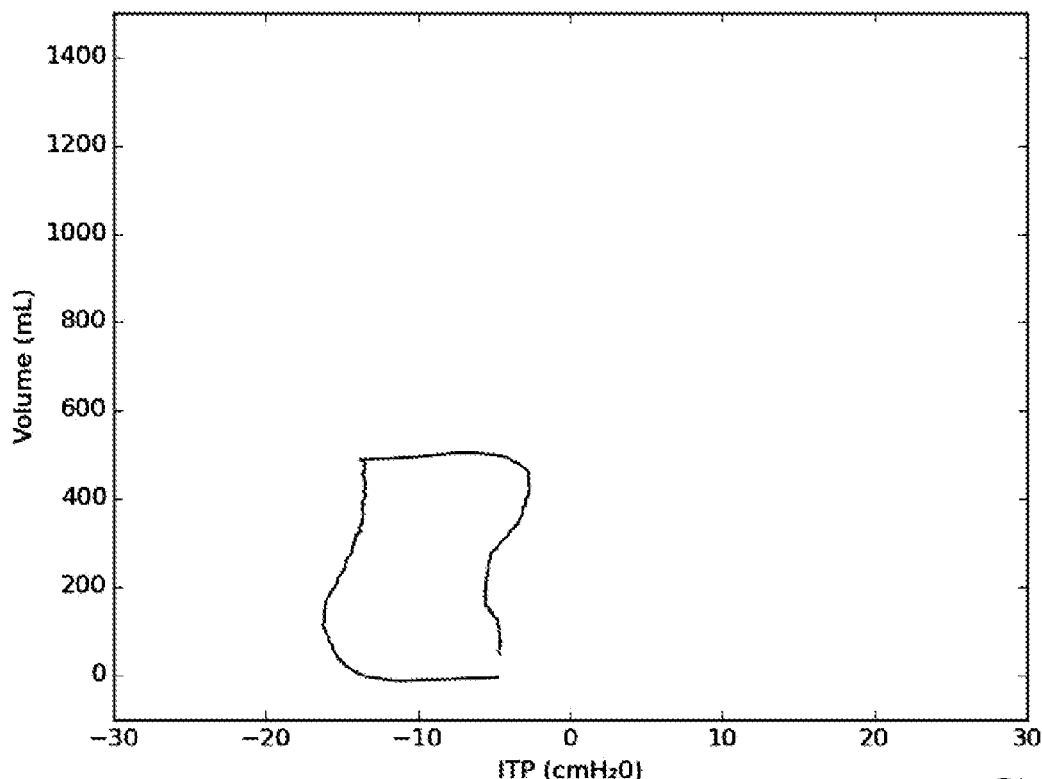
FIGS. 20 and 21 are line graphs illustrating representative pressure-volume profiles obtained from sample human lungs ventilated with example ventilation apparatus and methods as disclosed herein.
Figure 21:
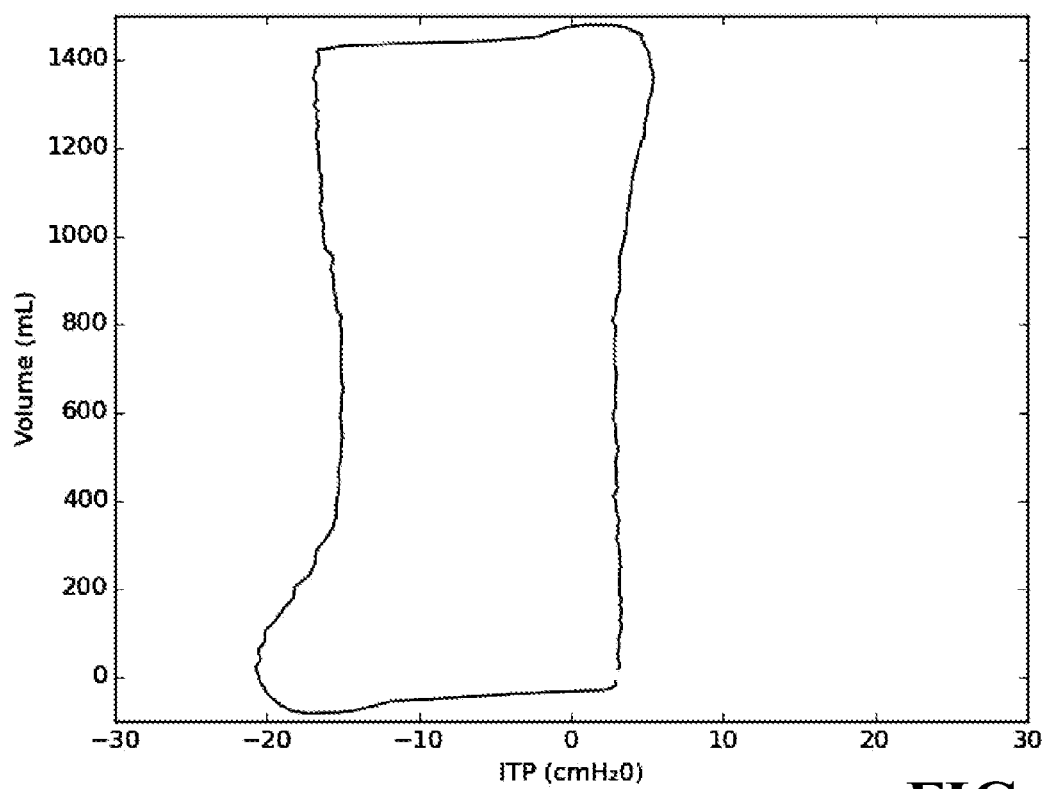

FIGS. 20 and 21 show representative pressure-volume profiles for sample human lungs ventilated ex vivo as in Example II. FIG. 20 shows a profile obtained in the initial ventilation during preservation, and FIG. 21 shows a profile obtained during the later evaluation period.

FIGS. 20 and 21 also demonstrate the recruitment of alveoli during ventilation ex vivo in the NPV/PPV apparatus of the disclosure.

It was observed during experimentation, including that described in Examples I, II, and III, that the NPV/PPV apparatus and methods of the disclosure had advantages relative to standard PPV apparatuses and methods. The NPV/PPV apparatus and methods resulted in faster recruitment of the lung parenchyma (i.e., resolution of atelectasis), with a lower or equivalent TPG. There was less formation of bullae in the donor lungs, with less broncho-pleural fistula formation and consequently less air leak from the lungs. Broncho-pleural fistulae were observed as localized bubbling on the exterior surface of the lungs. Lower inflammatory marker expression in the perfusate was observed as well. Lung edema occurred to a lesser degree.

It was also observed during experimentation that the NPV/PPV apparatus and methods of the disclosure, relative to a comparable NPV apparatus and method, resulted in lungs with superior physiological properties during EVLP and ventilation ex vivo.

Example IV (Comparison)

Figure 22:
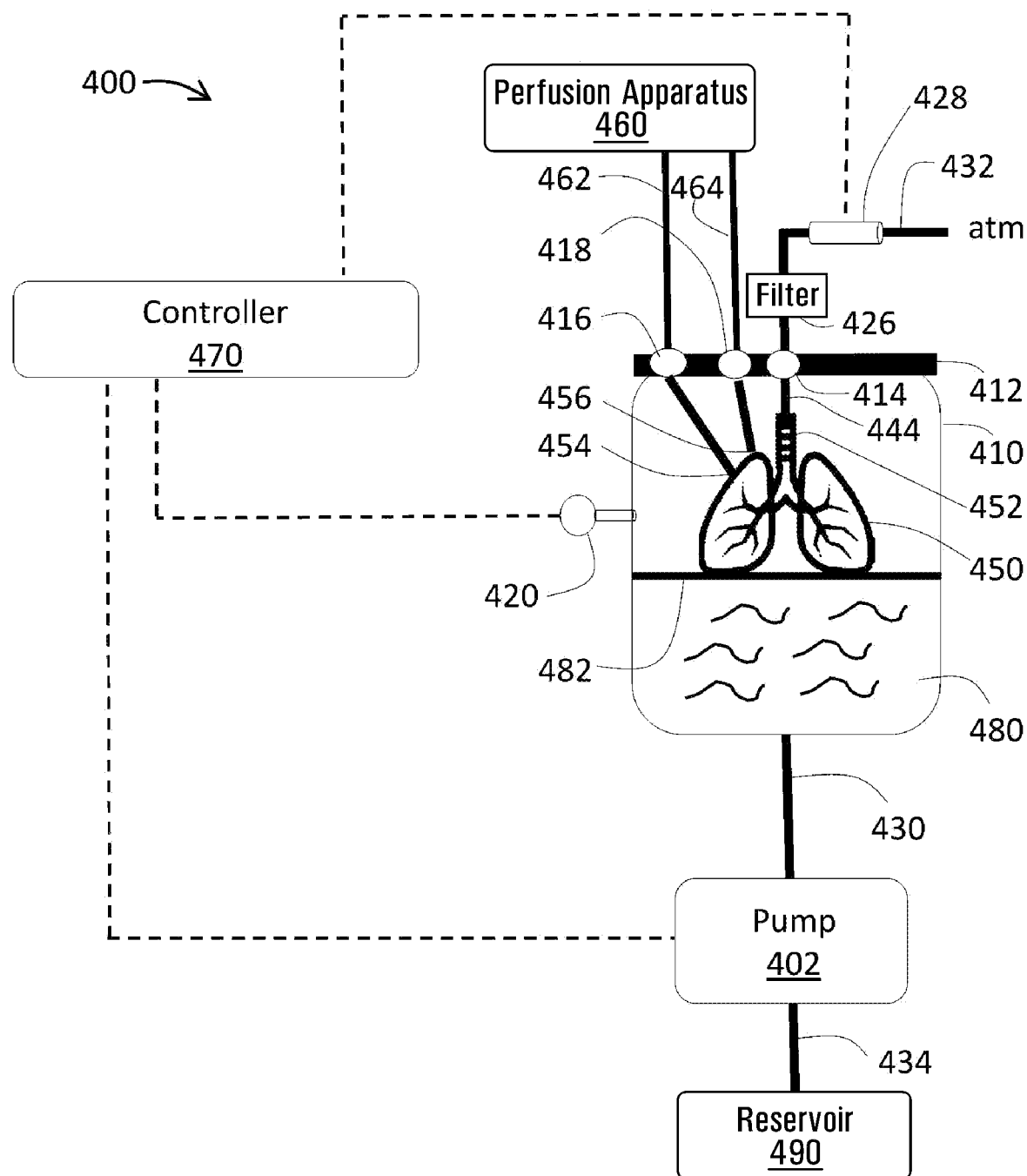
FIG. 22 is a schematic diagram of a comparison apparatus for negative pressure ventilation of lungs ex vivo.

FIG. 22 illustrates an example comparison apparatus 400 for negative pressure ventilation, which was tested with three porcine lungs (N=3). Apparatus 400 was used to apply a negative pressure within organ chamber 410. In this example, apparatus 400 was not used to deliver positive airway pressure in the airway of the lung.

In the tests, donor lungs 450 were placed inside a hard-shell sealed container 410 in apparatus 400. The container 410 was partially filled with a saline liquid 480. The lungs 450 floated on top of a flexible plastic membrane 482, buoyed up by the liquid 480.

The tracheobronchial tree 452 of the lungs 450 was connected to a conduit 432 by an endotracheal tube 444. A conduit 462 connected the perfusion apparatus 460 to a pulmonary artery 454 of the lungs 450. A conduit 464 connected the perfusion apparatus 460 to a pulmonary vein 456 of the lungs 450.

The container 410 was sealed to the atmosphere by a lid 412. The conduit 432 extended through the lid 412 via a port 414. The conduit 462 extended through the lid 412 via a port 416. The conduit 464 extended through the lid 412 via a port 418.

A conduit 430 connected the container 410 at an opening below the fluid level to an occlusive roller pump 402 (a COBE™ perfusion pump). The inner space in container 410 was in fluid communication with conduit 430. A conduit 434 connected the roller pump 402 to a fluid reservoir 490.

Gas pressure inside the container 410 was lowered by pumping the liquid 480 out of the container 410, into the conduit 430, through the roller pump 402, into the conduit 434, and from thence into the reservoir 490. Gas pressure inside the container 410 was raised by pumping fluid in the opposite direction. By actuating the liquid 480 to and fro, the lungs 450 were caused to breathe through the endotracheal tube 444 and the conduit 432, which was open to the atmosphere.

An HME filter 426 was coupled to the conduit 432 to avoid desiccation of the airways of the lungs 450.

A controller 470, which was a computer, controlled the speed and direction of pumping by the roller pump 402. The control was implemented by optionally specifying a volume (e.g., tidal volume) to be removed from the container 410 or a target pressure (i.e., vacuum pressure) in the container 410.

In the latter option, the pressure in the container 410 (the "intrathoracic" pressure or $P_{IT}$) was measured by a pressure sensor 420. The pressure sensor 420 was an input into the controller 470. Unlike in Examples I-III and the apparatuses of FIGS. 2-6, airway pressure ($P_{AW}$) was not measured and was not a control input. The user specified set-points for EIP, EEP, $t_i$, and $t_e$ instructed the controller 470 as to the desired ventilation cycles. The controller 470 compared the pressure sensor 420 input to the user-defined set-points at each given time to control the roller pump 402.

Endotracheal tube airflow (V) was measured by a flow sensor 428. This data was recorded by the controller 470, but was not used to control the apparatus.

It was generally observed that the NPV apparatus 400 in comparative Example IV was cumbersome. The NPV apparatus 400 did not allow for precise and effective control of the TPG, as compared to the apparatuses of the disclosure tested in Examples I-III. In particular, higher negative pressures were required to cause effective inspiration, relative to the apparatuses in Examples I-III that combined NPV with PPV. In addition, altering the negative pressure by adjusting proportioning valves in the apparatuses of the disclosure was more precise and rapid than altering the negative pressure by adjusting the speed and direction of the roller pump 402 in the apparatus of comparative Example IV.

Figure 23:
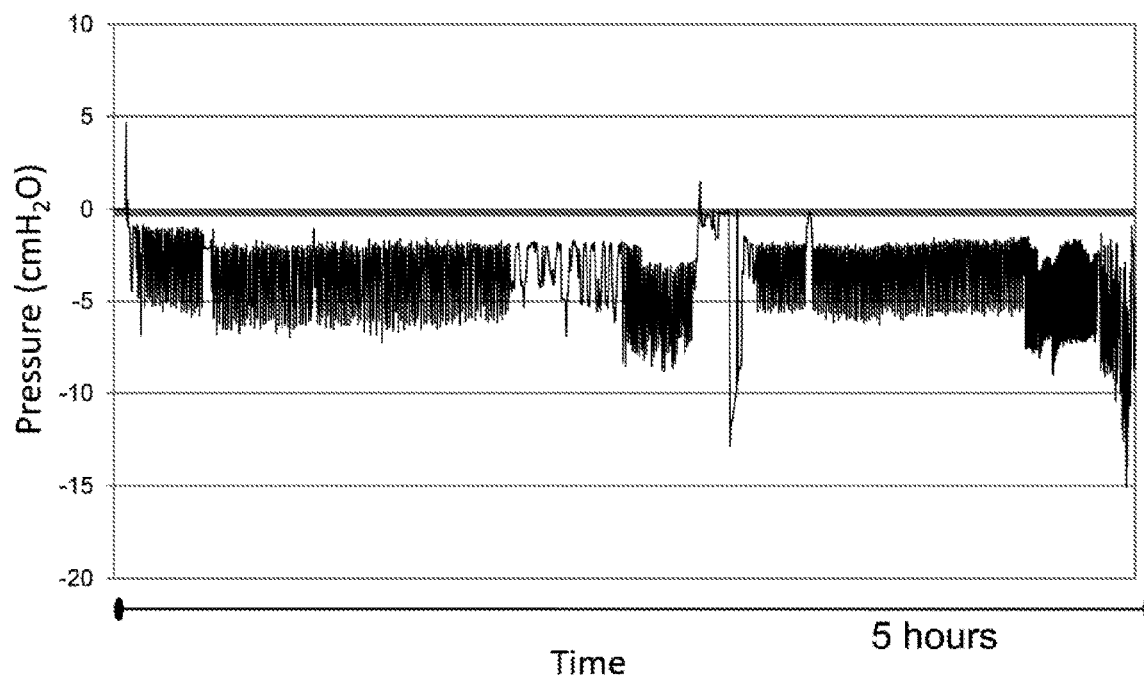
FIG. 23 is a line graph illustrating a representative intrathoracic pressure (ITP) profile over time obtained from the container housing sample porcine lungs ventilated with negative pressure according to an apparatus as depicted in FIG. 22.

FIG. 23 shows that the pressure (ITP, in $cmH_2O$) inside the sealed container of the NPV apparatus 400 in FIG. 22 could be oscillated over time.

Figure 24:
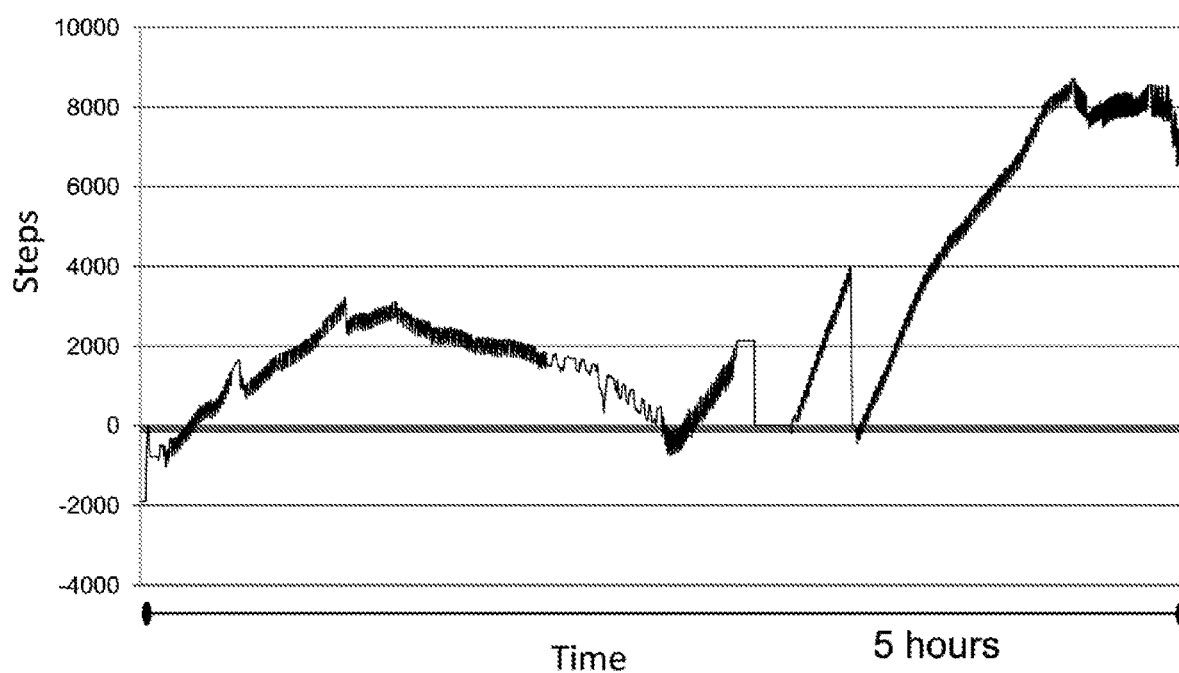
FIG. 24 is a line graph illustrating the step position of the roller pump over time during negative pressure ventilation of sample porcine lungs using the apparatus depicted in FIG. 22.

The volume of the liquid 480 drawn from, or supplied to, the container 410 by roller pump 402 was indicated by the step position of the roller pump 402. Ideally, one might have expected that the volume of liquid 480 withdrawn from and re-supplied to the container 410 during each ventilation cycle should be about the same, and the thus the median step position of the roller pump 402 should remain stable over time. However, as shown in FIG. 24, experimental results indicated that the median step position of the roller pump 402 changed over time. Oscillations of the step position around the median step position resulted in liquid 480 being moved in and out of the container 410 to cause the lung 450 to inspire and expire.

It is believed that some or all of the periods of steadily increasing median step position seen in FIG. 24 resulted from a slight leakage of air into the container 410, which created a significant obstacle to long-term ex vivo ventilation with the NPV apparatus 400.

It is believed that this air leakage was due to imperfections in the seal between the container 410 and the lid 412 (or its ports 414, 416, 418), imperfections in the seal between the endotracheal tube 444 and the lung airway 452, and/or from microscopic ruptures (e.g., bronchopleural fistulae) in the wall of the lungs 450. Such ruptures were, in fact, observed as inferred from the appearance of bubbles in a localized portion of the surface of the lungs. It was observed that, in general, excised lungs often have one or more such rupture.

The slight air leakage into container 410 had the apparent consequence that, in each breathing cycle, the amount of liquid 480 removed from the container 410 could be slightly greater than the amount of liquid 480 returned to the container 410. As a result, the level of liquid 480 in the container 410 could slowly decrease over time, which required that the breathing cycles be stopped, that the conduit 432 be clamped (so as to avoid collapse of the lungs), that the container 410 be opened to the atmosphere to add more liquid 480, and that the step position of the pump 402 be returned to zero. This is the procedure that was followed during the times corresponding to each the two peaks at around 3.5 hr in FIG. 24, where the steady rises in median step position correspond to observed losses of the liquid 480 from the container 410 and the sharp drops correspond to resetting the step position to zero after opening the container and adding back more liquid 480.

In other portions of the experiment in FIGS. 22 to 24, it was unclear why the median step position in FIG. 24 was rising and falling.

By contrast, in an NPV system of the present disclosure, no such problems with pumps or air leakage were encountered, whether with or without the application of PPV into the airway.

Example V

An apparatus and methods described in this disclosure (for example, as shown in FIGS. 3-8) were used for EVLP with positive pressure ventilation (referred to as the "NPV/PPV-EVLP" platform) in a series of experiments on 16 porcine lungs and 3 human lungs. As previously described, the NPV/PPV-EVLP platform used a custom turbine driven ventilator to change the air pressure within the organ chamber. The turbine and accompanying valve mechanism induced a negative pressure within the organ chamber and also delivered positive airway pressure, regulated with a positive-end-expiratory pressure (PEEP) valve.

As a comparator, an additional 16 porcine and 3 human lungs were subjected to the same experimental protocol mutatis mutandis with only PPV (no NPV) provided by a standard ICU ventilator (referred to as the "PPV-EVLP" platform). The ventilator used was the SERVO-I™ provided by Maquet™ Critical Care AB of Solna, Sweden.

For each porcine lung experiment, a pair of lungs was rapidly excised from a 37-47 kg female pig (approx. 2 to 3 months of age) following appropriate euthanasia and exsanguination. The perfusate comprised either an acellular perfusate or a cellular perfusate. The acellular perfusate used was 2 L Krebs-Henseleit buffer with 8% bovine serum albumin and the cellular perfusate used was 1.5 L Krebs-Henseleit buffer with 8% bovine serum albumin+0.5 L packed red blood cells (pRBCs).

Each group of porcine lungs was split into two sub-groups, with eight lungs in each sub-group. The first sub-group (N=8) was perfused with the cellular perfusate with combined NPV/PPV; the second sub-group (N=8) was perfused with the cellular perfusate with PPV; the third sub-group (N=8) was perfused with the acellular perfusate with combined NPV/PPV; and the fourth sub-group (N=8) was perfused with the acellular perfusate with PPV.

For each human lung experiment, a pair of lungs was rapidly excised after brain-stem death of the donor. The characteristics of each human donor lung are presented in Table 2. The perfusate comprised a cellular perfusate (a solution of 1.5 L STEEN Solution™+0.5 L pRBCs was used). All tested human lungs were marginal and rejected for transplant. The human lungs were split into two groups, with three lungs in each group. The first group (N=3) was perfused with the cellular perfusate with combined NPV/PPV and the second group (N=3) was perfused with the cellular perfusate with PPV.

TABLE 2

Characteristics of human donor lungs

| Ventilation | Age (Yrs) | Sex | Donor Weight (kg) | Donor $PO_2/FiO_2$ (mmHg) | Reason for Rejection |
|---|---|---|---|---|---|
| PPV | 72 | M | 80 | 190 | Age > 64; Poor oxygenation (<350 mmHg) |
| PPV | 54 | M | 80 | 270 | High risk donor; Poor oxygenation (<350 mmHg) |
| PPV | 16 | F | 64 | 80 | Poor oxygenation & aspiration (<350 mmHg) |
| NPV/PPV | 80 | F | 80 | 98 | MRSA pneumonia; Poor oxygenation (<350 mmHg) |
| NPV/PPV | 100 | M | 100 | 170 | Size mismatch; Poor oxygenation (<350 mmHg) |
| NPV/PPV | 85 | M | 85 | 145 | Emphysematic; ABO mismatch; Poor oxygenation (<350 mmHg) |

The NPV/PPV-EVLP and PPV-EVLP platforms were primed with 2 liters of the respective experimental perfusate, 10,000 IU heparin, 500 mg of methylprednisolone, and 3.375 g of piperacillin/tazobactam. Both NPV/PPV-EVLP and PPV-EVLP platforms had a centrifugal pump (Medtronic™) that drove continuous flow of perfusate to the pulmonary artery (PA) from the reservoir (for NPV/PPV-EVLP platform, this was integrated in the organ chamber, e.g. chamber 110 of FIG. 3). Perfusate initially passed through a M27 PH.I.S.I.O adult arterial filter (Sorin Group Canada Inc™), then a membrane de-oxygenator (Sorin PrimO2X™) and warmed with a computer controlled heater (PolyScience™), prior to returning to the lungs via the PA. Both platforms had a microcontroller with custom software that controlled the desired PA flow and monitored corresponding physiologic parameters using a flow probe (BIO-Probe Transducer Model TX40™ by Medtronic), pressure transducers (Edwards Lifesciences™), air pressure sensors, and an air flow meter. Data was collected at 10 s intervals. Both platforms utilized compressed medical air, a hypoxic sweep gas mix, (89% $N_2$, 8% $CO_2$, 3% $O_2$), to titrate pre-lung (PA) perfusate gas composition.

For the NPV/PPV-EVLP platform, a computer controlled the proportioning valves and turbine in the apparatus using input from pressure sensors for $P_{IT}$ and $P_{AW}$, as described for FIGS. 3-6. The computer recorded data from the airway flow sensor, as located in FIGS. 3-5, but did not use this information to control the apparatus. The computer was instructed to cause cycles of inspiration and expiration by entering into the computer desired set-points for: inspiratory time ($t_i$), expiratory time ($t_e$), end-inspiratory pressure (EIP) inside the sealed container, end-expiratory pressure (EEP) inside the sealed container, and a constant positive airway pressure.

For the PPV-EVLP platform, a Drager EVITA XL™ ventilator was used to set and control the ventilation parameters.

All lungs were perfused and ventilated for 12 hours. Data on lung mechanics as well as vascular function were collected continuously over the 12 hour period. Perfusate samples were collected at regular intervals to measure dissolved gas content and inflammatory marker levels.

To initiate each experiment in either the NPV/PPV-EVLP and PPV-EVLP platforms, the pulmonary artery (PA) of each lung was cannulated, while the left atrium (LA) was left open, trachea was intubated with an endotracheal tube, and perfusion was initiated at 5% cardiac output (CO) and 20-25° C. (irrespective of experimental ventilation group). Anterograde perfusion was increased to 10% of predicted cardiac output (CO; CO=70 mL/kg/min) and perfusate was gradually warmed to 38° C. over a 60-minute period. The perfusate PA flow was increased by increments of 10% of CO every 20-minutes of perfusion; thus, by T=1 (1 hour into perfusion), a desired flow (preservation mode) of 30% CO was achieved. The initiation parameters used are shown in Table 3.

TABLE 3

Perfusion Initialization Parameters

| Perfusion Time (min.) | 0 | 10 | 20 | 20-40 | 40-50 | 60 (T = 1) |
|---|---|---|---|---|---|---|
| Perfusion Temp (° C.) | 20-30 | 25-30 | 32 | 32-34 | 34-36 | 37.5-38 |
| PA Flow (% CO) | 5 | 10 | 10 | 20 | 30 | 30 |
| Ventilation | None | None | Initiate preservation mode | Preservation mode | Preservation mode | Recruitment phase |
| Medical Gas Mixer | None | None | None | None | None | Start |
| Left Atrial Pressure (LAP; mmHg) | 0 | 0 | 0 | 0 | 0 | 0 |

Experiments in the NPV/PPV-EVLP and PPV-EVLP platforms utilized pressure-control ventilation and flow controlled perfusion. For both platforms, a preservation mode ventilation was initiated once the perfusate temperature reached 32° C. An evaluation ventilation mode (providing higher lung pressure and volume) was utilized for data collection, thereby ensuring that the data collected on gas exchange and compliance was done when the lungs were fully ventilated. The preservation and evaluative modes of ventilation and vascular pressure parameters are listed in Table 4.

TABLE 4

Preservation and Evaluation modes

| | Preservation Ventilation Mode | Evaluation Ventilation Mode |
|---|---|---|
| Temperature (° C.) | 37.5 (Human) 38 (Porcine) | 37.5 (Human) 38 (Porcine) |
| Pulmonary Artery Flow | 30% CO | 50% CO |
| Ventilation Parameters | | |
| Mode | Volume Control | Volume Control |
| Inspiratory Tidal Volume (mL/kg) | 6 | 10 |
| Frequency (bpm) | 7-8 | 10-12 |
| PEEP (cmH$_2$O) | 7 | 5 |
| FiO$_2$ (%) | 21 | 21 |
| Pressure Parameters | | |
| PAP (mmHg) | <20 | <20 |
| LAP (mmHg) | 0 | 0 |
| Medical gas mixer | 89% $N_2$, 8% $CO_2$, 3% $O_2$ | 89% $N_2$, 8% $CO_2$, 3% $O_2$ |
| Medical gas mixer (L/min) titrated to PCO$_2$ (mmHg) | 35-55 | 35-50 |

With the NPV/PPV-EVLP platform, to obtain the desired inspiratory tidal volumes, the pleural pressure was varied between a negative end-inspiratory-pressure (EIP) and an end-expiratory-pressure (EEP) that was slightly greater than airway pressure (Paw). The transpulmonary air pressure (TPG) was calculated: TPG=Paw−EIP. Evaluation was conducted serially every 2 hours, with upper peak airway pressure limit set to 25 cmH$_2$O.

Sweep gas flow rate through the hollow fiber deoxygenator was titrated to maintain a physiological pH of 7.35-7.45 and PCO$_2$ (35-50 mmHg). Insulin (2.0 U/h) and glucose (1.0 g/h) were infused over the duration of EVLP.

For the first 3-hours of EVLP, the PEEP was maintained at 7 cmH$_2$O with inspiratory holds performed every 30 minutes for three consecutive breaths (5-10 seconds/breath).

FIGS. 25A to 31C present data derived from experiments on lungs perfused with NPV/PPV-EVLP and lungs perfused with PPV-EVLP. In all of these figures, the pressures are all relative to atmospheric pressure (i.e., atmospheric pressure was 0 cmH$_2$O).

Mean pulmonary artery pressure (mPAP), pulmonary vascular resistance (PVR), dynamic compliance (Cdyn), peak airway pressure (PAWP), and ratio of arterial partial pressure of oxygen to the oxygen fraction in inspired air (PO$_2$/FiO$_2$ or P/F ratio) were measured during the evaluative time points.

Figure 25A:
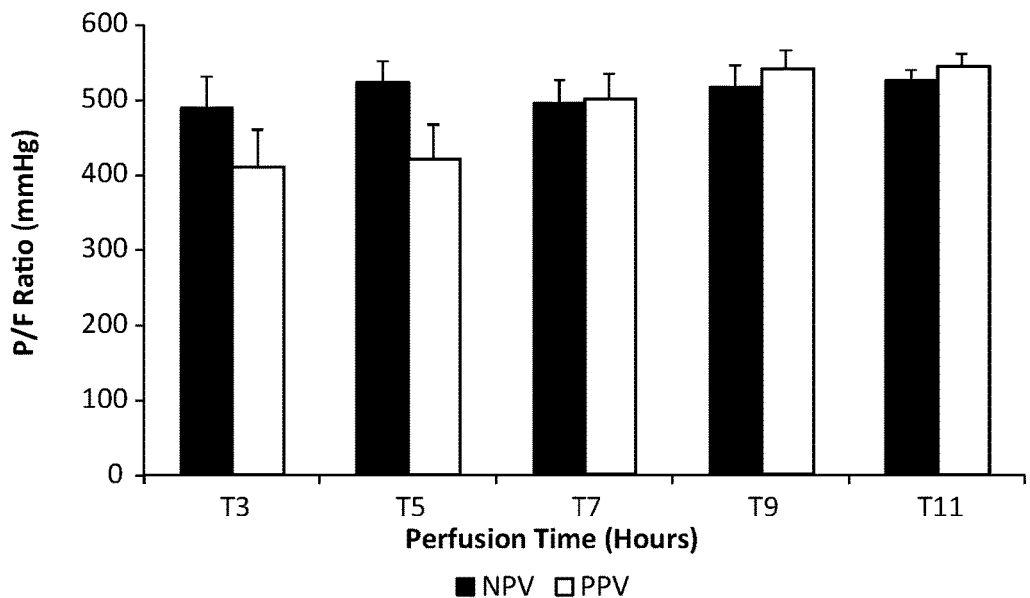
FIGS. 25A, 25B, and 25C are bar graphs illustrating representative results of measurements of lung oxygenation of perfused sample lungs over time, with combined NPV/PPV or PPV.
Figure 25B:
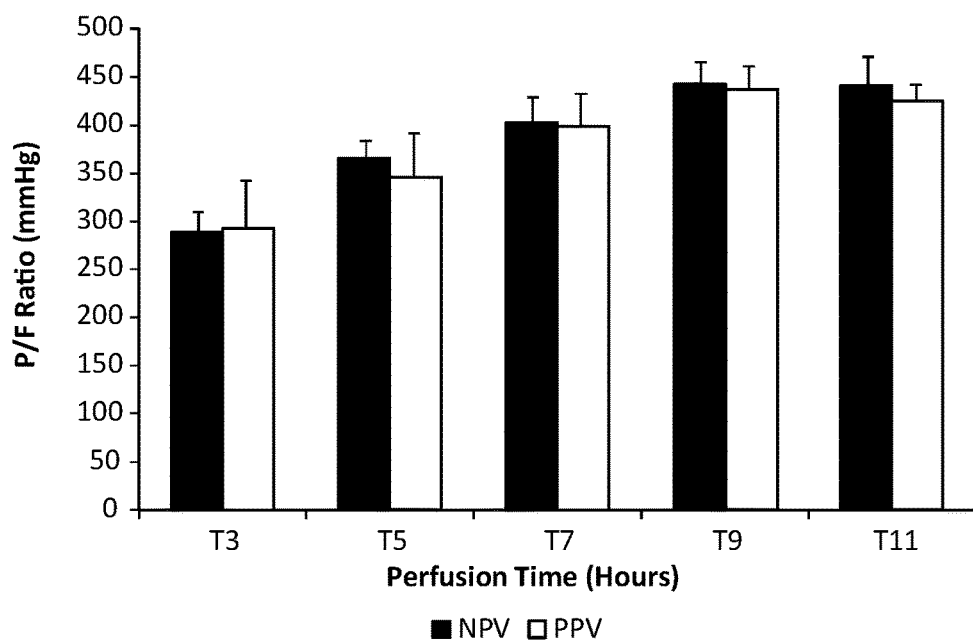
Figure 25C:
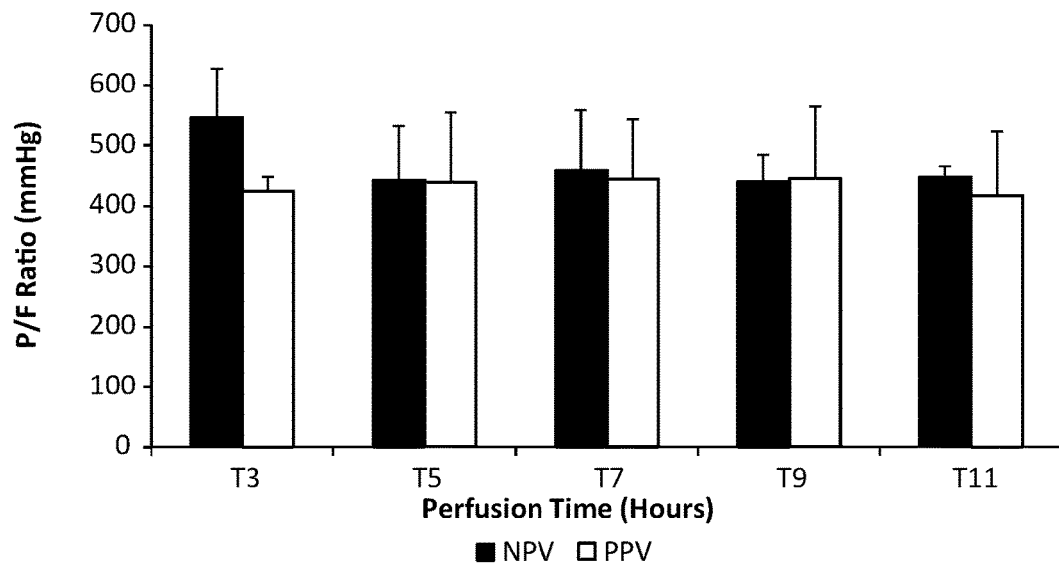

FIGS. 25A, 25B, and 25C illustrate results of measurements of lung oxygenation (i.e. the PO$_2$/FiO$_2$ ratio or the P/F ratio, measured in mmHg) of the perfused lungs over time for lungs perfused with combined NPV/PPV and lungs perfused with PPV. In particular, FIG. 25A illustrates results of the porcine lungs perfused with acellular perfusate; FIG. 25B illustrates results of the porcine lungs perfused with cellular perfusate; and FIG. 25C illustrates results of the human lungs perfused with cellular perfusate. The results illustrate that lung oxygenation remained at an acceptable level of more than 400 mmHg for both porcine and human lungs perfused with combined NPV/PPV or PPV. There was no statistically significant (i.e. p>0.05) difference in lung oxygenation between lungs perfused with either type of perfusate and between lungs perfused with either ventilation platform. However, only lungs perfused with the cellular perfusate demonstrated a statistically significant improvement in oxygenation over time.

Figure 26A:
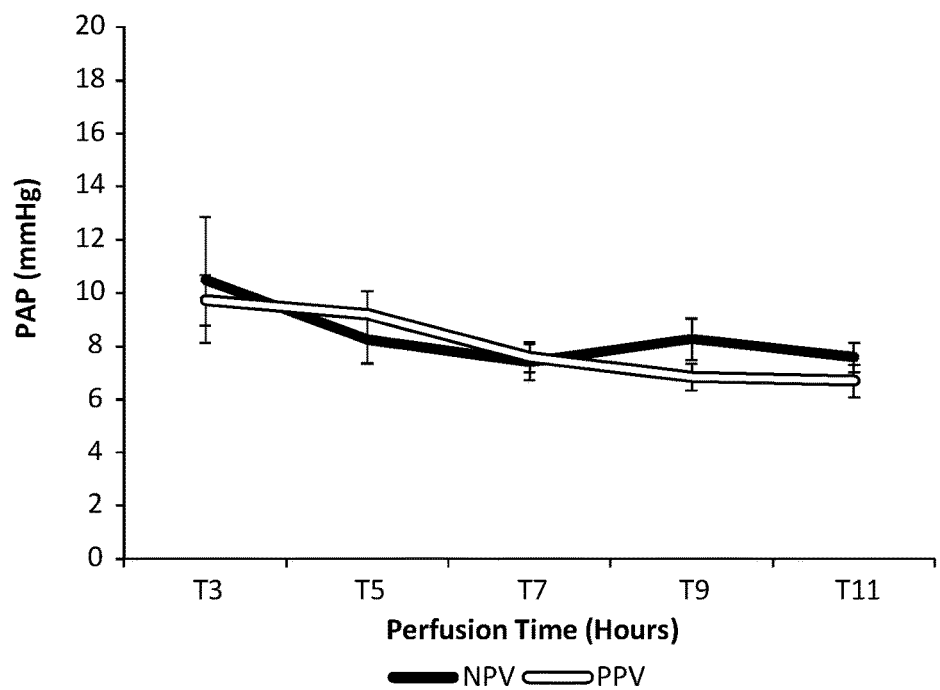
FIGS. 26A, 26B, and 26C are line graphs illustrating representative results of measurements of mean pulmonary arterial pressure of perfused sample lungs over time, with combined NPV/PPV or PPV.
Figure 26B:
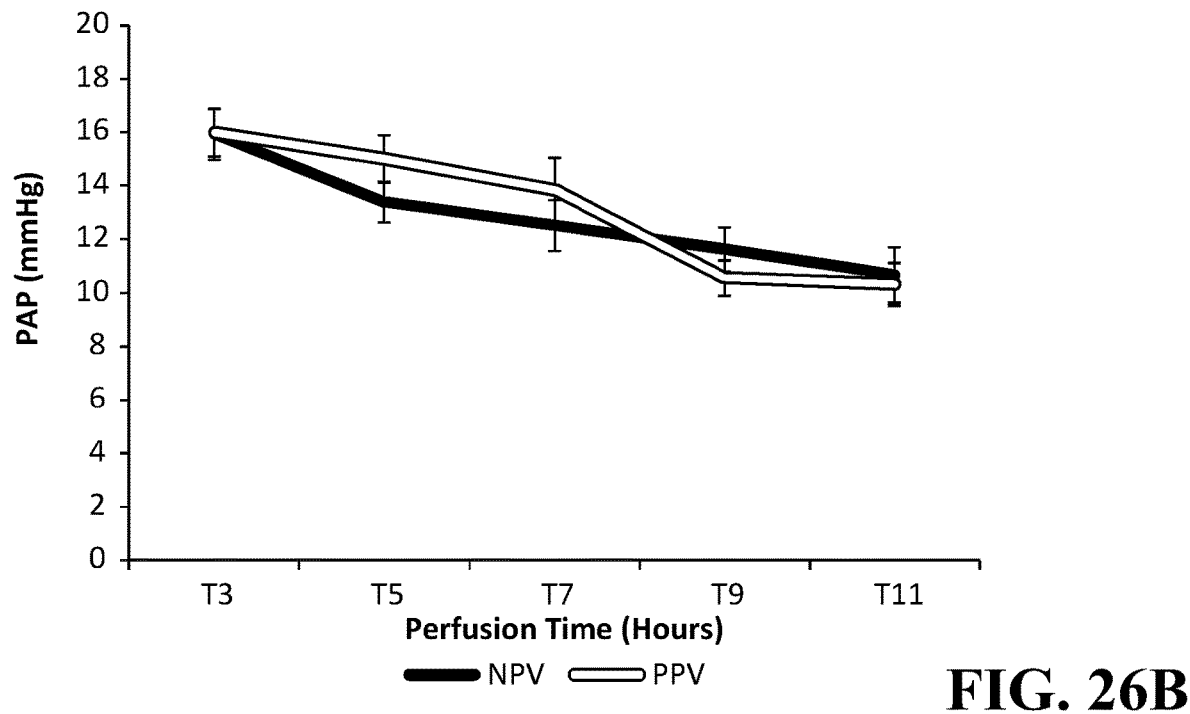
Figure 26C:
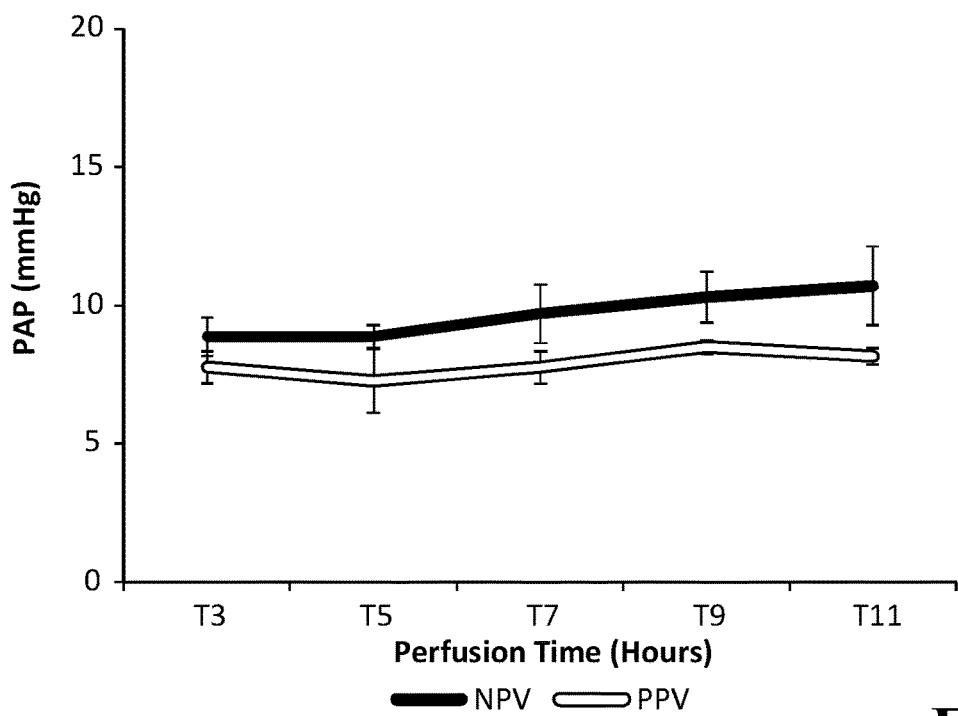
Figure 27A:
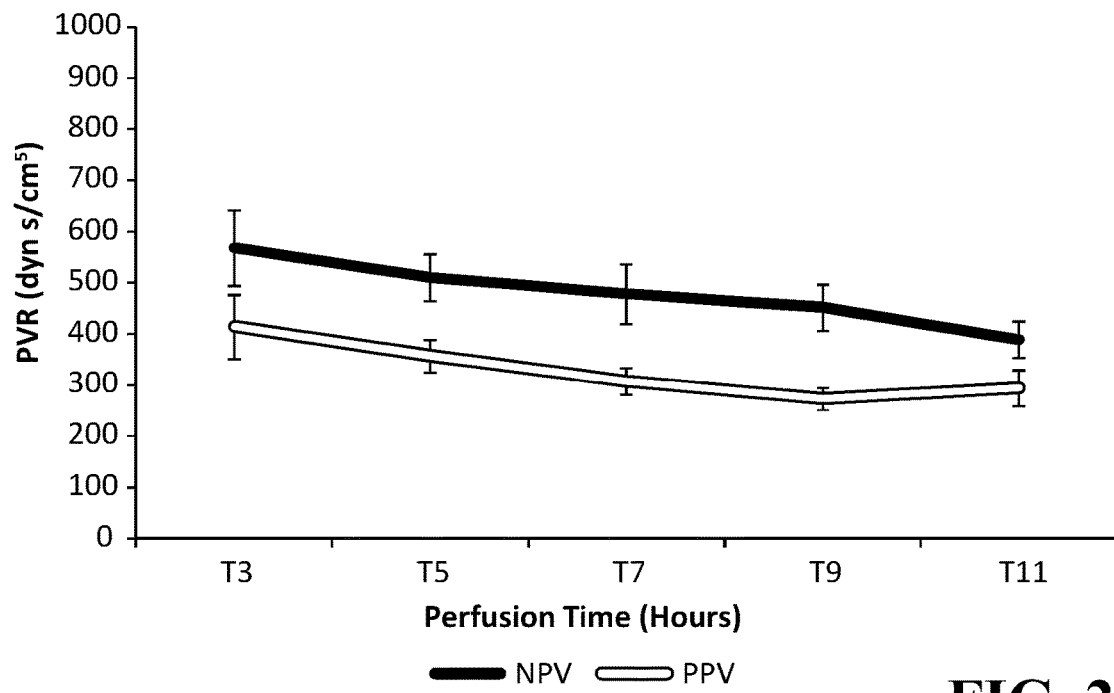
FIGS. 27A, 27B, and 27C are line graphs illustrating representative results of measurements of pulmonary vascular resistance of perfused sample lungs over time, with combined NPV/PPV or PPV.
Figure 27B:
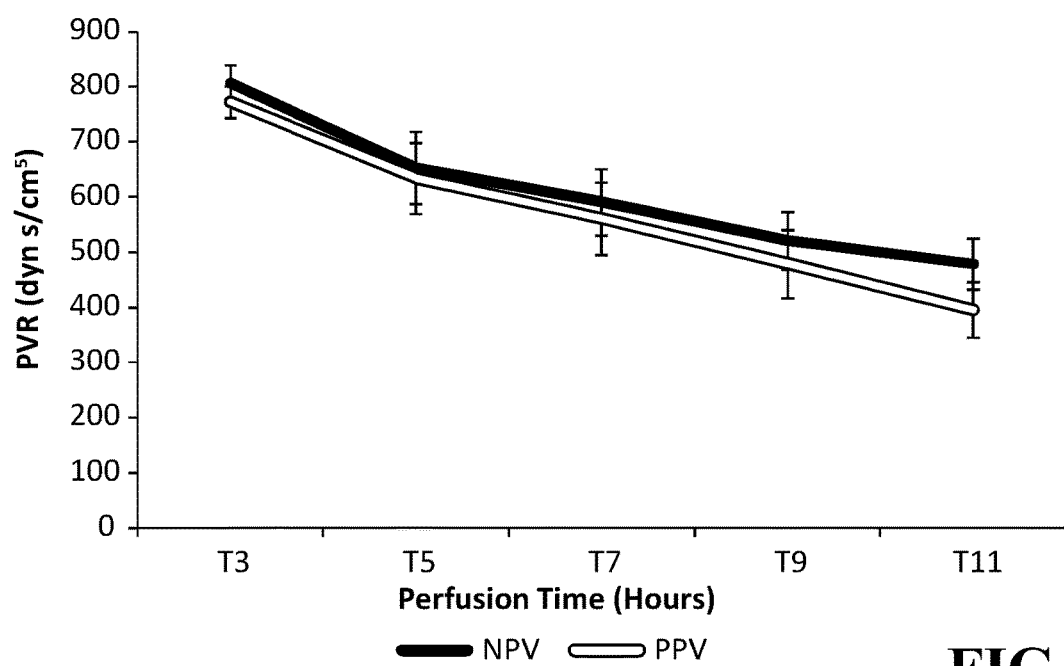
Figure 27C:
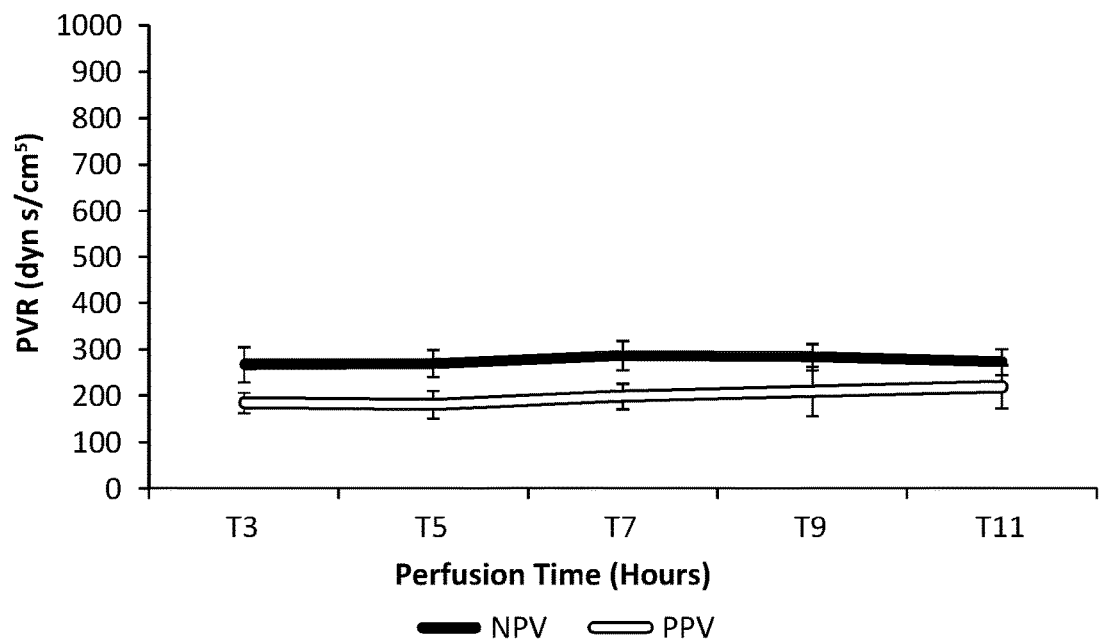

FIGS. 26A, 26B, and 26C illustrate results of measurements of mean pulmonary arterial pressure (mPAP; measured in mmHg) of the perfused lungs over time for lungs perfused with combined NPV/PPV and lungs perfused with PPV. In particular, FIG. 26A illustrates results of the porcine lungs perfused with acellular perfusate; FIG. 26B illustrates results of the porcine lungs perfused with cellular perfusate; and FIG. 26C illustrates results of the human lungs perfused with cellular perfusate. Similarly, FIGS. 27A, 27B, and 27C illustrate results of measurements of pulmonary vascular resistance (PVR; measured in dyn s/cm$^5$) of the perfused lungs over time for lungs perfused with combined NPV/PPV and lungs perfused with PPV. In particular, FIG. 27A illustrates results of the porcine lungs perfused with acellular perfusate; FIG. 27B illustrates results of the porcine lungs perfused with cellular perfusate; and FIG. 27C illustrates results of the human lungs perfused with cellular perfusate. As shown in FIGS. 26A-27C, all the porcine lungs demonstrated a statistically significant decline in mPAP and PVR. However, there was no statistically significant difference in results between lungs perfused with combined NPV/PPV and lungs perfused with PPV. Further, there was no statistically significant change over time in mPAP and PVR for human lungs perfused with either PPV or combined NPV/PPV (see FIGS. 26C and 27C respectively).

Figure 28A:
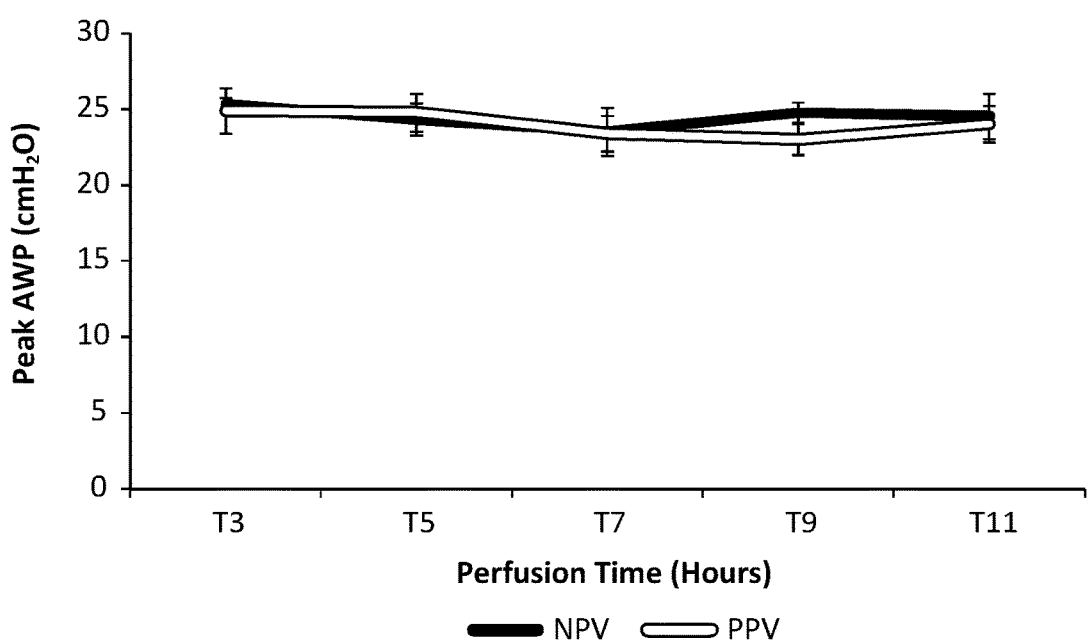
FIGS. 28A, 28B, and 28C are line graphs illustrating results of measurements of peak airway pressure of perfused sample lungs over time, with combined NPV/PPV or with PPV.
Figure 28B:
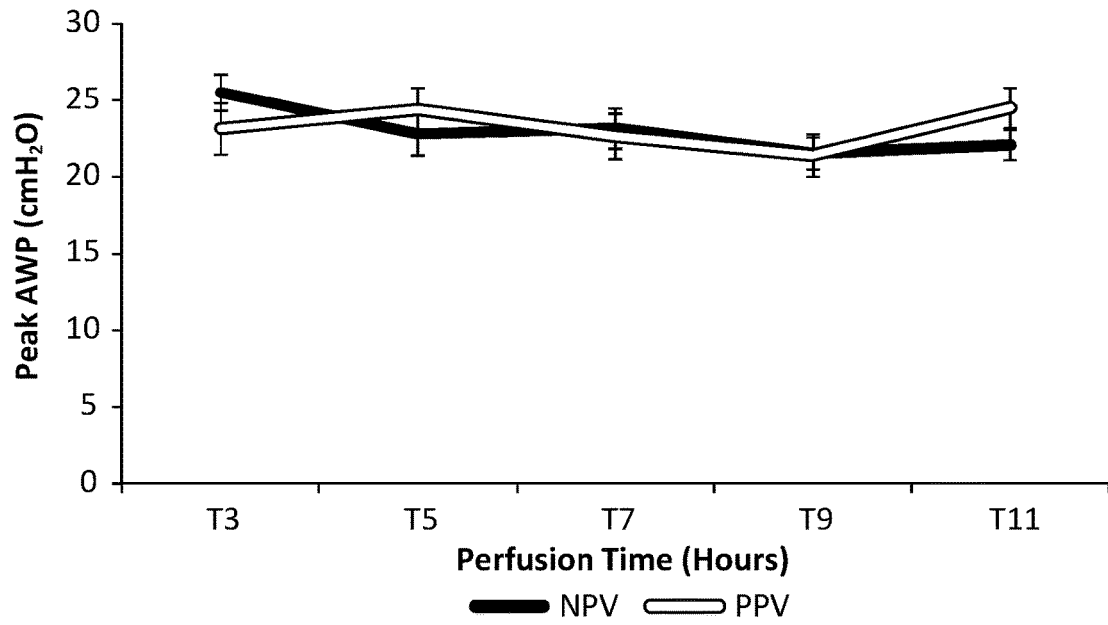
Figure 28C:
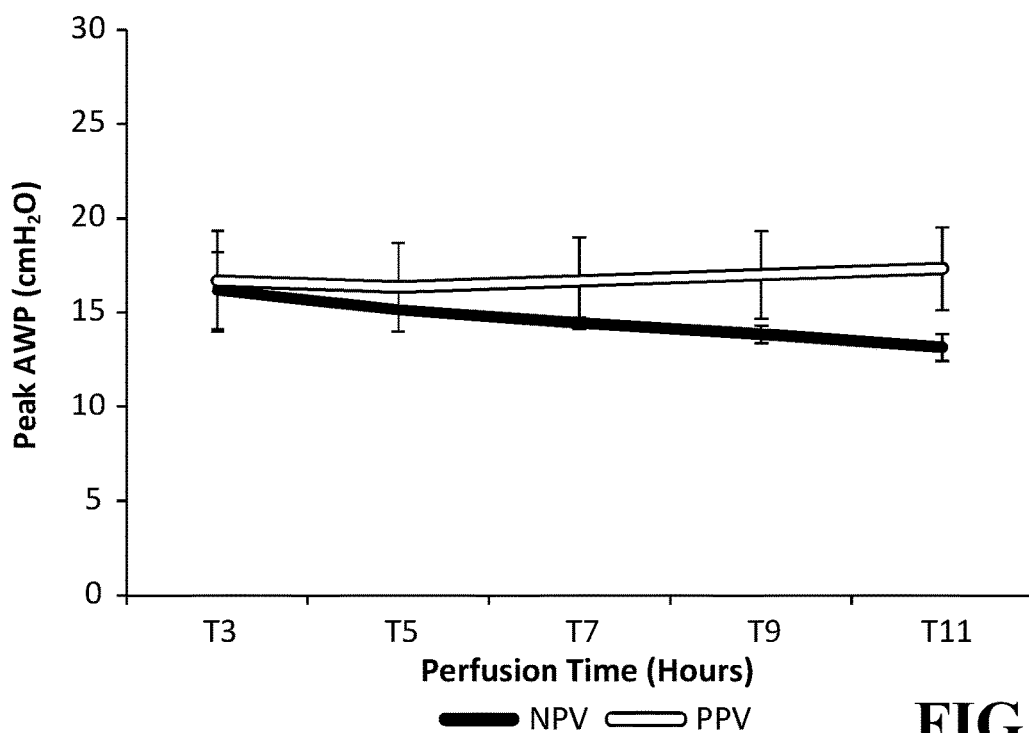

FIGS. 28A, 28B, and 28C illustrate results of measurements of peak airway pressure ($P_{AWP}$; measured in cmH$_2$O) of the perfused lungs over time for lungs perfused with combined NPV/PPV and lungs perfused with PPV. In particular, FIG. 28A illustrates results of the porcine lungs perfused with acellular perfusate; FIG. 28B illustrates results of the porcine lungs perfused with cellular perfusate; and FIG. 28C illustrates results of the human lungs perfused with cellular perfusate. In all cases (porcine-cellular, porcine-acellular, and human-cellular), there was no statistically significant difference in $P_{AWP}$ between lungs perfused with combined NPV/PPV and lungs perfused with PPV. However, as shown in FIG. 28B, $P_{AWP}$ showed a statistically significant decrease over time for porcine lungs perfused with cellular perfusate and combined NPV/PPV.

Figure 29A:
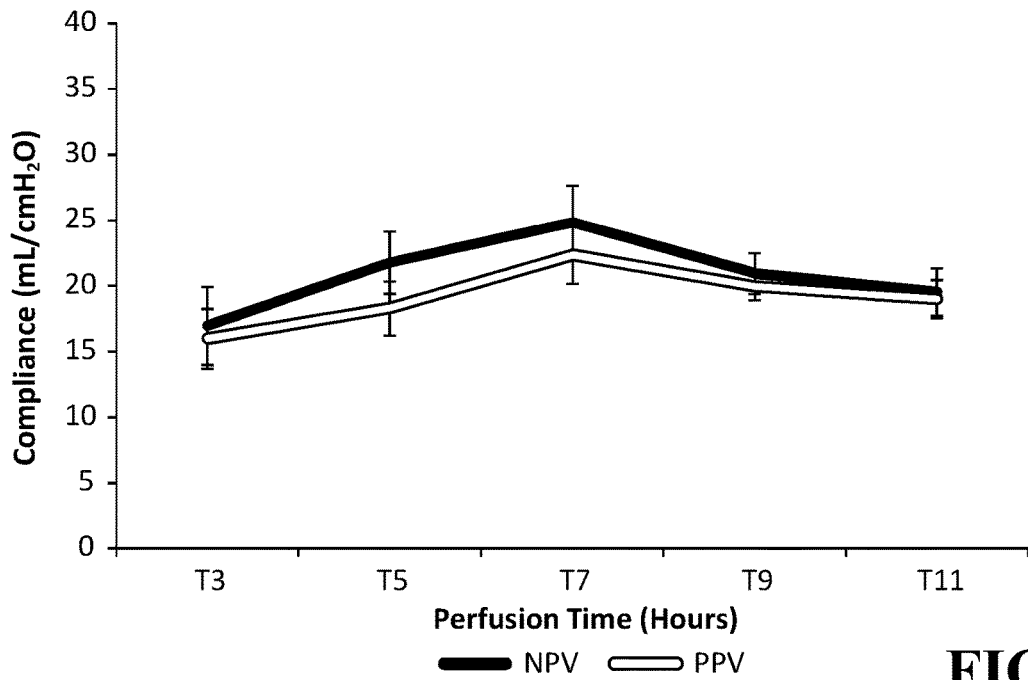
FIGS. 29A, 29B, and 29C are line graphs illustrating representative results of measurements of dynamic compliance of perfused sample lungs over time, with combined NPV/PPV or PPV.
Figure 29B:
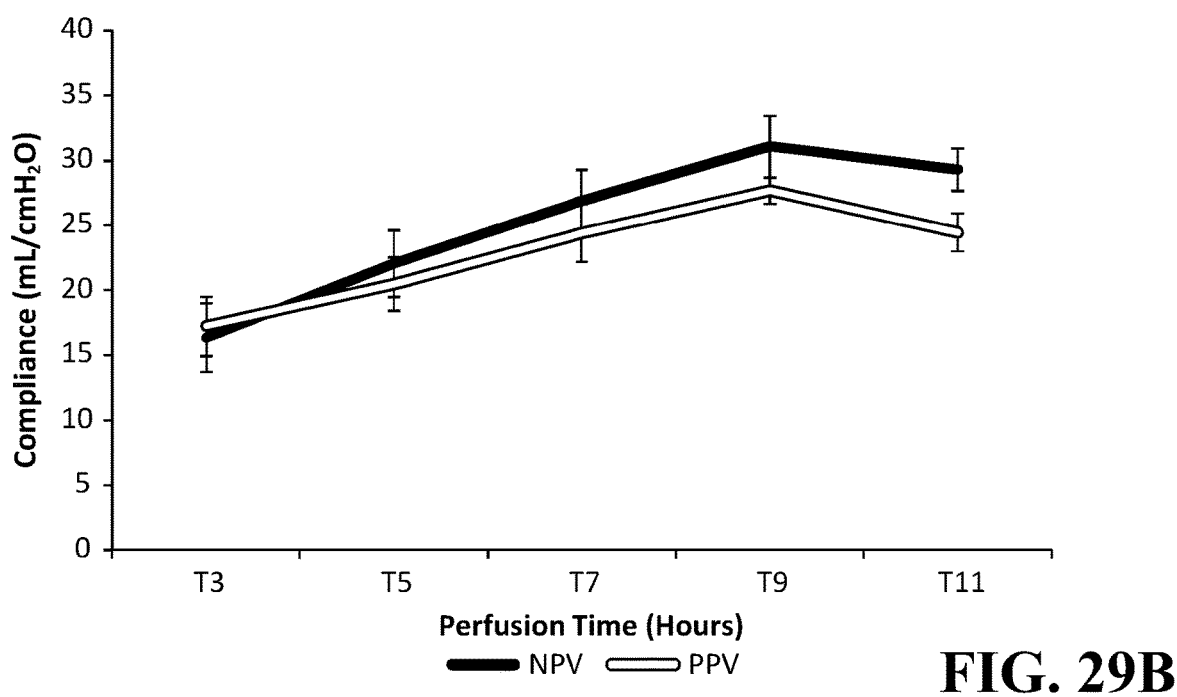
Figure 29C:
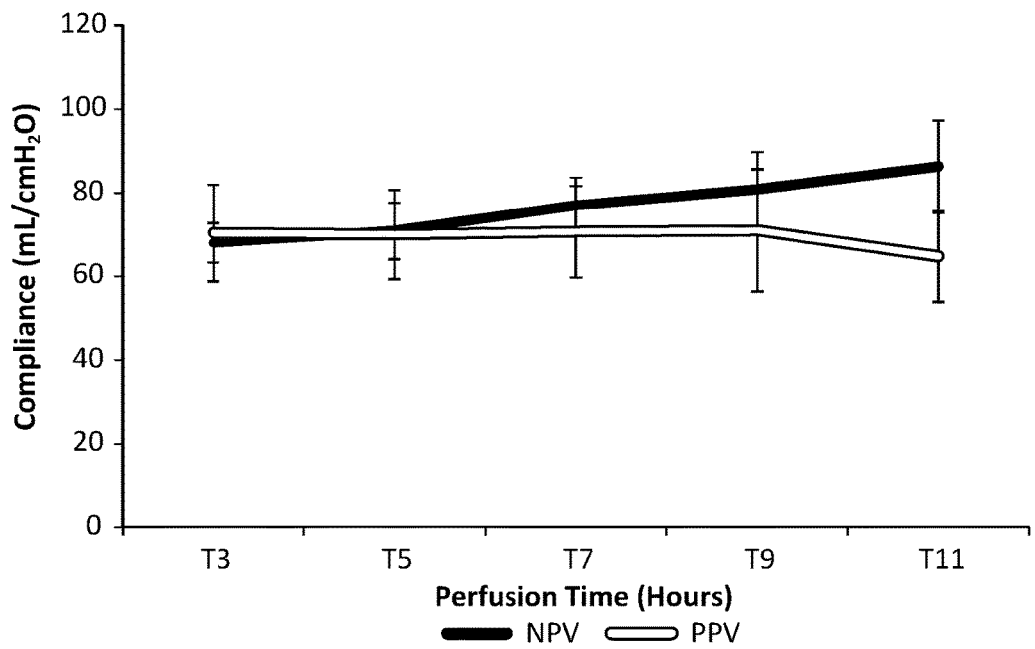

FIGS. 29A, 29B, and 29C illustrate results of measurements of dynamic compliance ($C_{dyn}$; measured in mL/cmH$_2$O) of the perfused lungs over time for lungs perfused with combined NPV/PPV and lungs perfused with PPV. In particular, FIG. 29A illustrates results of the porcine lungs perfused with acellular perfusate; FIG. 29B illustrates results of the porcine lungs perfused with cellular perfusate; and FIG. 29C illustrates results of the human lungs perfused with cellular perfusate. Porcine lungs perfused with the cellular perfusate demonstrated a statistically significant improvement in compliance over time (FIG. 29B). For example, as shown in FIG. 29B at T=11, the $C_{dyn}$ for lungs perfused with combined NPV/PPV was 29.3±1.6 mL/cmH$_2$O and the $C_{dyn}$ for lungs perfused with PPV was 24.5±1.5 mL/cmH$_2$O. However, the same trend was not observed in porcine lungs perfused with acellular perfusate (FIG. 29C), irrespective of the ventilation platform. In contrast, perfused human lungs demonstrated statistically significantly improving compliance over time only when perfused with combined NPV/PPV.

Pro-inflammatory cytokine profiles (including tumor necrosis factor-α (TNFα), interleukin-6 (IL-6), and interleukin-8 (IL-8)) were analyzed using enzyme-linked immunosorbent assay (ELISA) kits provided by R&D Systems™.

Figure 30A:
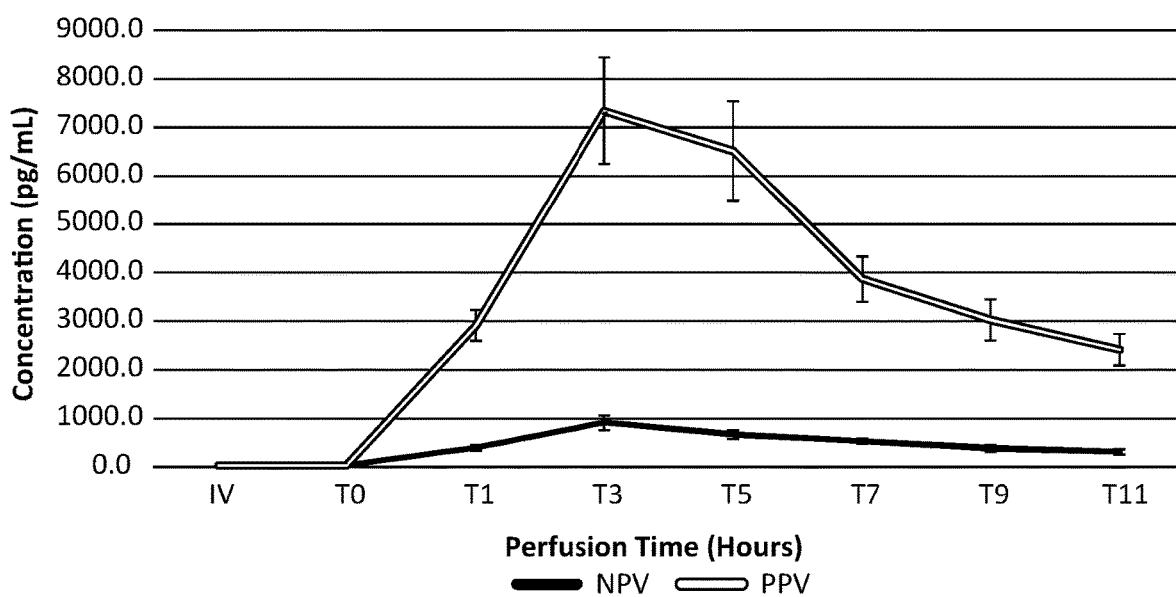
FIGS. 30A, 30B, 30C, 30D, 30E, and 30F are line graphs illustrating representative results of measurements of inflammatory cytokine of perfused sample porcine lungs over time, with combined NPV/PPV or PPV.
Figure 30B:
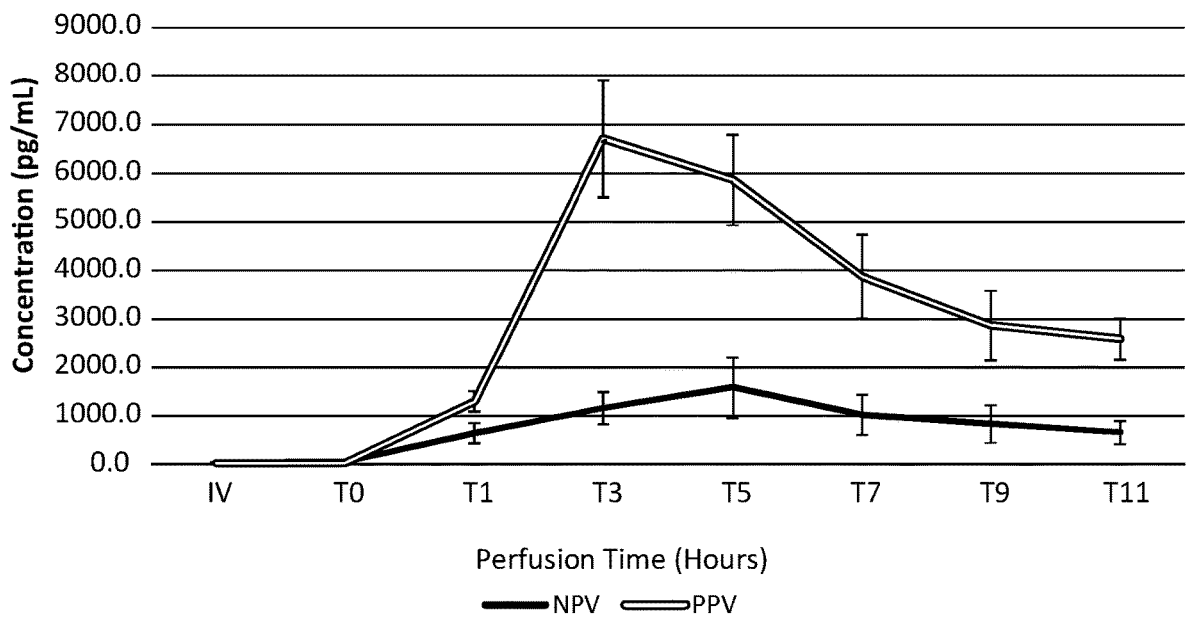
Figure 30C:
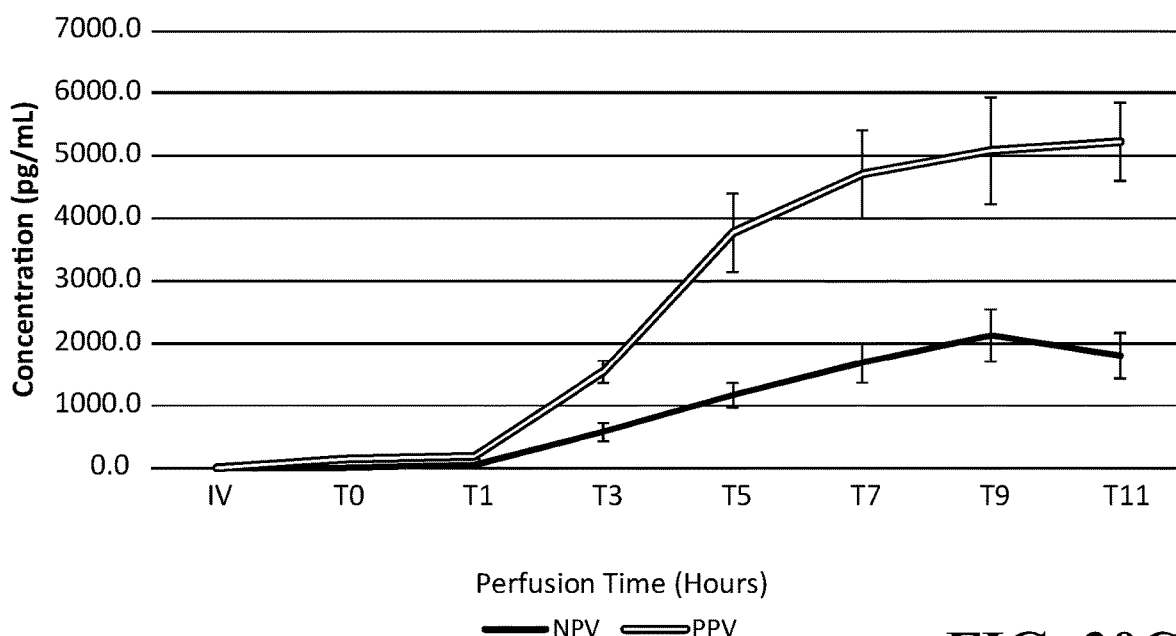
Figure 30D:
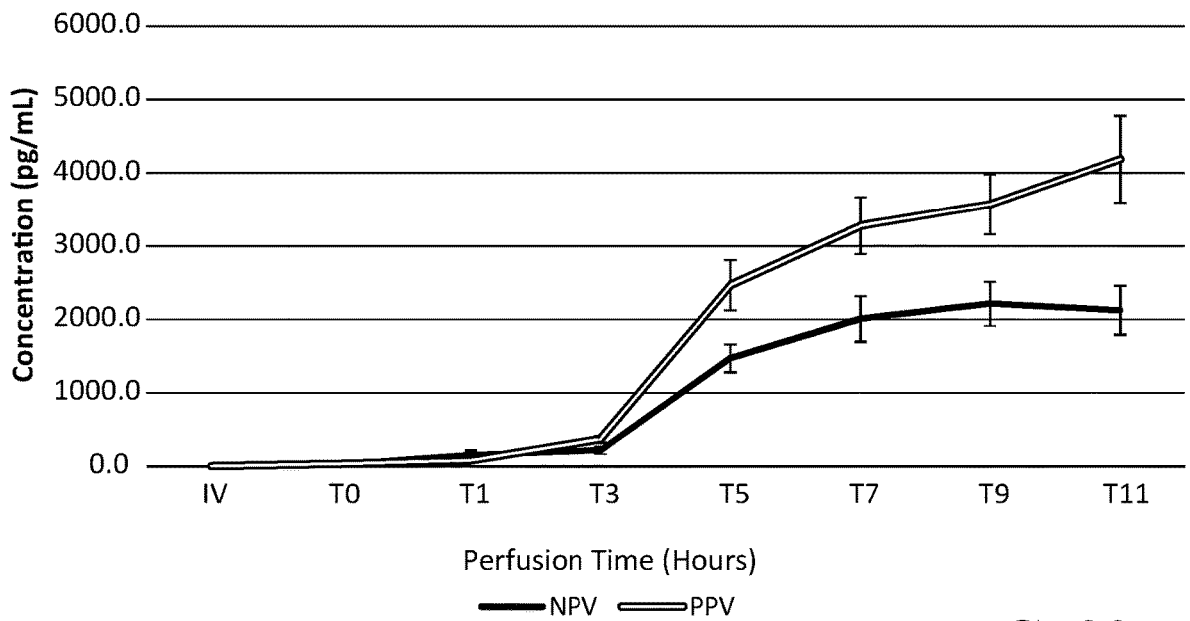
Figure 30E:
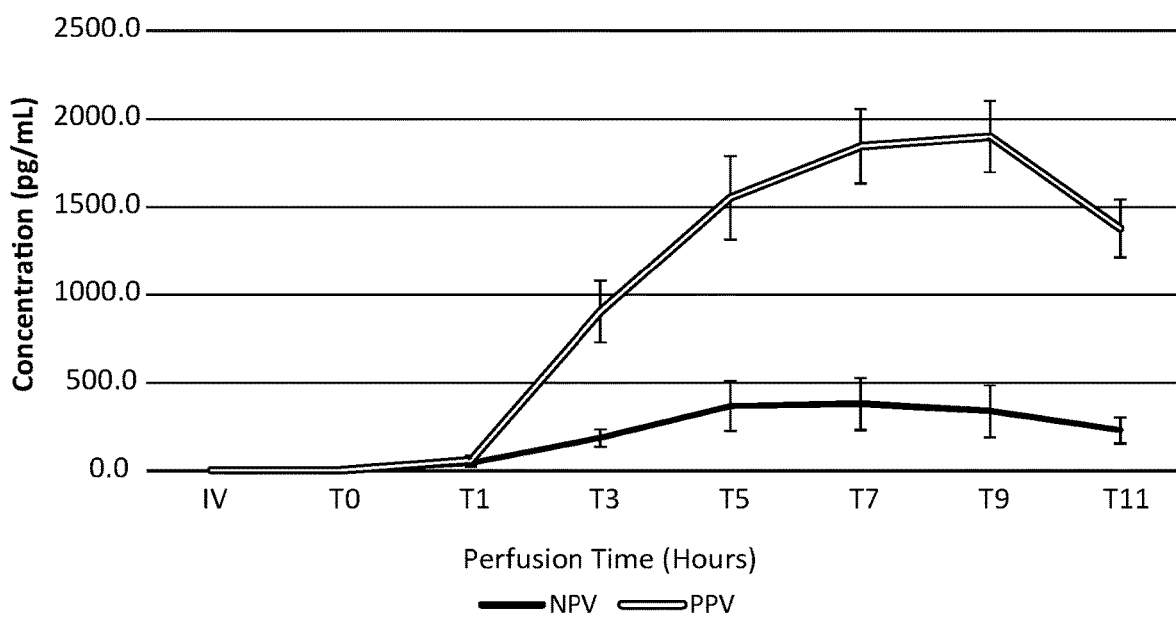
Figure 30F:
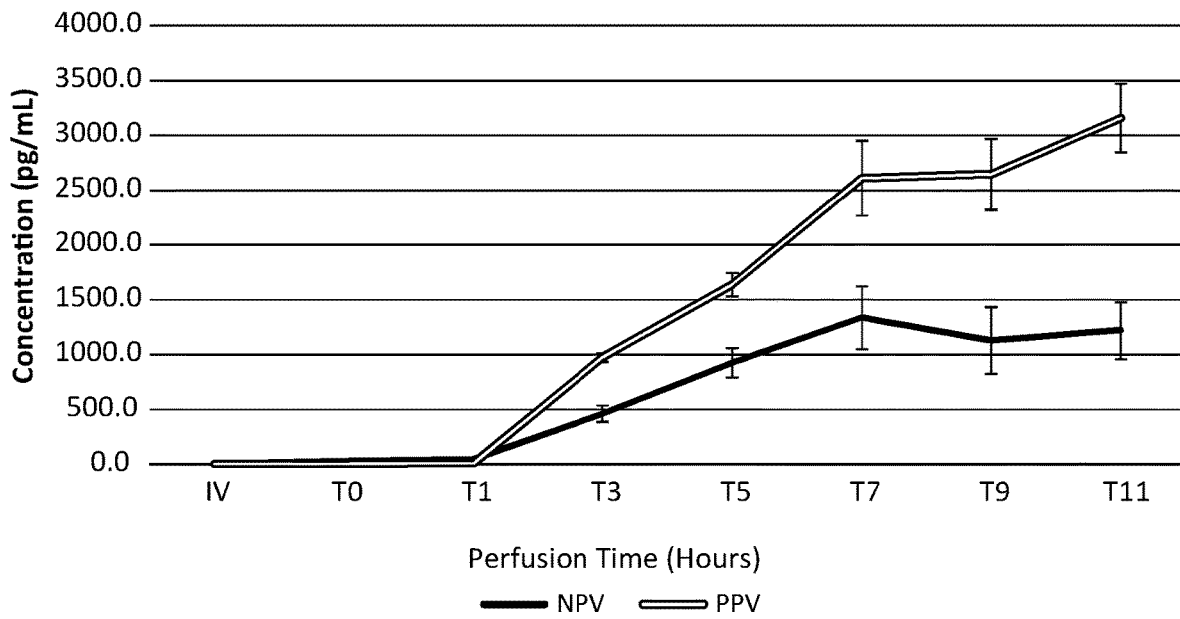

FIGS. 30A-30F illustrate results of measurements of inflammatory cytokine of the perfused porcine lungs over time for lungs perfused with combined NPV/PPV and lungs perfused with PPV. FIGS. 30A and 30B show the concentration, in pg/mL, of tumor necrosis factor alpha (TNFα) for lungs perfused with the cellular perfusate and for lungs perfused with the acellular perfusate, respectively; FIGS. 30C and 30D show the concentration, in pg/mL, of Interleukin 6 (IL-6) for lungs perfused with the cellular perfusate and for lungs perfused with the acellular perfusate, respectively; and FIGS. 30E and 30F show the concentration, in pg/mL, of Interleukin 8 (IL-8) for lungs perfused with the cellular perfusate and for lungs perfused with the acellular perfusate, respectively. As shown in FIGS. 30A-30F, a statistically significantly lower pro-inflammatory cytokine production in porcine lungs perfused with combined NPV/PPV irrespective of the perfusate used was observed.

Figure 31A:
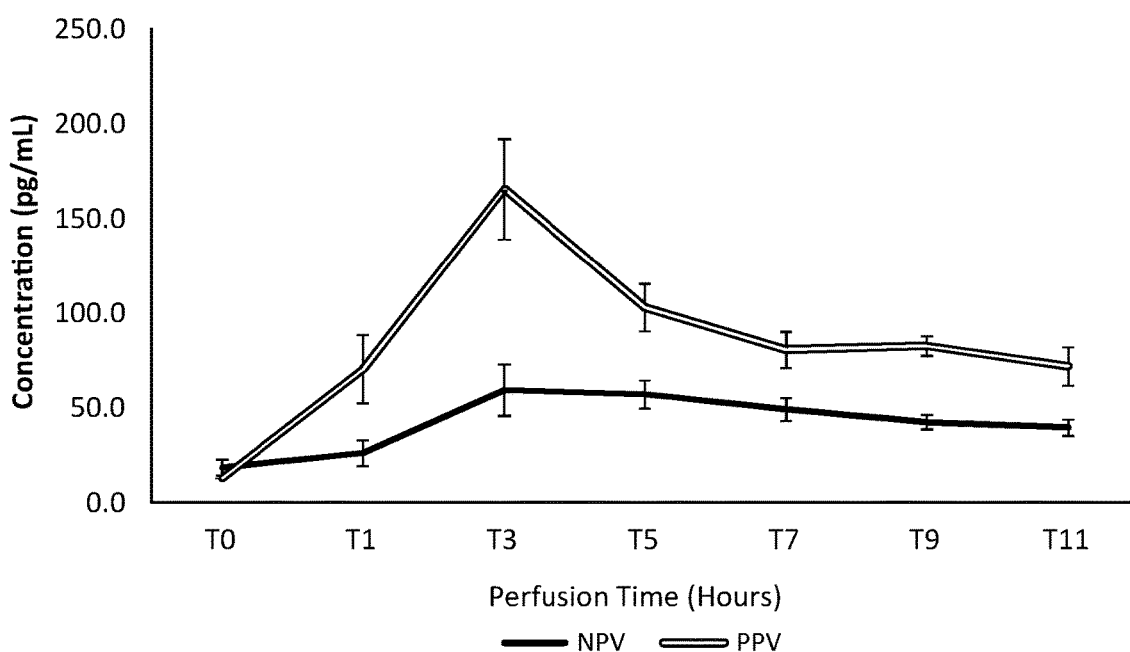
FIGS. 31A, 31B, and 31C are line graphs illustrating representative results of measurements of inflammatory cytokine of perfused sample human lungs over time, with combined NPV/PPV or PPV.
Figure 31B:
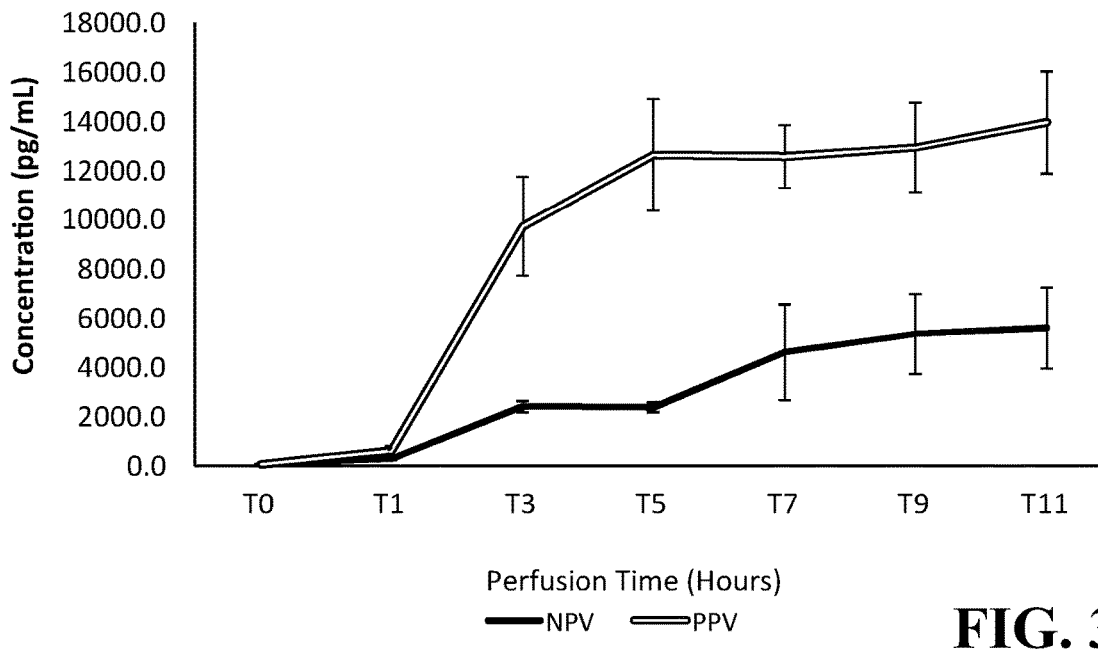
Figure 31C:
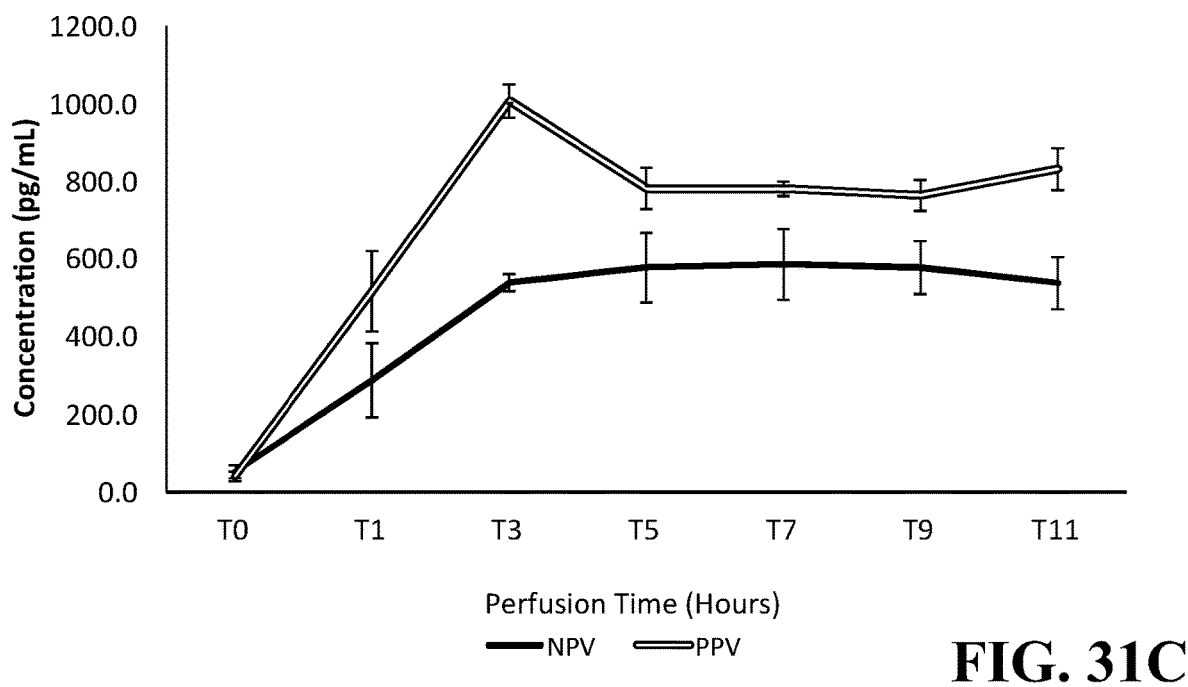

Similarly, FIGS. 31A-31C illustrate results of measurements of inflammatory cytokine of the perfused human lungs over time for lungs perfused with combined NPV/PPV and lungs perfused with PPV. FIG. 31A shows the concentration, in pg/mL, of tumor necrosis factor alpha (TNFα); FIG. 31B shows the concentration, in pg/mL, of Interleukin 6 (IL-6); and FIG. 31C shows the concentration, in pg/mL, of Interleukin 8 (IL-8). As shown in FIGS. 31A and 31B, at all times there a statistically significantly lower TNFα and IL-6 production in human lungs perfused with combined NPV/PPV than those perfused with PPV was observed. However, as shown in FIG. 31C, observed was a statistically significantly lower IL-8 production in human lungs perfused with combined NPV/PPV than in human lungs perfused with PPV only at T=3 and T=11.

Bullae formation during EVLP was counted at T=12. Human lungs perfused with PPV and human lungs perfused with combined NPV/PPV did not develop bullae. For porcine lungs, bullae were counted at 21.4% for lungs perfused with combined NPV/PPV, and 63.8% for lungs perfused with PPV. Accordingly, among perfused porcine lungs, there was 42% lower incidence of bullae formation in lungs perfused with combined NPV/PPV in contrast to those perfused with PPV. A lower bullae formation for porcine lungs perfused with combined NPV/PPV compared with lungs perfused with PPV was observed.

Lungs were also weighed before and after EVLP to calculate the global edema as a weight gain percentage. At T=12, there was less edema formation (i.e. weight gain) in porcine lungs perfused with combined NPV/PPV relative to those perfused with PPV for both perfusates (For cellular perfusate, contrast 20.1±4.1% of edema formation for combined NPV/PPV with 39.0±6.6% of edema formation for PPV; and for acellular perfusate, contrast 40.4±5.3% of edema formation for combined NPV/PPV with 88.1±11.0% of edema formation for PPV).

For human lungs, a drying effect (i.e. a weight reduction) was observed for lungs perfused with combined NPV/PPV in contrast with an edema formation (i.e. weight gain) for lungs perfused with PPV (contrast −8.0±2.1% for combined NPV/PPV with +39.4±5.7% of edema formation for PPV). The reduction in lung weight from baseline suggests that perfusion of human lungs with combined NPV/PPV may help reverse the state of lung edema that had occurred in a donor lung. In particular, since the human lungs used in Example V were fragile/marginal (as they were obtained from rejected donors and had varying degree of lung injury), perfusion with combined NPV/PPV may transform a fragile/marginal into a suitable lung for donation.

Human peripheral lung tissue biopsies were collected at the end of EVLP (T=12). Biopsies were fixed in 10% buffered formalin for 24 hours, embedded in paraffin, sectioned at 5-µm thickness, stained by hematoxylin-eosin (H&E), and examined for pathological changes with light microscopy. Representative photomicrographs of human lung tissue were obtained after T=12 hours of EVLP (not shown). A blinded pulmonary pathologist graded the lung sections in a randomized fashion to assess the histopathological grading of acute lung injury. The histopathological grading of acute lung injury was calculated in accordance with the methods set out in Mehaffey J H, Charles E J, Sharma A K, et al, "Airway pressure release ventilation during ex vivo lung perfusion attenuates injury", J Thorac Cardiovasc Surg 2017; 153: 197-204 and Tane S, Noda K, Shigemura N, "Ex Vivo Lung Perfusion: A Key Tool for Translational Science in the Lungs", Chest 2017.

Overall, a lower acute lunge injury was observed by histopathology for human lungs perfused with combined NPV/PPV in comparison with lungs perfused with PPV. For example, the interstitial edema histological score for the lung perfused with combined NPV/PPV was determined to be 1.5, whereas for the lung perfused with PPV, the histological score was determined to be 2.7. Further, the alveolar inflammation histological score for the lung perfused with combined NPV/PPV was determined to be 1.5, whereas for the lung perfused with PPV, the histological score was determined to be 2.7. Further, the amount of neutrophilic infiltrates for the lung perfused with combined NPV/PPV was statistically significantly lower (observed to have an infiltration density of 6.3) than the amount of neutrophilic infiltrates for the lung perfused with PPV (observed to have an infiltration density of 14.8). Further, the interstitial inflammation histological score for the lung perfused with combined NPV/PPV was determined to be 1.2, whereas for the lung perfused with PPV, the histological score was determined to be 1.7 (which was not statistically significant; $p>0.05$). Further, the hemorrhage histological score for the lung perfused with combined NPV/PPV was determined to be 0.0, whereas for the lung perfused with PPV, the histological score was determined to be 0.7 (which was also not statistically significant; $p>0.05$). Further, the perivascular neutrophil infiltration density was observed to be 0.6 for the lung perfused with combined NPV/PPV, and 1.6 for the lung perfused with PPV.

The results obtained from Example V (outlined above) suggest that lungs perfused with the NPV/PPV-EVLP platform may suffer lower rates of ventilator induced lung injury (VILI). Lungs perfused with combined NPV/PPV were observed to have stable and acceptable physiologic parameters over 12 hours of EVLP. The physiologic parameters for lungs perfused with combined NPV/PPV were observed to be similar to those of lungs perfused with PPV (see, for example, FIGS. 25A-27C).

Further, lungs perfused with combined NPV/PPV were observed to have superior results in comparison with lungs perfused with PPV. For example, lungs perfused with combined NPV/PPV were observed to have a decreased production of pro-inflammatory cytokines compared to lungs perfused with PPV (FIGS. 30A-31C), a decreased incidence of bullae formation compared to lungs perfused with PPV, and decreased lung edema in both porcine and human lungs compared to lungs perfused with PPV. Further, human lungs perfused with combined NPV/PPV were observed to have a decreased histopathologic finding of acute lung injury compared to lungs perfused with PPV. Accordingly, while the physiologic parameters over 12 hours of EVLP were similar for lungs perfused with combined NPV/PPV to lungs perfused with PPV, the lungs perfused with PPV were observed to have a sub-clinical deterioration in quality.

CONCLUDING REMARKS

Selected Embodiments of the present invention may be used in a variety of fields and applications. For example, they may have applications in transplantation surgery and research.

Other features, modifications, and applications of the embodiments described here may be understood by those skilled in the art in view of the disclosure herein.

It will be understood that any range of values herein is intended to specifically include any intermediate value or sub-range within the given range, and all such intermediate values and sub-ranges are individually and specifically disclosed.

The word "include" or its variations such as "includes" or "including" will be understood to imply the inclusion of a stated integer or groups of integers but not the exclusion of any other integer or group of integers.

It will also be understood that the word "a" or "an" is intended to mean "one or more" or "at least one", and any singular form is intended to include plurals herein.

It will be further understood that the term "comprise", including any variation thereof, is intended to be open-ended and means "include, but not limited to," unless otherwise specifically indicated to the contrary.

When a list of items is given herein with an "or" before the last item, any one of the listed items or any suitable combination of two or more of the listed items may be selected and used.

Of course, the above described embodiments of the present disclosure are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. A system for ventilating a lung, comprising:
    a gas pump comprising an exhaust side and an intake side;
    a sealed chamber for enclosing the lung therein, and configured to apply a first pressure (P1) to an airway of the lung and apply a second pressure (P2) to an exterior surface of the lung enclosed therein; and
    a plurality of conduits and a plurality of valves, the conduits and valves connecting the gas pump to the sealed chamber for selectively regulating P1 and P2, wherein the plurality of valves comprises
        a first proportional valve connected to the exhaust side of the gas pump,
        a second proportional valve connected to the intake side of the gas pump, and
        a third proportional valve connected to the first proportional valve,
    and wherein the plurality of conduits comprises
        a first conduit extending through the sealed chamber and connected to the third proportional valve, for connecting an airway of the lung to the gas pump through the third proportional valve and the first proportional valve to supply the pressure applied to the airway of the lung, a second conduit connecting the second proportional valve to the sealed chamber for supplying the pressure applied to the exterior surface of the lung, and a third conduit connecting the second conduit to the first proportional valve, wherein the first pressure and the second pressure are selectively regulated through the first proportional valve by an exhaust pressure of the gas pump, the second pressure is selectively regulated through the second proportional valve by the exhaust pressure and an intake pressure of the gas pump, and the first pressure is further selectively reduced through the third proportional valve.

2. The system of claim 1, comprising a controller for controlling operations of the gas pump and the plurality of valves.

3. The system of claim 1, wherein the gas pump comprises a regenerative vacuum pump.

4. The system of claim 3, wherein the regenerative vacuum pump is a regenerative turbine.

5. The system of claim 1, wherein the gas pump comprises a single pump.

6. The system of claim 1, wherein the gas pump comprises a single turbine.

7. The system of claim 1, wherein the sealed chamber has a rigid internal wall defining a constant internal volume.

8. The system of claim 1, comprising pressure sensors for detecting pressures at different locations in the plurality of conduits and the sealed chamber.

9. The system of claim 1, comprising flow sensors for detecting fluid flow rates at different locations in the plurality of conduits.

* * * * *